US009446146B2

(12) United States Patent
Daelken et al.

(10) Patent No.: US 9,446,146 B2
(45) Date of Patent: Sep. 20, 2016

(54) METHODS AND AGENTS FOR IMPROVING TARGETING OF CD138 EXPRESSING TUMOR CELLS

(75) Inventors: Benjamin Daelken, Frankfurt am Main (DE); Christoph Uherek, Seligenstadt (DE); Kenneth Anderson, Wellesley, MA (US); Teru Hideshima, Brookline, MA (US); Christoph Bruecher, Eschborn (DE); Frank Osterroth, Dietzenbach (DE); Silke Aigner, Frankenthal (DE); Matthias Germer, Langen (DE)

(73) Assignees: BIOTEST AG, Dreieich (DE); IMMUNOGEN INC., Waltham, MA (US); Dana-Farber Cancer Institute, Boston, MA (US)

( * ) Notice: Subject to any disclaimer, the term of this patent is extended or adjusted under 35 U.S.C. 154(b) by 121 days.

(21) Appl. No.: 12/342,815

(22) Filed: Dec. 23, 2008

(65) Prior Publication Data
US 2009/0169570 A1 Jul. 2, 2009

Related U.S. Application Data

(60) Provisional application No. 61/016,614, filed on Dec. 26, 2007, provisional application No. 61/087,466, filed on Aug. 8, 2008, provisional application No. 61/087,590, filed on Aug. 8, 2008.

(51) Int. Cl.
*A61K 39/00* (2006.01)
*A61K 47/48* (2006.01)
*C07K 16/28* (2006.01)

(52) U.S. Cl.
CPC ..... *A61K 47/48561* (2013.01); *A61K 47/4863* (2013.01); *A61K 47/48384* (2013.01); *A61K 47/48407* (2013.01); *A61K 47/48569* (2013.01); *C07K 16/2896* (2013.01); *A61K 2039/505* (2013.01); *C07K 2317/34* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 3,896,111 | A | 7/1975 | Kupchan et al. |
|---|---|---|---|
| 4,137,230 | A | 1/1979 | Hashimoto et al. |
| 4,151,042 | A | 4/1979 | Higashide et al. |
| 4,169,888 | A | 10/1979 | Hanka et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,418,064 | A | 11/1983 | Powell et al. |
| 4,424,219 | A | 1/1984 | Hashimoto et al. |
| 4,444,887 | A | 4/1984 | Hoffmann |
| 4,761,111 | A | 8/1988 | Brown |
| 5,053,394 | A | 10/1991 | Ellestad et al. |
| 5,208,020 | A | 5/1993 | Chari et al. |
| 5,367,086 | A | 11/1994 | Rao |
| 5,475,092 | A | 12/1995 | Chari et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,585,499 | A | 12/1996 | Chari et al. |
| 5,639,641 | A | 6/1997 | Pedersen et al. |
| 5,703,247 | A | 12/1997 | Kingston et al. |
| 5,705,508 | A | 1/1998 | Ojima et al. |
| 5,712,374 | A | 1/1998 | Kuntsmann et al. |
| 5,714,586 | A | 2/1998 | Kuntsmann et al. |
| 5,739,350 | A | 4/1998 | Kelly et al. |
| 5,763,477 | A | 6/1998 | Duvvuri et al. |
| 5,773,001 | A | 6/1998 | Hamann et al. |
| 5,814,318 | A | 9/1998 | Lonberg et al. |
| 5,831,012 | A | 11/1998 | Nilsson et al. |

(Continued)

FOREIGN PATENT DOCUMENTS

| CA | 20042486285 A1 | 2/2006 |
|---|---|---|
| EP | 0239400 A2 | 9/1987 |

(Continued)

OTHER PUBLICATIONS

Tassone et al, Blood, 104:3688-3696, 2004.*
Ravi et al ,Cancer Res. 52:127-131, 1992.*
Paul, Fundamental Immunology, 3rd Edition, 1993, pp. 292-295.*
Rudikoff et al Proc. Natl. Acad. Sci. USA 1982 vol. 79: p. 1979.*
Casset et al, BBRC 307, 198-205 2003.*
Pascalis et al the Journal of Immunology vol. 169, 3076-3084, 2002.*
Akkina et al., "Modeling human lymphoid precursor cell gene therapy in the SCID-hu mouse," Blood, 1994, 84, pp. 1393-1398.

(Continued)

*Primary Examiner* — Lei Yao
(74) *Attorney, Agent, or Firm* — Joyce von Natzmer; Agris & von Natzmer LLP

(57) ABSTRACT

Disclosed are immunoconjugates having specificity for CD138 that diminish adhesion of CD138 expressing tumor cells to stroma cells and methods of using the same. This diminished adhesion renders the tumor cells not only susceptible to the immunoconjugate, but also to other agents, in particular cytotoxic agents.

10 Claims, 21 Drawing Sheets

(56) References Cited

U.S. PATENT DOCUMENTS

| | | | |
|---|---|---|---|
| 5,846,545 A | 12/1998 | Chari et al. | |
| 5,877,296 A | 3/1999 | Hamann et al. | |
| 5,892,063 A | 4/1999 | Zheng et al. | |
| 5,998,656 A | 12/1999 | Holton et al. | |
| 6,002,023 A | 12/1999 | Kingston et al. | |
| 6,005,079 A | 12/1999 | Casterman et al. | |
| 6,080,777 A | 6/2000 | Schiff | |
| 6,087,362 A | 7/2000 | El-Rashidy | |
| 6,333,410 B1 | 12/2001 | Chari et al. | |
| 6,340,701 B1 | 1/2002 | Chari et al. | |
| 6,407,213 B1 | 6/2002 | Carter et al. | |
| 6,436,931 B1 | 8/2002 | Chari et al. | |
| 6,534,628 B1 | 3/2003 | Nilsson et al. | |
| 6,534,660 B1 | 3/2003 | Yongxin et al. | |
| 6,596,757 B1 | 7/2003 | Chari et al. | |
| 6,706,708 B2 | 3/2004 | Chari et al. | |
| 6,716,821 B2 | 4/2004 | Zhao et al. | |
| 6,740,734 B1 | 5/2004 | Nilsson et al. | |
| 6,756,397 B2 | 6/2004 | Zhao et al. | |
| 7,271,245 B2 | 9/2007 | Felding-Habermann et al. | |
| 7,534,427 B2 | 5/2009 | Goldenberg et al. | |
| 7,612,178 B2 * | 11/2009 | Hariharan et al. | 530/387.1 |
| 8,600,223 B2 | 12/2013 | Etter et al. | |
| 2002/0006379 A1 | 1/2002 | Hansen et al. | |
| 2002/0131967 A1* | 9/2002 | Nakamura et al. | 424/143.1 |
| 2003/0004210 A1 | 1/2003 | Chari et al. | |
| 2003/0055226 A1 | 3/2003 | Chari et al. | |
| 2004/0024049 A1 | 2/2004 | Baloglu et al. | |
| 2004/0082764 A1 | 4/2004 | Kunz et al. | |
| 2004/0087649 A1 | 5/2004 | Chari et al. | |
| 2004/0126379 A1 | 7/2004 | Adolf et al. | |
| 2004/0235840 A1 | 11/2004 | Chari et al. | |
| 2004/0241817 A1 | 12/2004 | Umana et al. | |
| 2005/0123549 A1 | 6/2005 | Payne et al. | |
| 2005/0272128 A1 | 12/2005 | Umana et al. | |
| 2006/0045877 A1* | 3/2006 | Goldmakher | 424/133.1 |
| 2006/0233814 A1 | 10/2006 | Goldmakher et al. | |
| 2007/0183971 A1 | 8/2007 | Goldmakher | |
| 2008/0171040 A1 | 7/2008 | Ebens et al. | |
| 2009/0087429 A1 | 4/2009 | Chen et al. | |
| 2009/0169570 A1 | 7/2009 | Daelken et al. | |
| 2009/0175863 A1 | 7/2009 | Kraus et al. | |
| 2009/0181038 A1 | 7/2009 | Schulz et al. | |
| 2009/0232810 A1 | 9/2009 | Kraus et al. | |
| 2009/0317391 A1 | 12/2009 | Fanidi et al. | |
| 2011/0123554 A1 | 5/2011 | Osterroth et al. | |
| 2013/0028862 A1 | 1/2013 | Fyfe et al. | |

FOREIGN PATENT DOCUMENTS

| | | |
|---|---|---|
| EP | 0519596 A1 | 12/1992 |
| EP | 0592106 A1 | 4/1994 |
| EP | 2006381 A1 | 12/2008 |
| JP | 2006-513203 | 4/2006 |
| JP | 2007077155 A | 3/2007 |
| JP | 2007-523650 A1 | 8/2007 |
| JP | 2007-525466 | 9/2007 |
| JP | 2008535491 A | 9/2008 |
| JP | 2010-540132 | 12/2010 |
| RU | 2010130977 A | 2/2012 |
| RU | 2010130993 A | 2/2012 |
| WO | 8802594 | 4/1988 |
| WO | 91/09967 A1 | 7/1991 |
| WO | 91/10741 A1 | 7/1991 |
| WO | 96/33735 A1 | 10/1996 |
| WO | 96/34096 A1 | 10/1996 |
| WO | 98/16654 A1 | 4/1998 |
| WO | 98/24893 A1 | 6/1998 |
| WO | 98/46645 A2 | 10/1998 |
| WO | 98/50433 | 11/1998 |
| WO | 0216602 A2 | 2/2002 |
| WO | 2004/099379 A2 | 11/2004 |
| WO | 2006008548 A2 | 1/2006 |
| WO | 2006/099875 A1 | 9/2006 |
| WO | 2006110466 A2 | 10/2006 |
| WO | 2007/066109 A1 | 6/2007 |
| WO | 2007/144046 A2 | 12/2007 |

OTHER PUBLICATIONS

Anttonen et al., "High syndecan-1 expression is associated with favourable outcome in squamous cell lung Carcinoma treated with radical surgery," Lung Cancer, Jun. 2001, 32(3), pp. 297-305.

Barbareschi et al., "High syndecan-1 expression in breast Carcinoma is related to an aggressive phenotype and to poorer prognosis," Cancer, Aug. 1, 2003, 98(3), pp. 474-483.

Bernfield et al., "Biology of the syndecans: a family of transmembrane heparan sulfate proteoglycans," Annu RevCell Biol, 1992, 8, pp. 365-393.

Beste et al., "Small antibody-like proteins with prescribed ligand specificities derived from the lipocalin fold," Proc. Natl. Acad. Sei. USA, 1999, 96, pp. 1898-1903.

Bhattacharyy et al., "Maytansine binding to the vinblastine sites of tubulin," FEBS Lett, 1977, 75, pp. 159-162.

Blättler et al., "Drugs to Enhance the Therapeutic Potency of Anticancer Antibodies: Antibody-Drug Conjugates as Tumor-Activated Prodrugs," Anticancer Agents—Frontiers in Cancer Chemotherapy, American Chemical Society, Washington, DC, 2001, pp. 317-338.

Bross et al., "Approval summary: gemtuzumab ozogamicin in relapsed acute myeloid leukemia," Clin Cancer Res, 2001, 7, pp. 1490-1496.

Carbone et al., "AIDS-related plasma—blastic lymphomas of the oral cavity and jaws: a diagnostic dilemma," Ann. Otol. Rhinol. Laryngol., 1999, 108, pp. 95-99.

Carbone et al., "Reed-Sternberg cells of classical Hodgkin's disease react with the plasma cell-specific monoclonal antibody B-B4 and express human syndecan-1," Blood, 1997, 89, pp. 3787-3794.

Carter P., "Improving the efficacy of antibody-based Cancer therapies," Nat Rev Cancer, 2001, 1, pp. 118-129.

Chari et al., "Goldmacher VS. Immunoconjugates containing novel maytansinoids: promising anticancerdrugs," Cancer Res., 1992, 52, pp. 127-131.

Chari et al., "Goldmacher VS. Enhancement of the selectivity and antitumor efficacy of a CC-1065 analogue through immunoconjugate formation," Cancer Res., 1995, 55, pp. 4079-4084.

Charnaux et al., "RANTES (CCL5) induces a CCR5-dependent accelerated shedding of syndecan-1 (CD138) and syndecan-4 from HeLa cells and forms complexes with the shed ectodomains of these proteoglycans as well as with those of CD44," Glycobiology, 2005, 5(2) pp. 119-130.

Chen et al., "Engraftment of human hematopoietic precursor cells with secondary transfer potential in SCID-hu mice," Blood, 1994, 84, pp. 2497-2505.

Chilosi et al., "CD138/syndecan-1: a useful immunohistochemical marker of normal and neoplastic plasma cells on routine trephine bone marrow biopsies," Mod Pathol., 1999, 12 pp. 1101-1106.

Clement et al., "B-B2 and B-B4: two new mAb against secreting plasma cells," SFSe, ed. J. Leukocyte Typing V. Oxford: Oxford University Press, 1995 pp. 714-715.

Couturier et al., "Validation of 213Bi-alpha radioimmunotherapy for multiple myeloma," Clinical Cancer Research, 5(10 Suppl.), Oct. 1999, pp. 3165s-3170s.

Davies et al., "Distribution and Clinical Significance of Heparan Sulfate Proteoglycans," Ovarian Cancer Clin Cancer Res., 2004, 10(15), pp. 5178-5186.

Dhodapkar et al., "Antitumor monoclonal abs enhance cross-presentation of Cellular antigens and the generation of myeloma-specific killer T cells by dendritic cells," J Exp Med, Jan. 7, 2002, 195(1), pp. 125-33.

Dhodapkar et al., "T cells from the tumor microenvironment of patients with progressive myeloma can generate strong, tumor-specific cytolytic responses to autologous, tumor-loaded dendritic cells," Proc Natl Acad Sci U S A., Oct. 1, 2002, 99(20) pp. 13009-13013, Epub Sep. 16, 2002.

(56) References Cited

OTHER PUBLICATIONS

Dhodapkar et al., "Syndecan-1 is a multifunctional regulator of myeloma pathobiology: control of tumor cell survival, growth, and bone cell differentiation," Blood, 1998, 91, pp. 2679-2688.
Dore et al., "Identification and location on syndecan-1 core protein of the epitopes of B-B2 and B-B4 monoclonal antibodies," FEBS Lett., 1998, 426, pp. 67-70.
Dowell et al., "Pharmacokinetics of gemtuzumab ozogamicin, an antibody-targeted chemotherapy agent for the treatment of patients with acute myeloid leukemia in first relapse," J Clin Pharmacol, 2001, 41, pp: 1206-1214.
Edinger et al., "Noninvasive assessment of tumor cell proliferation in animal models," Neoplasia, 1999, 1, pp. 303-310.
Gattei et al., "Characterization of Anti-CD138 monoclonal antibodies as tools for investigating the molecular polymorphism of syndecan-1 in human lymphoma cells," Br J Haematol, 1999, 104, pp. 152-162.
Hamann et al., "An anti-CD33 antibody-calicheamicin conjugate for treatment of acute myeloid leukemia. Choice of linker," Bioconjug Chem, 2002, 13, pp. 40-46.
Han et al., "New insights into syndecan-2 expression and tumourigenic activity in colon carcinoma cells," J Mol Histol., 2004, 35(3), pp. 319-326.
Horvathova et al., "Identification of novel and specific antigens of human plasma cells by mAb," SFSe, ed. Leucocyte Typing V. Oxford: Oxford University Press, 1995, pp. 713-714.
Jokimaa et al., "Expression of syndecan-1 in human placenta and decidua," Placenta, Mar.-Apr. 1998, 19(2-3), pp. 157-163.
Jokimaa et al., "Placental expression of syndecan 1 is diminished in preeclampsia," Am J Obstet Gynecol, Dec. 2000, 183(6), pp. 1495-1498.
Krebs et al., "High-throughput generation and engineering of recombinant human antibodies," J. Immunol, Methods 254, 2001, pp. 67-84.
Kupchan et al., "Structural requirements for antileukemic activity among the naturally occurring and semisynthetic maytansinoids," J Med Chem, 1978, 21, pp. 31-37.
Kyoizumi et al., "Implantation and maintenance of functional human bone marrow in SCID-hu mice," Blood, 1992, 79, pp. 1704-1711.
Kyoizumi et al., "Preclinical analysis of cytokine therapy in the SCID-hu mouse," Blood, 1993, 81 pp. 1479-1488.
Liu et al., "Eradication of large colon tumor xenografts by targeted delivery of maytansinoids," Proc Natl Acad Sci U S A, 1996, 93, pp. 8618-8623.
McCune et al., "The SCID-hu mouse: murine model for the analysis of human hematolymphoid differentiation and function," Science, 1988, 241, pp. 1632-1639.
Mennerich et al. "Shift of syndecan-1 expression from epithelial to stromal cells during progression of solid tumours," Eur J Cancer, Jun. 2004, 40(9), pp. 1373-1382.
Mosmann T., "Rapid colorimetric assay for cellular growth and survival: application to proliferation and cytotoxicity assays," J Immunol Methods, 1983, 65, pp. 55-63.
Mukunyadzi et al., "The level of syndecan-1 expression is a distinguishing feature in behavior between keratoacanthoma and invasive cutaneous squamous cell carcinoma," Mod Pathol., Jan. 2002, 15(1), pp. 45-49.
Namikawa et al., "Growth of human myeloid leukemias in the human marrow environment of SCID-hu mice," Blood, Oct. 15, 1993, 82(8), pp. 2526-2536.
O'Connell FP et al., "CD138 (Syndecan-1), a Plasma Cell Marker Immunohistochemical Profile in Hematopoietic and Nonhematopoietic Neoplasms," Am J Clin Pathol, 2004, 121, pp. 254-263.
Ojima et al., "Tumor-specific novel taxoid-monoclonal antibody conjugates," 2002, J. Med. Chem., 45, pp. 5620-5623.
Olafsen et al., "Covalent disulfide-linked anti-CEA diabody allows site-specific conjugation and radiolabeling for tumor targeting applications," 2004, Prot. Eng. Design & Selection, 17, 1, pp. 21-27.

Orosz et al., "Syndecan-1 expression in different soft tissue tumours," Anticancer Res., 2001, 21(1B), pp. 733-737.
Padlan, EA, "A possible procedure for reducing the immunogenicity of antibody variable domains while preserving their ligand-binding properties," Mol. Immunol., 1991, 28 pp. 489-498.
Palacios et al., "B-B4 monoclonal antibody and identification of human bone marrow plasma cells (including response)," BR J Haematol, 1997, 96, pp. 654-657.
Tassone et al.: "Cytotoxic activity of the maytansinoid immunoconjugate B-B4-DM1 against CD138+ multiple myeloma cells," in Blood Dec. 1, 2004, vol. 104, No. 12, Dec. 1, 2004, pp. 3688-3696.
Sharkey Robert M et al: "Targeted therapy of Cancer: new prospects for antibodies and immunoconjugates" in CA: A Cancer Journal for Clinicians Jul.-Aug. 2006, vol. 56, No. 4, Jul. 2006, pp. 226-243.
Turner et al.: "1311-Anti CD20 radioimmunotherapy of relapsed or refractory non-Hodgkins lymphoma: a phase II clim'cal trial of a nonmyeloablative dose regimen of chimeric rituximab radiolabeled in a hospital," in Cancer Biotherapy & Radiopharmaceuticals Aug. 2003, vol. 18, No. 4, Aug. 2003, pp. 513-524.
Israel et al.: "Plasmapheresis and inmunological control of cancer," in Lancet Sep. 18, 1976, vol. 2, No. 7986, Sep. 18, 1976, pp. 642-643.
Cortesini: "Pancreas cancer and the role of soluble immunoglobulin-like transcript 3 (ILT3)," in JOP: Journal of the Pancreas 2007, vol. 8, No. 6, Nov. 1, 2007, pp. 697-703.
Payne G., "Progress in immunoconjugate cancer therapeutics," Cancer Cell, 2003, 3, pp. 207-212.
Pegram et al. "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment," 1998, J. Clin. Oncol., 16, pp. 2659-2671.
Post et al., "Efficacy of an anti-CD138 immunotoxin and doxorubicin on drug-resistant and drug-sensitive myeloma cells," Int J Cancer, Nov. 12, 1999, 83(4), pp. 571-576.
Rawstron et al., "Circulating plasma cells in multiple myeloma: characterization and correlation with disease stage," Br J Haematol, 1997, 97, pp. 46-55.
Remillard et al., "Antimitotic activity of the potent tumor inhibitor maytansine," Science, 1975,189, pp. 1002-1005.
Rintala et al., "Association of syndecan-1 with tumor grade and histology in primary invasive cervical carcinoma," Gynecol Oncol, Dec. 1999, 75(3), pp. 372-378.
Roguska et al., "Humanization of murine monoclonal antibodies through variable domain resurfacing," Proc Natl Acad Sci U S A, 1994, 91, pp. 969-973.
Ross et al., "Anticancer Antibodies," Am J Clin Path, 2003, 119, pp. 472-485.
Ross et al., "Prostate stem cell antigen as therapy target: tissue expression and in vivo efficacy of an immunoconjugate," Cancer Res, May 1, 2002, 62(9), pp. 2546-2553.
Sanderson et al., "B lymphocytes express and lose syndecan at specific stages of differentiation," Cell Regul, 1989, 1, pp. 27-35.
Sandhu et al., "Human hematopoiesis in SCID mice implanted with human adult cancellous bone," Blood, 1996, 88, pp. 1973-1982.
Sasaki et al., "Bisphosphonate risedronate reduces metastatic human breast cancer burden in bone in nude mice," Cancer Res, 1995, 55, pp. 3551-3557.
Schneider et al., "Two subsets of peripheral blood plasma cells defined by differential expression of CD45 antigen," Br J Haematol, 1997, 97, pp. 56-64.
Sebestyen et al., "Syndecan-1 (CD138) expression in human non-Hodgkin lymphomas," Br J Haematol, 1999, 104(2), pp. 412-419.
Seftalioglu et al., "Syndecan-1/CD138 expression in normal myeloid, acute lymphoblastic and myeloblastic leukemia cells," Acta Histochem, 2003, 105, pp. 213-221.
Seftalioglu et al., "Syndecan-1 (CD138) expression in acute myeloblastic leukemia cells—an immuno electron microscopic study," Acta Oncol, 2003, 42, pp. 71-74.
Senter et al., "Cures and regressions of established tumors with monoclonal antibody auristatin conjugates," Abstract #2062, Proc.

(56) References Cited

OTHER PUBLICATIONS

Am. Assoc. Can. Res. (San Francisco, CA: American Association for Cancer Res.), Mar. 2002, 43 pp. 414-415.
Sievers et al., "Efficacy and safety of gemtuzumab ozogamicin in patients with CD33-positive acute myeloid leukemia in first relapse," J. Clin. Oncol, 2001, 19, pp. 3244-3254.
Sievers et al., "Mylotarg: antibody-targeted chemotherapy comes of age," Curr. Opin. Oncol., 2001, 13, pp. 522-527.
Smith R., Single chain antibody variable region fragments; www.stanford.edu/ ~smithr/science/scfv.html (last updated in May 2001).
Stanley et al., "Syndecan-1 expression is induced in the stroma of infiltrating breast carcinoma," Am J Clin Pathol., Sep. 1999, 112(3), pp. 377-383.
Studnicka et al. "Human-engineered monoclonal antibodies retain full specific binding activity by preserving non-CDR complementarity-modulating residues," Protein Eng., 1994, 7(6), pp. 805-814.
Sun et al., "Large scale and clinical grade purification of syndecan-1+ malignant plasma cells," J Immunol Methods, Jun. 23, 1997, 205(1), pp. 73-79.
Tolcher et al., "Cantuzumab mertansine, a maytansinoid immunoconjugate directed to the CanAg antigen: a phase I, pharmacokinetic, and biologic correlative study," J Clin Oncol, 2003, 21, pp. 211-222.
Urashima et al., "The development of a model for the homing of multiple myeloma cells to human bone marrow," Blood, 1997, 90, pp. 754-765.
Vogel, CW, "Preparation of immunoconjugates using antibody oligosaccharide moieties. Methods in Molecular Biology: Bioconjugation protocols strategies and methods," 2004, 283, pp. 87-108.
Vooijs et al., "Efficacy and toxicity of plasma-cell-reactive monoclonal antibodies B-B2 and B-B4 and their immunotoxins," Cancer Immunol Immunother, 1996, 42, pp. 319-328.
Ward et al. "Binding activities of a repertoire of single immunoglobin variable domains secreted from *Escherichia coli*," Nature, 1989, 341, pp. 544-546.
Wargalla et al., "Rate of internalization of an immunotoxin correlates with cytotoxic activity against human tumor cells," Proc. Natl. Acad. Sci. USA, 1989, 86, pp. 5146-5150.
Wijdenes et al. "A plasmocyte selective monoclonal antibody (B-B4) recognizes syndecan-1," Br J Haematol, 1996, 94, pp. 318-323.
Wijdenes et al., "CD138" J Biol Regul Homeost Agents, Apr.-Jun. 2002, 16(2), pp. 152-155.
Wiksten et al. "Epithelial and stromal syndecan-1 expression as predictor of outcome in patients with gastric cancer," Int J Cancer, Jan. 20, 2001, 95(1), pp. 1-6.
Witzig et al., "Detection of myeloma cells in the peripheral blood by flow cytometry," Cytometry, 1996, 26, pp. 113-120.
Xie et al., "Pharmacokinetics and biodistribution of the antitumor immunoconjugate, cantuzumab mertansine (huC242-DM1), and its two components in mice," J Pharmacol Exp Ther, Mar. 2004, 308(3), pp. 1073-1082.
Yang et al., "Genetically fluorescent melanoma bone and organ metastasis models," Clin Cancer Res, 1999, 5, pp. 3549-3559.
Yang et al., "Whole-body optical imaging of green fluorescent protein-expressing tumors and metastases," Proc Natl Acad Sci U S A, 2000, 97, pp. 1206-1211.
Tassone et al., Proc Amer Assoc Cancer Res, vol. 45, abstract#1425, Mar. 2004, abstract.
Supiot et al., "Compariosn of the Biologic Effects of MA5 and B-B4 Monoclonal Antibody Labeled with Iodine-131 and Bismuth-213 on Multiple Myeloma," Cancer, vol. 94, No. S4, pp. 1202-1209.
Tassone et al., "Cytotoxic activity of the maytansinoid immunoconjugate B-B4-DM1 against CD138+ multiple myeloma cells," Blood Journal, vol. 104 (12), Dec. 1, 2004, pp. 3688-3696.
Tassone et al., "In vitro and in vivo activity of the maytansinoid immunoconjugate huN901-N2'-Deacetyl-N2'-(3-Mercapto-1-Oxopropyl)-Maytansine against CD56+ Multiple Myeloma Cells," Cancer Research, vol. 64, Jul. 1, 2004, pp. 4629-4636.
Tassone et al, Blood, Nov. 16, 2003, vol. 102, 45th ASH meeting abstract 449s-450a (abstract).
Rudikoff et al., "Single amino acid substitution altering antigen-binding specificity," PNAS, 1982, 79(6), pp. 1979-1983.
Kipriyanov et al., "Generation and production of engineered antibodies," Mol. Biotechnol., 2004, 26(1), pp. 39-60.
Hwang et al., "Immunogenicity of engineered antibodies," Methods, 2005, 36(1), pp. 3-10.
Buchsbaum, "Experimental approaches to increase radiolabeled antibody localization in tumors," Cancer Research, 1995, 55, pp. 5729s-5732s.
Wu et al., "Humanization of a murine monoclonal antibody by simultaneous optimization of framework and CDR residues," JMB, 1999, 294, pp. 151-162.
Beatty et al., "Effect of Specific Antibody Pretreatment on Liver Uptake of (superscript)111In-labeled Anticarcinoembryonic Antigen Monoclonal Antibody in Nude Mice Bearing Human Colon Cancer Xenografts," Cancer Research, 1989, 49, pp. 1587-1594.
Winter et al., "Human antibodies," Immunology Today, Jun. 1993, 14(6), pp. 243-246.
Hamilton, "Molecular engineering; applications to clinical laboratory," Clin. Chem., 1993, 39(9), pp. 1988-1997.
Roitt et al, Immunology Illustrated (original book 5th Edition), Nankodo, Feb. 10, 2000, 1st Edition, pp. 77-78. *.
Ishida, "Chemotherapy for Multiple Myeloma," in Nihon Rinsho (Japan Clinical), Dec. 1, 2007, vol. 65, No. 12, pp. 2280-2284.
Ozaki et al., "Humanized Anti-HM1.24 Antibody and Antibody-Based Therapy for Multiple Myeloma," in Gan no Rinsho (Clinical of Cancer), 2002, vol. 48, No. 2, pp. 101-108.

* cited by examiner

FIG. 1
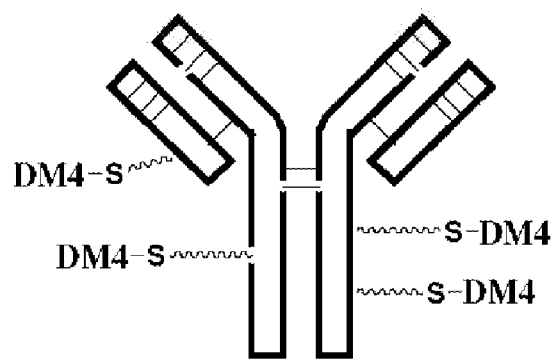
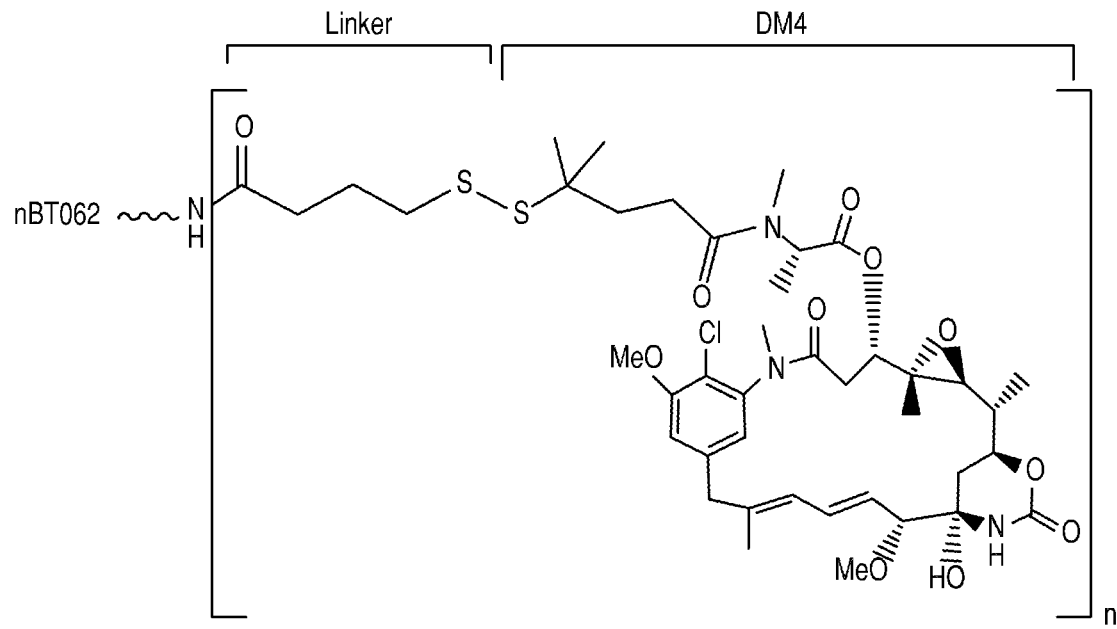
*n is approximately 3.5 drug linked per antibody molecule
FIG. 2

DCC: 1,3-dicyclohexylcarbodiimide
DTT: Dithiothreitol
DME: 1,2-Dimethoxyethane

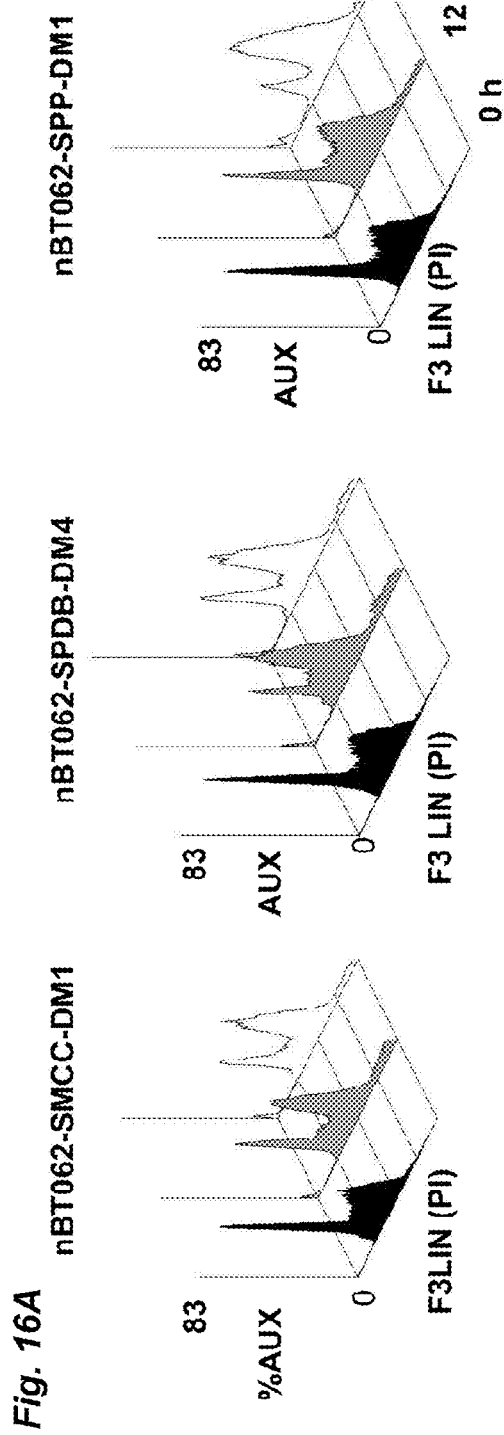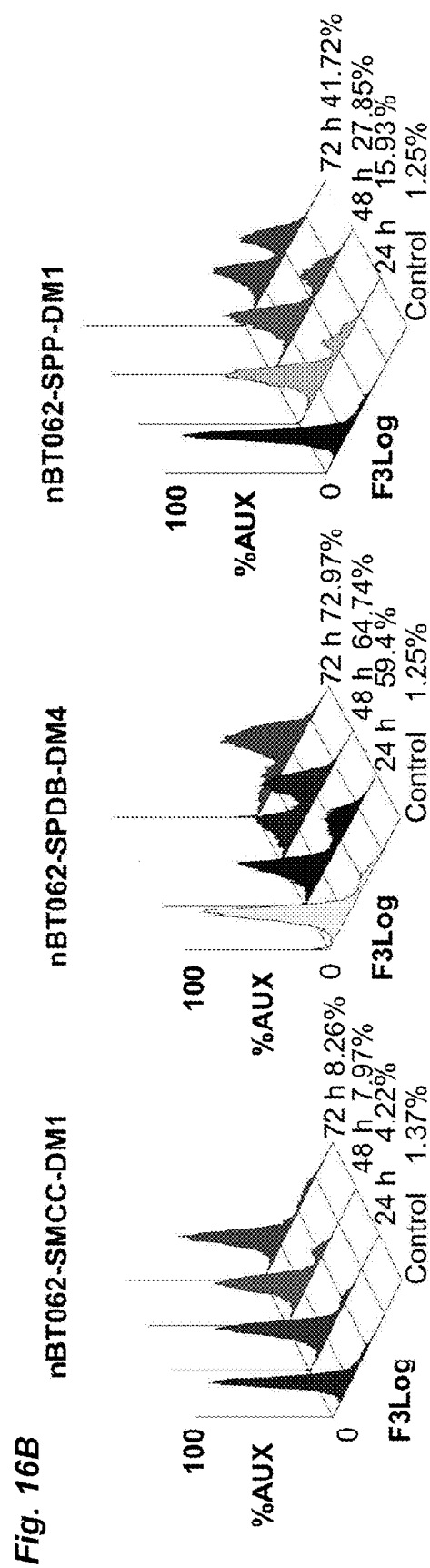
Fig. 16A
Fig. 16B

METHODS AND AGENTS FOR IMPROVING TARGETING OF CD138 EXPRESSING TUMOR CELLS

CROSS-REFERENCE TO RELATED APPLICATIONS

This application claims the benefit of U.S. provisional application 61/016,614, filed Dec. 26, 2007, provisional application 61/087,466, file Aug. 8, 2008 and provisional application 61/087,590, also filed on Aug. 8, 2008, which are incorporated herein by reference in their entirety.

FIELD OF THE INVENTION

The present invention relates to the use of immunoconjugates against the antigen CD138 and compositions comprising the immunoconjugates to diminishing adhesion of stroma cells to CD138 expressing target cells and thus to more effectively treat disease states involving CD138 expressing cells.

BACKGROUND

CD138, which acts as a receptor for the extracellular matrix, is overexpressed on multiple myeloma (MM) cells and has been shown to influence MM cell development and/or proliferation. CD138 is also expressed on cells of ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) to name just a few.

The publications and other materials, including patents, used herein to illustrate the invention and, in particular, to provide additional details respecting the practice are incorporated by reference. For convenience, the publications are referenced in the following text by author and date and/or are listed alphabetically by author in the appended bibliography.

Tassone et al. (2004) have reported excellent binding of the murine IgG1 antibody B-B4 to the CD138 antigen expressed on the surface of MM cells. Tassone also reported high cytotoxic activity of the immunoconjugate B-B4-DM1, which comprises the maytansinoid DM1 as an effector molecule, against multiple myeloma cells (see also US Patent Publ. 20070183971).

Tassone also showed that his B-B4 conjugate was effective even in the bone marrow microenvironment which induces in multiple myeloma (MM) cells resistance to many drugs commonly administered to MM patients, including, for example dexamethasone. Tassone's immunoconjugates were able to effectively destroy MM tumor cells in the bone marrow stroma environment.

While Tassone et al. have contributed to providing an effective treatment of MM and a composition of matter that may be employed in such a treatment, there remain a number of needs in the art.

There remains a need for improved treatments using immunoconjugates based on B-B4. There is also a need for effective treatments employing B-B4 based immunoconjugates that show one or more advantageous properties. Properties of the immunoconjugate preferably include improved antigen binding, improved killing of tumor cells comprising, in particular of CD138 expressing tumor cells, and cells accessory thereto or more homogenous binding of the target, but in particular the ability to more effectively combat disease states associated with CD138 expressing cells.

SUMMARY OF THE INVENTION

The invention is directed at a method for diminishing adhesion of stroma cells to CD138 expressing tumor cells in tumor cells of a subject in need thereof comprising:
administering to said tumor cells an immunoconjugate targeting said CD138 expressing tumor cells, in particular one containing a cleavable linker and an effector as disclosed herein, in an amount effective to diminish adhesion of stroma cells to CD138 expressing tumor cells, and optionally administering to said tumor cells a further cytotoxic agent in a growth of tumor cells inhibiting, delaying and/or preventing amount.

The adhesion may be diminished by at least about 10%, about 20%, about 30%, about 40%, about 50%, about 60%, about 70%, about 80% or more and/or may results in alleviation of adhesion mediated drug resistance, which includes adhesion mediated drug resistance against a further cytotoxic agent (that is not one of the above immunoconjugates) and wherein said further cytotoxic agent is administered in a growth of tumor cells inhibiting, delaying and/or preventing amount. The immunoconjugate and this cytotoxic agent(s) may thus be administered consecutively, wherein administration of the cytotoxic agent may follow the administration of the immunoconjugate or may be co-administered.

The immunoconjugate of the present invention in particular comprises
(a) an engineered targeting antibody, and
(b) an effector molecule,
wherein said immunoconjugate homogenously targets CD138 expressing target cells.

The engineered targeting antibody of the present invention may
(i) consist essentially of antigen binding region (ABR) against CD138 of a non-human antibody, or
(ii) comprise an antigen binding region (ABR) against CD138, wherein said antigen binding region is of a non-human antibody, and a further antibody region, wherein at least part of said further antibody region is of a human antibody.

The ABR may comprise:
(a) heavy chain variable region CDR3 comprising amino acid residues 99 to 111 of SEQ ID NO: 1, and
(b) light chain variable region CDR3 comprising amino acid residues 89 to 97 of SEQ ID NO: 2, respectively.

The ABR may further comprise:
(a) heavy chain variable region CDR1 and CDR2 comprising amino acid residues 31 to 35 and 51 to 68 of SEQ ID NO: 1, and/or
(b) light chain variable region CDR1 and CDR 2 comprising amino acid residues 24 to 34 and 50 to 56 of SEQ ID NO: 2, respectively.

The further antibody region may comprise:
(a) amino acid residues 123 to 448 of SEQ ID NO: 1, and/or
(b) amino acid residues 108 to 214 of SEQ ID NO: 2, respectively and mutations thereof that
(i) maintain or lower the antibody-dependent cytotoxicity and/or complement-dependent cytotoxicity of the engineered targeting antibody and/or
(ii) stabilize the engineered targeting antibody.

The effector molecule may be attached to said engineered targeting antibody via a linker. The linker may comprise a disulfide bond. The effector molecule (e.g., DM4) may provide sterical hindrance between the targeting antibody and the effector molecule. The effector molecule may be at least one maytansinoid (e.g., DM1, DM3, or DM4) taxane or a CC1065, or an analog thereof.

The immunoconjugate may bind CD138 with a targeting variation of less than 150%, 140%, 130%, 120%, 110%, 100%, 90%, 80%, 70%, 60% or 50%.

The present invention is also directed at an immunoconjugate comprising:
a targeting agent targeting CD138 comprising
an isolated polypeptide comprising an amino acid sequence of an immunoglobulin heavy chain or part thereof, wherein said immunoglobulin heavy chain or part thereof has at least 70% sequence identity with SEQ ID NO:1. A constant region of said immunoglobulin heavy chain or said part thereof may be an IgG4 isotype constant region.

The present invention is also directed at a method of treating MM in a subject, comprising:
providing one of more of the immunoconjugates specified herein, and
administering to said subject said immunoconjugate in an amount effective to treat multiple myeloma.

The targeting agent of the immunoconjugate may comprise a light chain sequence having at least about 70% sequence identity with SEQ ID NO:2. The targeting agent of the immunoconjugate may also comprise a heavy chain sequence having at least about 70% sequence identity with SEQ ID NO:1.

The present invention is also directed at a method for immunoconjugate mediated drug delivery comprising:
providing one or more of the immunoconjugates specified herein, and
administering said immunoconjugate in a therapeutically effective amount, wherein said IgG4 isotype alleviates ADCC, complement dependent cytotoxicity and/or Fc-mediated targeting of hepatic FcR.

The present invention is also directed at a method for inhibiting, delaying and/or preventing the growth of tumor cells in a cell culture comprising
administering to said cell culture a growth of tumor cells inhibiting, delaying and/or preventing effective amount of one or more of the immunoconjugates specified herein. The effective amount may induce cell death or continuous cell cycle arrest in CD138 expressing tumor cells and, optionally, auxiliary cells that do not express CD138, in particular tumor stroma cells. The cells in said cell culture may be obtained from a cancer patient and, after administration of said effective amount of said immunoconjugate, the cells of said cell culture may be reimplanted into said cancer patient.

The present invention is also directed at a method for inhibiting, delaying and/or preventing the growth of a tumor comprising CD138 tumor cells and/or spread of tumor cells of such a tumor in a patient in need thereof, comprising
administering to said patient at least one or more of the immunoconjugates specified above in a growth of said tumor and/or spreading of said tumor cells inhibiting or reducing amount,
wherein said immunoconjugate inhibits, delays or prevents the growth and/or spread of said tumor cells.

The effector molecule of said immunoconjugate(s) may be a toxin, cytotoxic enzyme, low molecular weight cytotoxic drug, a pore-forming agent, biological response modifier, prodrug activating enzyme, an antibody, cytokine or a radionuclide.

Immunoconjugates of the present invention may be administered in a single dose of 5 mg/m$^2$ to about 300 mg/m$^2$, optionally at hourly, daily, weekly intervals or combinations thereof.

Multiple dose regimes include, hourly, daily and weekly regimes are part of the present invention and include in particular administration at intervals of 5, 6, 7, 8, 9, 10, 11, 12, 13, 14, 15, 16, 17, 18, 19, 20, 21, 22, 23 hours, 1, 2, 3, 4, 5, 6, 7 days, 1, 2, 3, 4, 5, 6, 7 or 8 weeks.

The present invention is also directed at a method for inhibiting, delaying and/or preventing the growth of a tumor and/or spread of malignant tumor cells in a patient in need thereof, comprising
(a) administering to said patient one or more cytotoxic agents and/or radiation in an amount effective to reduce tumor load; and
(b) administering to said patient at least one of the immunoconjugates specified herein in a growth of a tumor and/or spreading of tumor cells inhibiting, delaying or preventing amount,
wherein said immunoconjugate inhibits, delays or prevents the growth and/or spread of tumor cells comprising CD138 expressing cells.

The cytotoxic agent of any of the embodiments of the present invention may, in particular, be mephalan, vincristine, doxorubicin, dexamethasone, cyclophosphamide, etoposide, cytarabine, cisplatin, thalidomide, prednisone, thalidomide, bortezomib, lenalidomide, sorafenib, romidepsin or combinations thereof or may be antibody based.

The present invention is also directed at a method for treating a subject having a condition that would benefit from the suppression of myeloma cell survival, the method comprising:
(a) providing at least one of any of the immunoconjugates specified herein, and
(b) administering the immunoconjugate to the subject to selectively decrease survival or growth of said myeloma cells of said subject.

The present invention is also directed at a pharmaceutical composition comprising any of the immunoconjugates specified herein for the inhibition, delay and/or prevention of the growth of tumors and/or spread of tumor cells, and one or more pharmaceutically acceptable excipients.

The pharmaceutical composition may include cytotoxic agents as specified herein.

The present invention is also directed at a kit comprising, in separate containers, pharmaceutical compositions for use in combination to inhibit, delay and/or prevent the growth of tumors and/or spread of tumor cells, wherein one container comprises an effective amount of the above pharmaceutical composition, and wherein, a separate container comprises a second pharmaceutical composition comprising an effective amount of an agent, preferably a cytotoxic agent, for the inhibition, delay and/or prevention of the growth of tumors and/or spread of tumor cells, and one or more pharmaceutically acceptable excipients.

The present invention is also directed at a method for inhibiting, delaying and/or preventing growth of a tumor comprising CD138 tumor cells and/or spread of tumor cells of such a tumor in a subject in need thereof, comprising
(a) providing an immunoconjugate comprising:
an engineered targeting antibody against CD138 attached to an effector molecule via a cleavable linker, wherein said effector molecule is sterically hindered, and (b) administering to said subject the immunoconjugate of (a) in a growth of said tumor and/or spreading of said tumor cells inhibiting, delaying and/or preventing amount, wherein said immunoconjugate of (a) provides a growth of a tumor inhibiting activity that exceeds that of its unhindered counterpart by about 10%, about 20%, about 30%, about 40% or more.

A growth of a tumor inhibiting activity of an unhindered counterpart comprising a non-cleavable linker may exceed that of the growth of a tumor inhibiting activity of its unhindered counterpart comprising a cleavable linker, such as by at least about 5%, at least about 10%, up to about 15%.

Said engineered targeting antibody against CD138 may consist essentially of antigen binding region against CD138 of a non-human antibody or may comprise an antigen binding region against CD138 of a non-human antibody and a further antibody region, wherein at least part of said further antibody region is of a human antibody.

Said cleavable linker may comprise a disulfide bond. The effector molecule may be DM4. The immunoconjugate may be part of a pharmaceutical composition and may be administered to the subject in at least one dose in an amount from about 5 mg/m$^2$ to about 300 mg/m$^2$.

The present invention provides an immunoconjugate for use as a medicament wherein the immunoconjugate comprises:
(a) an engineered targeting antibody
    (i) consisting essentially of antigen binding region against CD138 of a non-human antibody, or
    (ii) comprising an antigen binding region against CD138, wherein said antigen binding region is of a non-human antibody,
a further antibody region, wherein at least part of said further antibody region is of a human antibody, and
(b) an effector molecule,
wherein said immunoconjugate homogenously binds to CD138.

The present invention provides a further immunoconjugate for use as a medicament comprising:
    a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1.

In particular, in one aspect of the invention the immunoconjugate of the above paragraph is for use in the treatment of multiple myeloma. In particular, the immunoconjugate can be used for the manufacture of a medicament for the treatment of multiple myeloma.

The present invention further provides an immunoconjugate for use in immunoconjugate mediated drug delivery to a patient, in particular for alleviation of ADCC, complement dependent cytotoxicity and/or Fc-mediated targeting of hepatic FcR, wherein the immunoconjugate comprises a targeting agent targeting CD138 comprising an isolated polypeptide comprising an amino acid sequence of an immunoglobulin heavy chain or part thereof, wherein said immunoglobulin heavy chain or part thereof has at least 70% sequence identity with SEQ ID NO:1, and wherein a constant region of said immunoglobulin heavy chain or part thereof is an IgG4 isotype constant region.

The present invention also provides tumor cells for use in the treatment of cancer in a patient wherein the tumor cells have been treated in cell culture with an immunoconjugate comprising:
(a) an engineered targeting antibody
    (i) consisting essentially of antigen binding region against CD138 of a non-human antibody, or
    (ii) comprising an antigen binding region against CD138, wherein said antigen binding region is of a non-human antibody,
a further antibody region, wherein at least part of said further antibody region is of a human antibody, and
(b) an effector molecule,
wherein said immunoconjugate homogenously binds to CD138.

The present invention also provides tumor cells for use in the treatment of cancer in a patient wherein the tumor cells have been treated in cell culture with an immunoconjugate comprising:
    a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1.

The present invention provides an immunoconjugate for use in inhibiting, delaying and/or preventing the growth of a tumor comprising CD138 tumor cells and/or spread of tumor cells of such a tumor in a patient, wherein the immunoconjugate comprises:
(a) an engineered targeting antibody
    (i) consisting essentially of antigen binding region against CD138 of a non-human antibody, or
    (ii) comprising an antigen binding region against CD138, wherein said antigen binding region is of a non-human antibody,
a further antibody region, wherein at least part of said further antibody region is of a human antibody, and
(b) an effector molecule,
wherein said immunoconjugate homogenously binds to CD138.

Alternatively, the present invention provides an immunoconjugate for use in inhibiting, delaying and/or preventing the growth of a tumor comprising CD138 tumor cells and/or spread of tumor cells of such a tumor in a patient, wherein the immunoconjugate comprises:
    a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1.

Still further, the present invention provides a medicament comprising an immunoconjugate and one or more cancer drugs as a combined preparation for simultaneous, separate or sequential use in the treatment of tumor cells comprising CD138 expressing cells, wherein the immunoconjugate comprises:
(a) an engineered targeting antibody
    (i) consisting essentially of antigen binding region against CD138 of a non-human antibody, or
    (ii) comprising an antigen binding region against CD138, wherein said antigen binding region is of a non-human antibody,
a further antibody region, wherein at least part of said further antibody region is of a human antibody, and
(b) an effector molecule,
wherein said immunoconjugate homogenously binds to CD138, and wherein the one or more cancer drugs are capable of reducing the tumor load.

Alternatively, the present invention provides a medicament comprising an immunoconjugate and one or more cancer drugs as a combined preparation for simultaneous, separate or sequential use in the treatment of tumor cells comprising CD138 expressing cells, wherein the immunoconjugate comprises:
  a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1, and wherein the one or more cancer drugs are capable of reducing the tumor load.

In a further aspect of the use of the above two paragraphs the combined preparation is to be administered to a patient who has been treated with radiation.

In an alternative aspect the present invention provides the use of an immunoconjugate for the manufacture of a medicament for treating tumor cells in a patient comprising CD138 expressing cells, wherein the immunoconjugate comprises:
(a) an engineered targeting antibody
  (i) consisting essentially of antigen binding region against CD138 of a non-human antibody, or
  (ii) comprising an antigen binding region against CD138, wherein said antigen binding region is of a non-human antibody,
  a further antibody region, wherein at least part of said further antibody region is of a human antibody, and
(b) an effector molecule,
wherein said immunoconjugate homogenously binds to CD138, and wherein the medicament is to be administered to a patient treated with radiation to reduce the tumor load.

Still further the present invention provides the use of an immunoconjugate for the manufacture of a medicament for treating tumor cells in a patient comprising CD138 expressing cells, wherein the immunoconjugate comprises:
  a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1, and wherein the medicament is to be administered to a patient treated with radiation to reduce the tumor load.

In the above paragraphs, the medicament is capable of inhibiting, delaying and/or preventing the growth of a tumor and/or spread of malignant tumor cells in a patient.

Further the present invention provides an immunoconjugate for suppression of myeloma cell survival in an individual wherein the immunoconjugate comprises:
(a) an engineered targeting antibody
  (i) consisting essentially of antigen binding region against CD138 of a non-human antibody, or
  (ii) comprising an antigen binding region against CD138, wherein said antigen binding region is of a non-human antibody,
  a further antibody region, wherein at least part of said further antibody region is of a human antibody, and
(b) an effector molecule,
wherein said immunoconjugate homogenously binds to CD138.

Still further the present invention provides an immunoconjugate for suppression of myeloma cell survival in an individual wherein the immunoconjugate comprises:
  a targeting agent targeting CD138 comprising
    an isolated polypeptide comprising an amino acid sequence of an immunoglobulin heavy chain or part thereof, wherein said immunoglobulin heavy chain or part thereof has at least 70% sequence identity with SEQ ID NO:1.

In the above two paragraphs the immunoconjugate is, in particular, capable of selectively decreasing the survival or growth of said myeloma cells in the individual.

Further, the present invention provides an immunoconjugate for use in inhibiting, delaying and/or preventing growth of a tumor comprising CD138 tumor cells and/or spread of tumor cells of such a tumor in a subject wherein the immunoconjugate comprises an engineered targeting antibody against CD138 attached to an effector molecule via a cleavable linker, wherein said effector molecule is sterically hindered.

In the above paragraph, the immunoconjugate is, in particular, capable of providing a tumor growth inhibiting activity that exceeds that of its unhindered counterpart by about 10%, about 20%, about 30%, about 40% or more.

The present invention also provides a CD138 targeting agent for use in a method for diminishing adhesion of stroma cells to CD138 expressing tumor cells in tumor cells of a subject.

The present invention further provides a medicament comprising a CD138 targeting agent and a further agent, such as an targeting immunoconjugate or a cytostatic agent, as a combined preparation for simultaneous (co-administration), separate or sequential use in a method of diminishing adhesion of stroma cells to CD138 expressing tumor cells in tumor cells in a subject.

In the above paragraph, the combined preparation is, in particular, capable of inhibiting, delaying and/or preventing growth of tumor cells in a subject.

BRIEF DESCRIPTION OF THE FIGURES

FIG. 1 provides a schematic representation of nBT062 having effector molecules attached.

FIG. 2 is a chemical representation of BT062.

FIG. 15 (B) depicts the cell viability of MM cells isolated from three different patients after treatment with nBT062-SPDB-DM4 for 2 days. FIG. 15 (C) shows Peripheral Blood Mononuclear Cells (PBMCs) derived from 3 healthy subjects that were cultured with nBT062-SPDB-DM4 for 72 h before cell viability was determined.

In FIG. 16 (B) OPM1 cells were cultured in the presence or absence of immunoconjugates for 24, 48 or 72 h. The percentage of apoptotic cells was assessed by Apo 2.7 antibody staining and flow-cytometric analysis. In FIG. 16 (C) OPM1 cells were cultured in the presence of 885 μg/ml nBT062-SPDB-DM4 for the indicated times (left panel) or with different concentrations of immunoconjugate (middle panel). The pan-caspase inhibitor zVAD-fmk blocked nBT062-SPDB-DM4 induced casapase -8, -9, and -3 and Poly (ADP-ribose) polymerase (PARP) cleavage in OPM1 cells (right panel).

FIG. 17 (D) shows experiments using Dexamethasone instead of immunoconjugate. FIG. 17 (E) shows the results of cell adhesion experiment with co-cultures of tumor cells and BMSCs in the presence or absence of immunoconjugates.

FIG. 18 (B) shows the effect of nBT062-SPDB-DM4, nBT062-SPP-DM1 or buffer control on tumor sizes in groups of SCID injected with $5 \times 10^6$ $OPM1^{GFP}$ cells. FIG. 18 (C) nBT062-SPDB-DM4 significantly increased survival (P<0.0023, dashed line, n=5) compared with the control group treated with vehicle only (solid line; normal saline, n=5). FIG. 18 (D) demonstrates that nBT062-SPDB-DM4 induces apoptosis in vivo.

DETAILED DESCRIPTION OF VARIOUS AND PREFERRED EMBODIMENTS OF THE INVENTION

Figure 3:
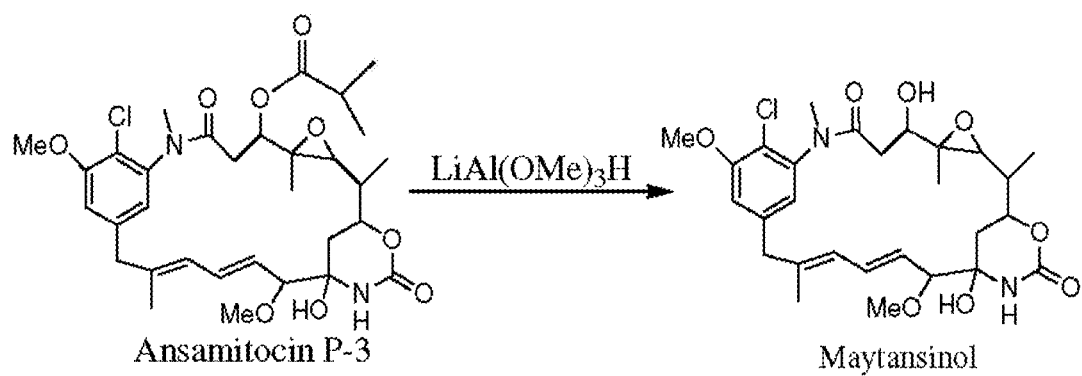
FIG. 3 shows the conversion of ansamitocin P-3 to maytansinol (stereochemistry is omitted for simplicity).

The present invention relates to immunoconjugates comprising CD138 targeting agents and the delivery of the effector molecule(s) of the immunoconjugates to target sites and the site specific release of effector(s) molecule in, at or near target cells, tissues and organs. The effector molecules may be activated by cleavage/dissociation from the targeting agent portion of the immunoconjugate at the target site. The present invention is in particular related to the use of these immunoconjugates in combating tumor growth in vivo and to the use of the ability of these immunoconjugates to overcome or diminish protective mechanisms encountered in the bone marrow microenvironment.

The immunoconjugates according to the present invention may be administered to a subject in need of therapeutic treatment or to cells isolated from such a subject in need of therapeutic treatment. The effector molecule or molecules may be released from the immunoconjugate by cleavage/dissociation in, at or close to the target cell, tissue or organ.

In one example, the immunoconjugate comprises the antibody nBT062, which targets CD138 expressing cells, and at least one highly cytotoxic drug or toxin as an effector molecule, is administered to a patient with cancer. In this example, a therapeutically effective amount of the immunoconjugate is administered intravenously to a patient so that it concentrates in the cancer cells. The effector molecule or molecules are then released from the antibody by natural means. After or during cleavage the effector molecule may be stabilized by alkylation and may diffuse to surrounding auxiliary cells such as stroma cells that do not express CD138.

In a second example, the immunoconjugate comprises the antibody nBT062, which targets CD138 expressing cells, and at least one highly cytotoxic drug or toxin as an effector molecule, and an additional cytotoxic agent is administered to a patient with cancer. In this example, a therapeutically effective amount of the immunoconjugate and the cytotoxic agent are administered consecutively. First the immunoconjugate is administered intravenously to a patient so that it concentrates in the cancer cells in the bone marrow microenvironment. The immunoconjugate substantially overcomes cell adhesion mediated drug resistance (CAM-DR) and destroys a substantial portion of the CD138 expressing tumor cells in the bone marrow microenvironment. In particular, the effector molecule(s) are released from the antibody by natural means and destroy tumor cells. The immunoconjugate at least in part prevents adhesion of the tumor cells to the stroma cells, some of which may be destroyed by diffusing effector molecule. After a time interval of 12 hours, the cytotoxic agent is administered. The cytotoxic agent, whose activity is normally at least reduced by CAM-DR can act on tumor cells that are not associated with stroma cells and destroys CD138 expressing tumor cells, which escaped action by the immunoconjugate.

CD138 or syndecan-1 (also described as SYND1; SYNDECAN; SDC; SCD1; CD138 ANTIGEN, SwissProt accession number: P18827 human) is a membrane glycoprotein that was originally described to be present on cells of epithelial origin, and subsequently found on hematopoietic cells (Sanderson, 1989). CD138 has a long extracellular domain that binds to soluble molecules (e.g., the growth factors EGF, FGF, HGF) and to insoluble molecules (e.g., to the extracellular matrix components collagen and fibronectin) through heparan sulfate chains (Langford, 1998; Yang, 2007) and acts as a receptor for the extracellular matrix. CD138 also mediates cell to cell adhesion through heparin-binding molecules expressed by adherent cells. It has been shown that CD138 has a role as a co-receptor for growth factors of myeloma cells (Bisping, 2006). Studies of plasma cell differentiation showed that CD138 must also be considered as a differentiation antigen (Bataille, 2006).

In malignant hematopoiesis, CD138 is highly expressed on the majority of MM cells, ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), solid tissue sarcomas, colon carcinomas as well as other hematologic malignancies and solid tumors that express CD138 (Carbone et al., 1999; Sebestyen et al., 1999; Han et al., 2004; Charnaux et al., 2004; O'Connell et al., 2004; Orosz and Kopper, 2001).

Other cancers that have been shown to be positive for CD138 expression are many ovarian adenocarcinomas, transitional cell bladder carcinomas, kidney clear cell carcinomas, squamous cell lung carcinomas; breast carcinomas and uterine cancers (see, for example, Davies et al., 2004; Barbareschi et al., 2003; Mennerich et al., 2004; Anttonen et al., 2001; Wijdenes, 2002).

In the normal human hematopoietic compartment, CD138 expression is restricted to plasma cells (Wijdenes, 1996; Chilosi, 1999) and CD138 is not expressed on peripheral blood lymphocytes, monocytes, granulocytes, and red blood cells. In particular, $CD34^+$ stem and progenitor cells do not express CD138 and anti-CD138 mAbs do not affect the number of colony forming units in hematopoietic stem cell cultures (Wijdenes, 1996). In non-hematopoietic compartments, CD138 is mainly expressed on simple and stratified epithelia within the lung, liver, skin, kidney and gut. Only a weak staining was seen on endothelial cells (Bernfield, 1992; Vooijs, 1996). It has been reported that CD138 exists in polymorphic forms in human lymphoma cells (Gattei, 1999).

Monoclonal antibodies B-B4, BC/B-B4, B-B2, DL-101, 1 D4, MI15, 1.BB.210, 2Q1484, 5F7, 104-9, 281-2 in particular B-B4 have been reported to be specific to CD138. Of those B-B4, 1D4 and MI15 recognized both the intact molecule and the core protein of CD138 and were shown to recognize either the same or closely related epitopes (Gattei, 1999). Previous studies reported that B-B4 did not recognize soluble CD138, but only CD138 in membrane bound form (Wijdenes, 2002).

B-B4, a murine IgG1 mAb, binds to a linear epitope between residues 90-95 of the core protein on human syndecan-1 (CD138) (Wijdenes, 1996; Dore, 1998). Consistent with the expression pattern of CD138, B-B4 was shown to strongly react with plasma cell line RPMI8226, but not to react with endothelial cells. Also consistent with the expression pattern of CD138, B-B4 also reacted with epithelial cells lines A431 (keratinocyte derived) and HepG2 (hepatocyte derived). An immunotoxin B-B4-saporin was also highly toxic towards the plasma cell line RPMI8226, in fact considerably more toxic than free saporin. However, from the two epithelial cell lines tested, B-B4-saporin showed only toxicity towards cell line A431, although in a clonogenic assay B-B4 saporin showed no inhibitory effect on the outgrowth of A431 cells (Vooijs, 1996). Other researchers reported lack of specificity of MM-associated antigens against tumors (Couturier, 1999).

An antibody/immunoconjugate "consisting essentially of" certain components means in the context of the present invention that the antibody/immunoconjugate consists of the specified components and any additional materials or components that do not materially affect the basic characteristics of the antibody.

The present invention uses the term "tumor cell" to include cancer cells as well as pre-cancerous cells which may or may not form part of a solid tumor.

A "targeting agent" according to the present invention is able to associate with a molecule expressed by a target cell and includes peptides and non-peptides. In particular, targeting agents according to the present invention include targeting antibodies and non-immunoglobulin targeting molecules, which may be based on non-immunoglobulin proteins, including, but not limited to, AFFILIN® molecules, ANTICALINS® and AFFIBODIES®. Non-immunoglobulin targeting molecules also include non-peptidic targeting molecules such as targeting DNA and RNA oligonucleotides (aptamers), but also physiological ligands, in particular ligands of the antigen in question, such as CD138.

A "targeting antibody" according to the present invention is or is based on a natural antibody or is produced synthetically or by genetic engineering and binds to an antigen on a cell or cells (target cell(s)) of interest. A targeting antibody according to the present invention includes a monoclonal antibody, a polyclonal antibody, a multispecific antibody (for example, a bispecific antibody), or an antibody fragment. The targeting antibody may be engineered to, for example, improve its affinity to the target cells (Ross, 2003) or diminish its immunogenicity. The targeting antibody may be attached to a liposomal formulation including effector molecules (Carter, 2003). An antibody fragment comprises a portion of an intact antibody, preferably the antigen binding or variable region of the intact antibody. Examples of antibody fragments according to the present invention include Fab, Fab', F(ab')$_2$, and Fv fragments, but also diabodies; domain antibodies (dAb) (Ward, 1989; U.S. Pat. No. 6,005,079); linear antibodies; single-chain antibody molecules; and multispecific antibodies formed from antibody fragments. In a single chain variable fragment antibody (scFv) the heavy and light chains (VH and VL) can be linked by a short amino acid linker having, for example, the sequence (glycine$_4$serine)$_n$, which has sufficient flexibility to allow the two domains to assemble a functional antigen binding pocket. Addition of various signal sequences may allow for more precise targeting of the targeting antibody. Addition of the light chain constant region (CL) may allow dimerization via disulphide bonds, giving increased stability and avidity. Variable regions for constructing the scFv can, if a mAb against a target of interest is available, be obtained by RT-PCR which clones out the variable regions from mRNA extracted from the parent hybridoma. Alternatively, the scFv can be generated de novo by phage display technology (Smith, 2001). As used herein, the term "functional fragment", when used in reference to a targeting antibody, is intended to refer to a portion of the targeting antibody which is capable of specifically binding an antigen that is specifically bound by the antibody reference is made to. A bispecific antibody according to the present invention may, for example, have at least one arm that is reactive against a target tissue and one arm that is reactive against a linker moiety (United States Patent Publication 20020006379). A bispecific antibody according to the present invention may also bind to more than one antigen on a target cell (Carter, 2003). An antibody according to the present invention may be modified by, for example, introducing cystein residues to introduce thiol groups (Olafsen, 2004).

In accordance with the present invention, the targeting antibody may be derived from any source and may be, but is not limited to, a camel antibody, a murine antibody, a chimeric human/mouse antibody or a chimeric human/monkey antibody, in particular, a chimeric human/mouse antibody such as nBT062.

Humanized antibodies are antibodies that contain sequences derived from a human-antibody and from a non-human antibody and are also within the scope of the present invention. Suitable methods for humanizing antibodies include CDR-grafting (complementarity determining region grafting) (EP 0 239 400; WO 91/09967; U.S. Pat. Nos. 5,530,101; and 5,585,089), veneering or resurfacing (EP 0 592 106; EP 0 519 596; Padlan, 199; Studnicka et al., 1994; Roguska et al., 1994), chain shuffling (U.S. Pat. No. 5,565,332) and DeImmunosation™ (Biovation, LTD). In CDR-grafting, the mouse complementarity-determining regions (CDRs) from, for example, mAb B-B4 are grafted into human variable frameworks, which are then joined to human constant regions, to create a human B-B4 antibody (hB-B4). Several antibodies humanized by CDR-grafting are now in clinical use, including MYLOTARG (Sievers et al., 2001) and HECEPTIN (Pegram et al, 1998).

The resurfacing technology uses a combination of molecular modeling, statistical analysis and mutagenesis to alter the non-CDR surfaces of antibody variable regions to resemble the surfaces of known antibodies of the target host. Strategies and methods for the resurfacing of antibodies, and other methods for reducing immunogenicity of antibodies within a different host, are disclosed, for example, in U.S. Pat. No. 5,639,641. Human antibodies can be made by a variety of methods known in the art including phage display methods. See also U.S. Pat. Nos. 4,444,887, 4,716,111, 5,545,806, and 5,814,318; and international patent application publications WO 98/46645, WO 98/50433, WO 98/24893, WO 98/16654, WO 96/34096, WO 96/33735, and WO 91/10741.

Targeting antibodies that have undergone any non-natural modification such as chimeric human/mouse antibodies or a chimeric human/monkey antibodies, humanized antibodies or antibodies that were engineered to, for example, improve their affinity to the target cells or diminish their immunogenicity but also antibody fragments, in particular functional fragments of such targeting antibodies that have undergone any non-natural modification, diabodies; domain antibodies; linear antibodies; single-chain antibody molecules; and multispecific antibodies are referred to herein as engineered targeting antibodies.

Chimerized antibodies, maintain the antibody binding region (ABR or Fab region) of the non-human antibody, e.g., the murine antibody they are based on, while any constant regions may be provided for by, e.g., a human antibody. Generally, chimerization and/or the exchange of constant regions of an antibody will not affect the affinity of an antibody because the regions of the antibody which contribute to antigen binding are not affected by this exchange. In a preferred embodiment of the present invention, the engineered, in particular chimerized, antibody of the present invention, may have a higher binding affinity (as expressed by $K_D$ values) than the respective non-human antibody it is based on. In particular, the nBT062 antibody and antibodies based thereon may have higher antibody affinity than the murine B-B4. In another preferred embodiment of the present invention, immunoconjugates comprising those engineered/chimerized antibodies also display this higher antibody affinity. These immunoconjugates may also display in certain embodiments other advantageous properties, such as a higher reduction of tumor load than their B-B4 containing counterparts. In a preferred embodiment, the engineered, in particular chimerized targeting antibodies display binding affinities that are characterized by dissociation constants $K_D$ (nM) of less than 1.6, less than 1.5 or about or less than 1.4, while their murine counterparts are characterized by dissociation constants $K_D$ (nM) of about or more than 1.6. Immunoconjugates comprising targeting agents such as targeting antibodies may be characterized by dissociation constants of $K_D$ (nM) of less than 2.6, less than 2.5, less than 2.4, less than 2.3, less than 2.2, less than 2.1, less than 2.0, less than or about 1.9 are preferred, while immunoconjugates comprising the murine counterpart antibodies may be characterized by dissociation constants $K_D$ (nM) of about or more than 2.6 (compare Table 3, Materials and Methods).

Fully human antibodies may also be used. Those antibodies can be selected by the phage display approach, where CD138 or an antigenic determinant thereof is used to selectively bind phage expressing, for example, B-B4 variable regions (see, Krebs, 2001). This approach is advantageously coupled with an affinity maturation technique to improve the affinity of the antibody. All antibodies referred to herein are isolated antibodies.

In one embodiment, the targeting antibody is, in its unconjugated form, moderately or poorly internalized. Moderate internalization constitutes about 30% to about 75% internalization of antibody, poor internalization constitutes about 0.01% to up to about 30% internalization after 3 hours incubation at 37° C. In another preferred embodiment the targeting antibody binds to CD138, for example, antibodies B-B4, BC/B-B4, B-B2, DL-101, 1 D4, MI15, 1.BB.210, 2Q1484, 5F7, 104-9, 281-2 in particular B-B4. Hybridoma cells, which were generated by hybridizing SP02/0 myeloma cells with spleen cells of Balb/c mice have been deposited with the DSMZ-Deutsche Sammlung von Mikroorganismen und Zellkulturen GmbH, Mascheroder Weg 1, D-38124 Braunschweig on Dec. 11, 2007. The identification number of these B-B4 expressing hybridoma cells is DSM ACC2874. In another embodiment, the targeting antibody does not substantially bind non-cell-surface expressed CD138. When, in the context of the present invention, the name of a specific antibody is combined with the term "targeting antibody" such as "nBT062 targeting antibody," this means that this targeting antibody has the binding specificity of the antibody nBT062. If a targeting antibody is said to be "based on" a specified antibody, this means that this targeting antibody has the binding specificity of this antibody, but might take any form consistent with the above description of a targeting antibody. When, in the context of the present invention, the name of a specific antigen is combined with the term "targeting antibody" such as "CD138 targeting antibody," this means that this targeting antibody has the binding specificity for CD138. If, in the context of the present invention, for example, a targeting antibody is said to do something "selectively" such as "selectively targeting cell-surface expressed CD138" or, to be "selective" for something, this means that there is a significant selectivity (i.e. a higher affinity towards CD138-positive cells compared with CD138-negative cells) for, in the case of the example provided, cell-surface expressed CD138, compared to any other antigens. Adverse side effects in a given environment are substantially reduced or even avoided due to this selectivity.

"Non-immunoglobulin targeting molecules" according to the present invention include targeting molecules derived from non-immunoglobulin proteins as well as non-peptidic targeting molecules. Small non-immunoglobulin proteins which are included in this definition are designed to have specific affinities towards, in particular surface expressed CD138. These small non-immunoglobulin proteins include scaffold based engineered molecules such as Affilin® molecules that have a relatively low molecular weight such as between 10 kDa and 20 kDa. Appropriate scaffolds include, for example, gamma crystalline. Those molecules have, in their natural state, no specific binding activity towards the target molecules. By engineering the protein surfaces through locally defined randomization of solvent exposed amino acids, completely new binding sites are created. Former non-binding proteins are thereby transformed into specific binding proteins. Such molecules can be specifically designed to bind a target, such as CD138, and allow for specific delivery of one or more effector molecules (see, scil Proteins GmbH website, 2004). Another kind of non-immunoglobulin targeting molecules are derived from lipocalins, and include, for example ANTICALINS®, which resemble in structure somewhat immunoglobulins. However, lipocalins are composed of a single polypeptide chain with 160 to 180 amino acid residues. The binding pocket of lipocalins can be reshaped to recognize a molecule of interest with high affinity and specificity (see, for example, Beste et al., 1999). Artificial bacterial receptors such as those marketed under the trademark Affibody® (Affibody AB) are also within the scope of the present invention. These artificial bacterial receptor molecules are small, simple proteins and may be composed of a three-helix bundle based on the scaffold of one of the IgG-binding domains of Protein A (*Staphylococcus aureus*). These molecules have binding properties similar to many immunoglobulins, but are substantially smaller, having a molecular weight often not exceeding 10 kDa and are also comparatively stable. Suitable artificial bacterial receptor molecules are, for example, described in U.S. Pat. Nos. 5,831,012; 6,534,628 and 6,740,734.

Other "non-immunoglobulin targeting molecules" are physiological ligands of the antigen in question. Physiological ligands of CD138 include for example, but not limited to, ADAMTS4 (aggrecanase-1), antithrombin-3, bFGF, cathepsin G, CCL5 (RANTES), CCL7, CCL11, CCL17, CD44, collagens (collagen type 1, collagen type 2, collagen type 3, collagen type 4, collagen type 5, collagen type 6), CXCL1, elastase, gp120, HGF [hepatocyte growth factor], laminin-1, laminin-2, laminin-5, midkine, MMP-7, neutrophil elastase, and pleiotrophin (HBNF, HBGF-8). Non-peptidic targeting molecules include, but are not limited to, to DNA and RNA oligonucleotides that bind to CD138 (aptamers).

An "effector molecule" according to the present invention is a molecule or a derivative, or an analogue thereof that is attached to a targeting agent, in particular a targeting antibody and/or an engineered targeting antibody, and that exerts a desired effect, for example, apoptosis, or another type of cell death, or a continuous cell cycle arrest on the target cell or cells. Effector molecules according to the present invention include molecules that can exert desired effects in a target cell and include, but are not limited to, toxins, drugs, in particular low molecular weight cytotoxic drugs, radionuclides, biological response modifiers, pore-forming agents, ribonucleases, proteins of apoptotic signaling cascades with apoptosis-inducing activities, cytotoxic enzymes, prodrug activating enzymes, antisense oligonucleotides, antibodies or cytokines as well as functional derivatives or analogues/fragments thereof. Toxins may include bacterial toxins, such as, but not limited to, Diphtheria toxin or Exotoxin A, plant toxins, such as but not limited to, Ricin. Proteins of apoptotic signaling cascades with apoptosis-inducing activities, include, but are not limited to, Granzyme B, Granzyme A, Caspase-3, Caspase-7, Caspase-8, Caspase-9, truncated Bid (tBid), Bax and Bak.

In a preferred embodiment, the effector increases internal effector delivery of the immunoconjugate, in particular when the natural form of the antibody on which the targeting antibody of the immunoconjugate is based is poorly internalizable. In another preferred embodiment the effector is, in its native form, non-selective. In certain embodiments the effector has high non-selective toxicity, including systemic toxicity, when in its native form. The "native form" of an effector molecule of the present invention is an effector molecule before being attached to the targeting agent to form an immunoconjugate. In another preferred embodiment, the non-selective toxicity of the effector molecule is substantially eliminated upon conjugation to the targeting agent. In another preferred embodiment, the effector molecule causes, upon reaching the target cell, death or continuous cell cycle arrest in the target cell. A drug-effector molecule according to the present invention includes, but is not limited to, a drug including, for example, small highly cytotoxic drugs that act as inhibitors of tubulin polymerization such as maytansinoids, dolastatins, auristatin and crytophycin; DNA alkylating agents like CC-1065 analogues or derivatives (U.S. Pat. Nos. 5,475,092; 5,585,499; 6,716,821) and duocarmycin; enediyne antibiotics such as calicheamicin and esperamicin; and potent taxoid (taxane) drugs (Payne, 2003). Maytansinoids and calicheamicins are particularly preferred. An effector maytansinoid includes maytansinoids of any origin, including, but not limited to synthetic maytansinol and maytansinol analogue and derivative. Doxorubicin, daunomycin, methotrexate, vinblastine, neocarzinostatin, macromycin, trenimon and a-amanitin are some other effector molecules within the scope of the present invention. Also within the scope of the present invention are antisense DNA molecules as effector molecules. When the name of, for example, a specific drug or class of drugs is combined herein with the term "effector" or "effector molecule," reference is made to an effector of an immunoconjugate according to the present invention that is based on the specified drug or class of drugs.

Maytansine is a natural product originally derived from the Ethiopian shrub Maytenus serrata (Remillard, 1975; U.S. Pat. No. 3,896,111). This drug inhibits tubulin polymerization, resulting in mitotic block and cell death (Remillard, 1975; Bhattacharyya, 1977; Kupchan, 1978). The cytotoxicity of maytansine is 200-1000-fold higher than that of anti-cancer drugs in clinical use that affect tubulin polymerization, such as Vinca alkaloids or taxol. However, clinical trials of maytansine indicated that it lacked a therapeutic window due to its high systemic toxicity. Maytansine and maytansinoids are highly cytotoxic but their clinical use in cancer therapy has been greatly limited by their severe systemic side-effects primarily attributed to their poor selectivity for tumors. Clinical trials with maytansine showed serious adverse effects on the central nervous system and gastrointestinal system.

Maytansinoids have also been isolated from other plants including seed tissue of Trewia nudiflora (U.S. Pat. No. 4,418,064)

Certain microbes also produce maytansinoids, such as maytansinol and C-3 maytansinol esters (U.S. Pat. No. 4,151,042).

The present invention is directed to maytansinoids of any origin, including synthetic maytansinol and maytansinol analogues which are disclosed, for example, in U.S. Pat. Nos. 4,137,230; 4,248,870; 4,256,746; 4,260,608; 4,265, 814; 4,294,757; 4,307,016; 4,308,268; 4,308,269; 4,309, 428; 4,313,946; 4,315,929; 4,317,821; 4,322,348; 4,331,598; 4,361,650; 4,362,663; 4,364,866; 4,371,533; 4,424,219 and 4,151,042.

In a preferred embodiment, the maytansinoid is a thiol-containing maytansinoid and is more preferably produced according to the processes disclosed in U.S. Pat. No. 6,333,410 to Chari et al or in Chari et al. (Chari, 1992).

DM-1 ($N^2$-deacetyl-$N^2$-(3-mercapto-1-oxopropyl)-maytansine) is a preferred effector molecule in the context of the present invention. DM1 is 3- to 10-fold more cytotoxic than maytansine, and has been converted into a pro-drug by linking it via disulfide bond(s) to a monoclonal antibody directed towards a tumor-associated antigen. Certain of these conjugates (sometimes called "tumor activated prodrugs" (TAPs)) are not cytotoxic in the blood compartment, since they are activated upon associating with a target cells and internalized, thereby releasing the drug (Blättler, 2001). Several antibody-DM1 conjugates have been developed (Payne, 2003), and been evaluated in clinical trials. For example, huC242-DM1 treatment in colorectal cancer patients was well tolerated, did not induce any detectable immune response, and had a long circulation time (Tolcher, 2003).

Figure 4:
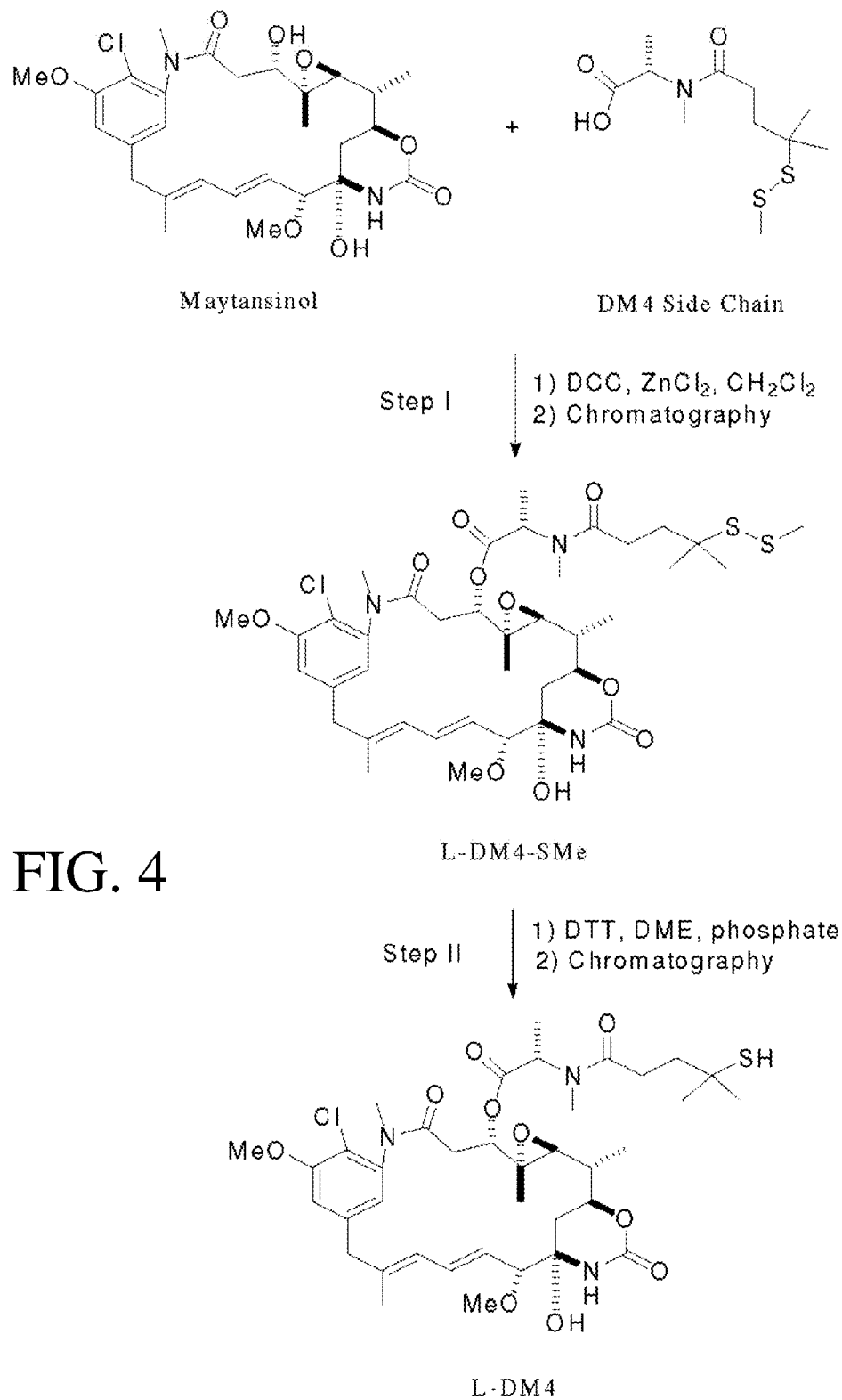
FIG. 4 shows a representative synthesis scheme of DM4.

Other particularly preferred maytansinoids comprise a side chain that contains a sterically hindered thiol bond such as, but not limited to, maytansinoids $N^{2'}$-deacetyl-$N^{2'}$-(4-mercapto-1-oxopentyl)-maytansine, also referred to as "DM3," and $N^{2'}$-deacetyl-$N^{2'}$-(4-methyl-4-mercapto-1-oxopentyl)-maytansine, also referred to as "DM4." The synthesis of DM4 is shown in FIGS. 3 and 4 and is described elsewhere herein. DM4 differs from DM1 and DM3 in that it bears methyl groups at its aC. This results in a sterical hindrance when DM4 is attached via a linker in particular, but not limited to, a linker comprising a disulfide bond, to a targeting agent such as nBT062. A wide variety of maytansinoids bearing a sterically hindered thiol group (possessing one or two substituents, in particular alkyls substituents, such as the methyl substituents of DM4) are disclosed U.S. Patent Publication 2004/0235840, published Nov. 25, 2004, which is incorporated herein in its entirety by reference. The steric hindrance conferred by alkyl groups such as the methyl groups on the carbon adjacent to the sulfur atom of DM3 and DM4 may affect the rate of intracellular cleavage of the immunoconjugate. The variable alkyl unit may therefore affect potency, efficacy, and safety/toxicity in vitro and in vivo.

As reported by Goldmahker et al. in U.S. Patent Publication 2006/0233814, such a hindrance induces alkylation (e.g., methylation) of the free drug, once the drug is released at its target. The alkylation may increase the stability of the drug allowing for the so-called bystander effect. However, as the person skilled in the art will appreciate, other effector molecules comprising substitutents such as alkyl groups at positions that result in a sterical hindrance when the effector is attached to a targeting agent via a linker are part of the present invention (U.S. Patent Publication 2004/0235840). Preferably this hindrance induces a chemical modification such as alkylation of the free drug to increase its overall stability, which allows the drug to not only induce cell death or continuous cell cycle arrest in CD138 expressing tumor cells but, optionally, also to affect auxiliary cells that, e.g., support or protect the tumor from drugs, in particular cells of the tumor stroma and the tumor vasculature and which generally do not express CD138 to diminish or lose their supporting or protecting function.

DNA alkylating agents are also particularly preferred as effector molecules and include, but are not limited to, CC-1065 analogues or derivatives. CC-1065 is a potent antitumor-antibiotic isolated from cultures of *Streptomyces zelensis* and has been shown to be exceptionally cytotoxic in vitro (U.S. Pat. No. 4,169,888). Within the scope of the present invention are, for example the CC-1065 analogues or derivatives described in U.S. Pat. Nos. 5,475,092, 5,585,499 and 5,739,350. As the person skilled in the art will readily appreciate, modified CC-1065 analogues or derivatives as described in U.S. Pat. No. 5,846,545 and prodrugs of CC-1065 analogues or derivatives as described, for example, in U.S. Pat. No. 6,756,397 are also within the scope of the present invention. In certain embodiments of the invention, CC-1065 analogues or derivatives may, for example, be synthesized as described in U.S. Pat. No. 6,534,660.

Another group of compounds that make preferred effector molecules are taxanes, especially highly potent ones and those that contain thiol or disulfide groups. Taxanes are mitotic spindle poisons that inhibit the depolymerization of tubulin, resulting in an increase in the rate of microtubule assembly and cell death. Taxanes that are within the scope of the present invention are, for example, disclosed in U.S. Pat. Nos. 6,436,931; 6,340,701; 6,706,708 and United States Patent Publications 20040087649; 20040024049 and 20030004210. Other taxanes are disclosed, for example, in U.S. Pat. Nos. 6,002,023, 5,998,656, 5,892,063, 5,763,477, 5,705,508, 5,703,247 and 5,367,086. As the person skilled in the art will appreciate, PEGylated taxanes such as the ones described in U.S. Pat. No. 6,596,757 are also within the scope of the present invention.

Calicheamicin effector molecules according to the present invention include gamma 1l, N-acetyl calicheamicin and other derivatives of calicheamicin. Calicheamicin binds in a sequence-specific manner to the minor groove of DNA, undergoes rearrangement and exposes free radicals, leading to breakage of double-stranded DNA, resulting in cell apoptosis and death. One example of a calicheamicin effector molecule that can be used in the context of the present invention is described in U.S. Pat. No. 5,053,394.

An immunoconjugate according to the present invention comprises at least one targeting agent, in particular targeting antibody and one effector molecule. The immunoconjugate might comprise further molecules for example for stabilization. For immunoconjugates, the term "conjugate" is generally used to define the operative association of the targeting agent with one or more effector molecules and is not intended to refer solely to any type of operative association, and is particularly not limited to chemical "conjugation". So long as the targeting agent is able to bind to the target site and the attached effector functions sufficiently as intended, particularly when delivered to the target site, any mode of attachment will be suitable. The conjugation methods according to the present invention include, but are not limited to, direct attachment of the effector molecule to the targeting antibody, with or without prior modification of the effector molecule and/or the targeting antibody or attachment via linkers. Linkers can be categorized functionally into, for example, acid labile, photolabile linkers, enzyme cleavable linkers, such as linkers that can be cleaved by peptidases. Cleavable linkers are, in many embodiments of the invention preferred. Such cleavable linkers can be cleaved under conditions present in the cellular environment, in particular, an intracellular environment and that have no detrimental effect on the drug released upon cleavage. Low pHs such as pH of 4 to 5 as they exist in certain intracellular departments will cleave acid labile linkers, while photolabile linkers can be cleaved by, e.g., infrared light. However, linkers that are cleaved by/under physiological conditions present in the majority of cells are preferred and are referred to herein as physiologically cleavable linkers. Accordingly, disulfide linkers are being preferred in many embodiments of the invention. These linkers are cleavable through disulfide exchange, which can occur under physiological conditions. Preferred heterobifunctional disulfide linkers include, but are not limited to, N-succinimidyl 3-(2-pyridyldithio)propionate (SPDP) (see, e.g., Carlsson et al. (1978)), N-succinimidyl 4-(2-pyridyldithio) butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., (1979)), and N-succinimidyl 4-methyl-4-[2-(5-nitro-pyridyl)-dithio]pentanoate (SMNP) (see, e.g., U.S. Pat. No. 4,563,304). The most preferred linker molecules for use in the inventive composition are SPP, SMCC, and SPDB.

Other suitable linkers may include "non-cleavable" bonds, such as, but not limited to Sulfosuccinimidyl maleimidomethyl cyclohexane carboxylate (SMCC), which is a heterobifunctional linker capable of linking compounds with SH-containing compounds. Bifunctional and heterobifunctional linker molecules, such as carbohydrate-directed heterobifunctional linker molecules, such as S-(2-thiopyridyl)-L-cysteine hydrazide (TPCH), are also within the scope of the present invention (Vogel, 2004). The effector molecule, such as a maytansinoid, may be conjugated to the targeting antibody via a two reaction step process, including as a first step modification of the targeting antibody with a cross-linking reagent such as N-succinimidyl pyridyldithiopropionate (SPDP) to introduce dithiopyridyl groups into the targeting antibody. In a second step, a reactive maytansinoid having a thiol group, such as DM1, may be added to the modified antibody, resulting in the displacement of the thiopyridyl groups in the modified antibody, and the production of disulfide-linked cytotoxic maytansinoid/antibody conjugate (U.S. Pat. No. 5,208,020). However, one-step conjugation processes such as the one disclosed in United States Patent Publication 20030055226 to Chari et al are also within the scope of the present invention. In one embodiment of the present invention multiple effector molecules of the same or different kind are attached to a targeting antibody. As discussed elsewhere herein, the nature of the linkers employed may influence bystander killing (Kovtun et al., 2006). See also discussion of FIG. 13.

CC-1065 analogues or derivatives may be conjugated to the targeting agent via for example PEG linking groups as described in U.S. Pat. No. 6,716,821.

Calicheamicins may be conjugated to the targeting antibodies via linkers (U.S. Pat. Nos. 5,877,296 and 5,773,001) or according to the conjugation methods disclosed in U.S. Pat. Nos. 5,712,374 and 5,714,586. Another preferred method for preparing calicheamicin conjugates is disclosed in Unites States Patent Publication 20040082764. The immunoconjugates of the present invention may take the form of recombinant fusion proteins.

The term "cytotoxic agents" comprises "cytotoxic/cancer drugs" including chemotherapeutic agents such as melphalan, cyclophosphamide, vincristine, doxorubicin and liposomal doxorubicin (DOXIL), cyclophosphamide, etoposide, cytarabine and cisplatin, corticosteroids such as prednisone and dexamethasone and agents such as thalidomide, bortezomib, lenalidomide, but also kinase inhibitor such as sorafenib or HDAC (histone deacetylase) inhibitors such as romidepsin as well as growth inhibitory agents, anti-hormonal agents, anti-angiogenic agents, cardioprotectants, immunostimulatory agents, immunosuppressive agents, angiogenesis inhibitors, protein tyrosine kinase (PTK) inhibitors. Also included in this definition are antibody based cytotoxic agents including immunoconjugates and antibodies that have an art recognized cytotoxic effect. Anti-CD40 is a preferred antibody. Other antibodies include, but are not limited to, e.g., AVASTIN (bevacizuab) or MYELOMACIDE (milatuzumab).

THALOMID (α-(N-phthalimido) glutarimide; thaliomide), is an immunomodulatory agent. The empirical formula for thalidomide is $C_{13}H_{10}N_2O_4$ and the gram molecular weight is 258.2. The CAS number of thalidomide is 50-35-1. It appears to have multiple actions, including the ability to inhibit the growth and survival of myeloma cells in various ways and to inhibit the growth of new blood vessels.

VELCADE is a proteasome inhibitor used to treat multiple myeloma. It is believed that VELCADE acts on myeloma cells to cause cell death, and/or acts indirectly to inhibit myeloma cell growth and survival by acting on the bone microenvironment. Without being limited to a specific theory or mode of action, VELCADE thus disrupts normal cellular processes, resulting in proteasome inhibition that promotes apoptosis.

REVLIMID is an immunomodulatory agent. It is thought that REVLIMID affects multiple pathways in myeloma cells, thereby inducing apoptosis, inhibiting myeloma cell growth, inhibiting vascular endothelial growth factor (VEGF) thereby inhibiting angiogenesis, and reducing adhesion of myeloma cells to bone marrow stromal cells.

Dexamethasone is a synthetic glucocorticoid steroid hormone that acts as an anti-inflammatory and immunosuppressant. When administered to cancer patients, dexamethasone can counteract side effects of cancer therapy. Dexamethasone can also be given alone or together with other anticancer agents, including thalidomide, adriamycin or vincristine.

The term "in combination with" is not limited to the administration at exactly the same time. Instead, the term encompassed administration of the immunoconjugate of the present invention and the other regime (e.g. radiotherapy) or agent, in particular the cytotoxic agents referred to above in a sequence and within a time interval such that they may act together to provide a benefit that is increased compared to treatment with only either the immunoconjugate of the present invention or, e.g., the other agent or agents. It is preferred that the immunoconjugate and the other agent or agents act additively, and especially preferred that they act synergistically. Such molecules are suitably provided in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration. As used in the context of the present invention "co-administration" refers to administration at the same time as the immunoconjugate, often in a combined dosage form.

The term "sequence identity" refers to a measure of the identity of nucleotide sequences or amino acid sequences. In general, the sequences are aligned so that the highest order match is obtained. "Identity", per se, has recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, the nBT062 nucleic acid sequence, or a part thereof, can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments.

Whether the amino acid sequence is at least 50%, 60%, 70%, 75%, 80%, 85%, 90%, 95%, 96%, 97%, 98% or 99% identical to, for instance SEQ ID NO:1 or SEQ ID NO:2, or a part thereof, can be determined conventionally using known computer programs such the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences.

When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

If, in the context of the present invention, reference is made to a certain sequence identity with a combination of residues of a particular sequence, this sequence identity relates to the sum of all the residues specified.

The basic antibody molecule is a bifunctional structure wherein the variable regions bind antigen while the remaining constant regions may elicit antigen independent responses. The major classes of antibodies, IgA, IgD, IgE, IgG and IgM, are determined by the constant regions. These classes may be further divided into subclasses (isotypes). For example, the IgG class has four isotypes, namely, IgG1, IgG2, IgG3, and IgG4 which are determined by the constant regions. Of the various human antibody classes, only human IgG1, IgG2, IgG3 and IgM are known to effectively activate the complement system. While the constant regions do not form the antigen binding sites, the arrangement of the constant regions and hinge region may confer segmental flexibility on the molecule which allows it to bind with the antigen.

Different IgG isotypes can bind to Fc receptors on cells such as monocytes, B cells and NK cells, thereby activating the cells to release cytokines. Different isotypes may also activate complement, resulting in local or systemic inflammation. In particular, the different IgG isotypes may bind FcγR to different degrees. FcγRs are a group of surface glycoproteins belonging to the Ig superfamily and expressed mostly on leucocytes. The FcγR glycoproteins are divided into three classes designated FcγRI (CD64), FcγRII (CD32) and FcγRIII (CD16). While IgG1, IgG2 and IgG3 bind strongly to a variety of these classes of FcγR glycoproteins, IgG4 display much weaker binding. In particular, IgG4 is an intermediate binder of FcγRI, which results in relatively low or even no ADCC (antibody dependent cellular cytotoxicity), and does not bind to FcγRIIIA or FcγRIIA. IgG4 is also a weak binder of FcγRIIB, which is an inhibitory receptor. Furthermore, IgG4 mediates only weak or no complement fixation and weak or no complement dependent cytotoxicity (CDC). In the context of the present invention, IgG4 may be specifically employed to prevent Fc-mediated targeting of hepatic FcR as it displays no interaction with FcRγII on LSECs (liver sinusoidal endothelial cells), no or weak interaction with FcRγI-III on Kupffer cells (macrophages) and no interaction with FcRγIII on hepatic NK cells. Certain mutations that further reduce any CDC are also part of the present invention For example IgG4 residues at positions 327, 330 and 331 were shown to reduce ADCC (antibody dependent cellular cytotoxicity) and CDC (Amour, 1999; Shields, 2001). One of more mutations that stabilize the antibody are also part of the present invention (also referred to herein as "stabilizing mutations"). Those mutations include in particular, leucine-to-glutamic acid mutations in the CH2 region of IgG4 and serine-to-proline exchanges in the IgG4 hinge core. These mutations decrease, in certain embodiments of the invention, the amount of half-molecules to less than 10%, less than 5% and preferably less than 2% or 1%. Moreover, the in vivo half life of so stabilized antibodies might be increased several days, including 1, 2, 3, 4 or more than 5 days (Schuurman, 1999).

Targeting agents, including targeting antibodies disclosed herein may also be described or specified in terms of their binding affinity to antigen, in particular to CD138. Preferred binding affinities of targeting agents such as targeting antibodies are characterized by dissociation constants $K_D$ (nM) of less than 1.6, less than 1.5 or about or less than 1.4. For immunoconjugates comprising said targeting agents such as targeting antibodies dissociation constants $K_D$ (nM) of less than 1.6, less than 1.5 or less than 2.5, less than 2.4, less than 2.3, less than 2.2, less than 2.1, less than 2.0, less than or about 1.9 are preferred.

An antigen binding region (ABR) according to the present invention will vary based on the type of targeting antibody or engineered targeting antibody employed. In a naturally occurring antibody and in most chimeric and humanized antibodies, the antigen binding region is made up of a light chain and the first two domains of a heavy chain. However, in a heavy chain antibody devoid of light chains, the antigen binding region will be made up of, e.g., the first two domains of the heavy chain only, while in single chain antibodies (ScFv), which combine in a single polypeptide chain the light and heavy chain variable domains of an antibody molecule, the ABR is provided by only one polypeptide molecule. FAB fragments are usually obtained by papain digestion and have one light chain and part of a heavy chain and thus comprise an ABR with only one antigen combining site. On the other hand, diabodies are small antibody fragments with two antigen-binding regions. In the context of the present invention, however, an antigen binding region of an targeting antibody or engineered targeting antibody is any region that primarily determines the binding specificity of the targeting antibody or engineered targeting antibody.

If an ABR or another targeting antibody region is said to be "of a certain antibody", e.g., a human or non-human antibody, this means in the context of the present invention that the ABR is either identical to a corresponding naturally occurring ABR or is based thereon. An ABR is based on a naturally occurring ABR if it has the binding specificity of the naturally occurring ABR. However, such an ABR may comprise, e.g., point mutations, additions, deletions or post-translational modification such as glycosylation. Such an ABR may in particular have more than 70%, more than 80%, more than 90%, preferably more than 95%, more than 98% or more than 99% sequence identity with the sequence of the naturally occurring ABR.

Homogenous targeting of a targeting agent such as a targeting antibody, but in particular an immunoconjugate comprising the same, in the context of the present invention, is a measure of the variance associated with obtaining the desired result of said targeting with the targeting agent. In certain embodiments of the invention, the desired result is obtained by simple binding to the target. This is, for example, the case in embodiments in which a certain targeting agent provides a shield against subsequent binding. However, the homogeneity of a targeting agent can be readily assessed, e.g., via the efficacy of an immunoconjugate comprising said targeting agent. For example, the efficacy of said immunoconjugate against a tumor antigen such as CD138 that comprises an effector aimed at destroying tumor cells and/or arresting the growth of a tumor can be determined by the degree of growth suppression of a tumor comprising cells expressing the CD138 antigen. Such an immunoconjugate may display a high variance in its efficacy. It may, for example, arrest tumor growth sometimes with high efficacy, but other times with an efficacy that hardly exceeds the efficacy of the control. A low variance in the efficacy of an immunoconjugate, on the other hand, shows that the immunoconjugate and/or targeting agent, respectively, provide the desired result consistently. One way of quantifying the homogeneity of targeting is to calculate the targeting variation. In the context of tumor growth arrested by an immunoconjugate comprising a certain targeting agent, the targeting variation can be calculated by first determining the time for a tumor to reach a predetermined volume, e.g. 300 mm³. Preferably, the predetermined volume is chosen so that any tumor growth before and after reaching said predetermined volume is steadily increasing at about the same rate. After such time has been determined for a group of subjects the mean of these times ($T_m$) in the group of subjects (e.g., SCID mice or another suitable model displaying homogenous tumor growth) is calculated. $T_m$ is then correlated to the observations made in the subject of the group showing the least efficacy in targeting and thus being associated with tumors that need the least time ($T_f$) to reach said predetermined volume, and, on the other hand, the subject in the group showing the highest efficacy in targeting and thus being associated with tumors that need the most time ($T_s$) to reach said predetermined volume by calculating the targeting variation for the predetermined volume according to the following formula:

TARGETING VARIATION [%]=Ts−Tf/Tm×100

In a preferred embodiment, the targeting variation of the immunoconjugate comprising the engineered targeting antibody of the present invention is less than 150%, less than 140%, less than 130%, less than 120%, less than 110%, less than 100%, less than 90%, less than 80%, less than 70%, less than 60%, or less than 50%, and in certain embodiments even less than 45%. Preferably, the targeting variation is between about 10% and about 150%, preferably between about 10% and about 100%, about 10% and about 80%, about 10% and about 70%, about 10% and about 60%, about 10% and about 50%.

The homogenity of targeting can be also quantified by other means such as determining the tumor growth delay. Also, as the person skilled in the art will readily understand tumor volume of a certain size is only one parameter on which basis targeting variation may be determined. Depending on the desired result, other parameters include time (for, e.g., measuring tumor growth delay) or % of binding may be employed. The person skilled in the art can readily determine such other parameters.

Figures 9A, 9B:
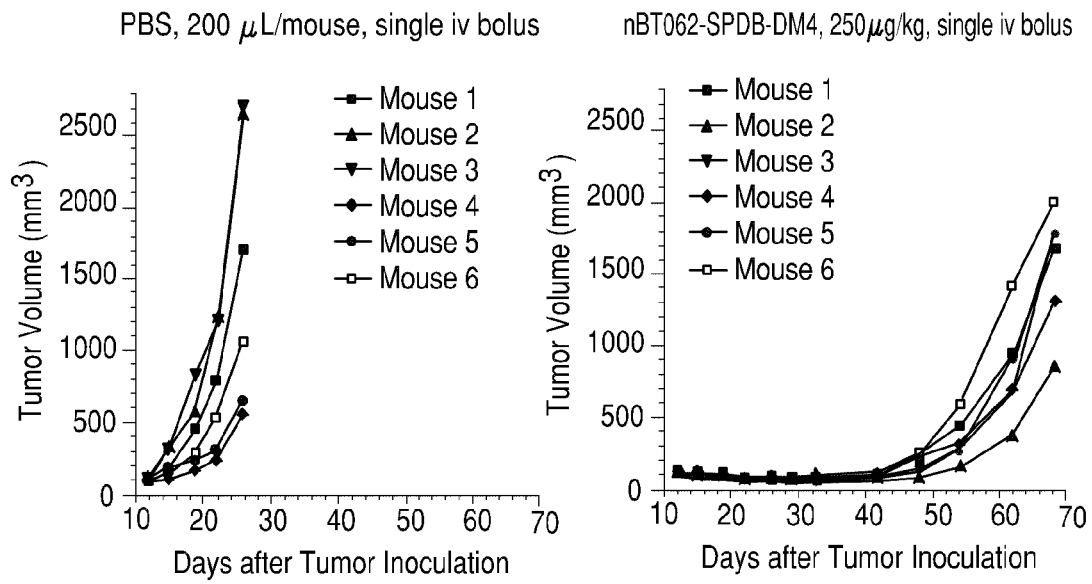
FIG. 9 shows tumor volumes for individual mice treated with (A) PBS, (B) nBT062-SPDB-DM4, (C) B-B4-SPP-DM1 or (D) nBT062-SPP-DM1 over time (days) post-inoculation with MOLP-8 tumor cells.
Figures 9C, 9D:
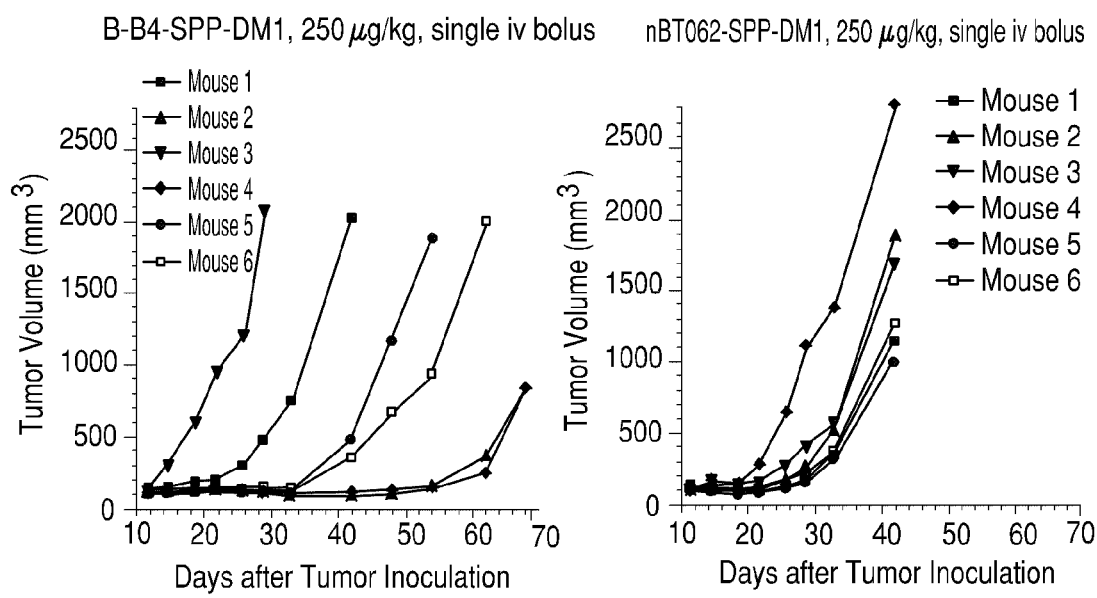

FIG. 9 shows in (C) and (D) the differences in homogenity of targeting/binding between immunoconjugates comprising murine antibody BB4 (BB4-SPP-DM1; FIG. 9C) and the engineered targeting antibody nBT062 (nBT062-SPP-DM1; FIG. 9D) based thereon. As can be seen from these graphs, results obtained with the immunoconjugate comprising the engineered targeting antibody are substantially more homogenous than the ones obtained with the immunoconjugates comprising the murine antibody. This is particularly notable since the antibody binding region of BB4 was not modified in nBT062. Thus, the immunoconjugate comprising the antibody binding region of the murine antibody, but no other parts of the murine antibody, showed properties that far exceeded results the person skilled in the art would have expected.

nBT062 (see also FIG. 1) is a murine human chimeric IgG4 mAb a chimerized version of B-B4. This chimerized version of B-B4 was created to reduce the HAMA (Human Anti-Mouse Antibody) response, while maintaining the functionality of the antibody binding region of the B-B4 for CD138. Surprisingly, the results obtained using an immunoconjugate comprising the engineered targeting antibody were much more homogenous (the variance in the results was reduced). The protocol for producing nBT062 is specified below. Chinese hamster ovary cells expressing nBT062 have been deposited with the DSMZ-Deutsche Sammlung von Mikroorganismen und Zellkulturen GmbH, MascheroderWeg 1, D-38124 Braunschweig on Dec. 11, 2007. The identification number is DSM ACC2875. A CD138 specific chimeric antibody based on B-B4 is generically referred to herein as c-B-B4.

The amino acid sequence for both, the heavy and the light chains has been predicted from the translation of the nucleotide sequence for nBT062. The amino acid sequences predicted for the heavy chain and light chain are presented in Table 1. Predicted variable regions are bolded, predicted CDRs are underlined.

TABLE 1

Predicted Amino Acid Sequence for nBT062

- nBT062 heavy chain predicted sequence (SEQ ID NO:1):

1 QVQLQQSGSE LMMPGASVKI SCKATGYTFS <u>NYWIE</u>WVKQR PGHGLEWIGE

51 <u>ILPGTGRTIY NEKFKGKATF</u> TADISSNTVQ MQLSSLTSED SAVYYCAR<u>RD</u>

101 <u>YYGNFYYAMD Y</u>WGQGTSVTV SSASTKGPSV FPLAPCSRST SESTAALGCL

TABLE 1-continued

```
151 VKDYFPEPVT VSWNSGALTS GVHTFPAVLQ SSGLYSLSSV VTVPSSSLGT

201 KTYTCNVDHK PSNTKVDKRV ESKYGPPCPS CPAPEFLGGP SVFLFPPKPK

251 DTLMISRTPE VTCVVVDVSQ EDPEVQFNWY VDGVEVHNAK TKPREEQFNS

301 TYRVVSVLTV LHQDWLNGKE YKCKVSNKGL PSSIEKTISK AKGQPREPQV

351 YTLPPSQEEM TKNQVSLTCL VKGFYPSDIA VEWESNGQPE NNYKTTPPVL

401 DSDGSFFLYS RLTVDKSRWQ EGNVFSCSVM HEALHNHYTQKSLSLSLG(K)
The C-terminal lysine is prone to clipping and might be
present due to incomplete clipping to a certain extent. The
(K) in parentesis is not part of SEQ ID NO:1.

- nBT062 light chain predicted sequence (SEQ ID NO:2):

1 DIQMTQSTSS LSASLGDRVT ISCSASQGIN NYLNWYQQKP DGTVELLIYY

51 TSTLQSGVPS RFSGSGSGTD YSLTISNLEP EDIGTYYCQQ YSKLPRTFGG

101 GTKLEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC
```

Table 2. shows a comparision of the general CDR definitions of Krabat and Chothia and the predicted CDRs for BT062

| | nBT062 | |
|---|---|---|
| Kabat CDR definition | | |
| Light chain | CDR1: residues 24-34 | CDR1: residues 24-34 |
| | CDR2: residues 50-56 | CDR2: residues 50-56 |
| | CDR3: residues 89-97 | CDR3: residues 89-97 |
| Heavy chain | CDR1: residues 31-35 | CDR1: residues 31-35 |
| | CDR2: residues 50-56 | CDR2: residues 51-68 |
| | CDR3: residues 95-102 | CDR3: residues 99-111 |
| Chothia CDR definition | | |
| Light chain | CDR1: residues 26-32 | CDR1: residues 24-34 |
| | CDR2: residues 50-52 | CDR2: residues 50-56 |
| | CDR3: residues 91-96 | CDR3: residues 89-97 |
| Heavy chain | CDR1: residues 26-32 | CDR1: residues 31-35 |
| | CDR2: residues 52-56 | CDR2: residues 51-68 |
| | CDR3: residues 96-101 | CDR3: residues 99-111 |

BT062 is an immunoconjugate comprising the CD138 targeting chimeric antibody nBT062 that is attached via a linker, here SPDB, to the cytostatic maytansinoid derivative DM4. A chemical representation of BT062 is provided in FIGS. 1 and 2. Immunoconjugates comprising nBT062 and a maytansinoid effector molecule are often characterized in terms of their linker and maytansinoid effector, e.g., nBT062-SMCC-DM1, is an immunoconjugate comprising nBT062, SMCC (a "noncleavable" linker containing a thioester bond) and DM1 as an effector. More generically, an immunoconjugate containing nBT062 and an effector molecule may also be described as nBT062-linker-effector or just as nBT062-effector (nBT062N, wherein N is any effector described herein.

Reference is made herein to a unhindered counterpart (UI: unhindered immunoconjugate) of an immunoconjugate comprising an engineered targeting antibody against CD138 attached to an effector molecule via a cleavable linker (CL) and is described herein as UICL, which is contrasted to an immunoconjugate in which said effector molecule is sterically hindered, and contains a cleavable linker (HICL -hindered immunoconjugate, cleavable linker). The UICL is an immunoconjugate equivalent to the HICL comprising an engineered targeting antibody in which the effector molecule is, however, not sterically hindered. Examples of a pair of HICL/UICL are BT062 and nBT062-SPP-DM1. An unhindered counterpart of such an immunoconjugate comprising a non-cleavable linker (UINCL) refers to the equivalent immunoconjugate comprising an engineered targeting antibody in which the effector molecule is not sterically hindered and comprises a noncleavable linker. For BT062, nBT062-SMCC-DM1 would constitute an example of such an unhindered counterpart comprising an non-cleavable linker (UNICL).

A growth of a tumor inhibiting activity (=tumor growth inhibiting activity) of an immunoconjugate is a relative measure. It describes the tumor growth inhibiting activity of a conjugate relative to the activity of the highest performing immunoconjugate whose activity is set as 100%. For example if the activity of the highest performing immunoconjugate, say, BT062, which causes a tumor growth delay (TGD) of 32 days, is set as 100%, the activity of, e.g., nBT062-DM1, which displays a tumor growth delay (TGD) of 18 days is calculated as follows:

$$\text{Tumor Growth Inhibiting Activity} = 100 \times (TGD_{nBT062-DM1}/TGD_{BT062}),$$

more genericly:

$$\text{Tumor Growth Inhibiting Activity} = 100 \times (TGD_{Sample}/TGD_{Reference}).$$

Figure 11A:
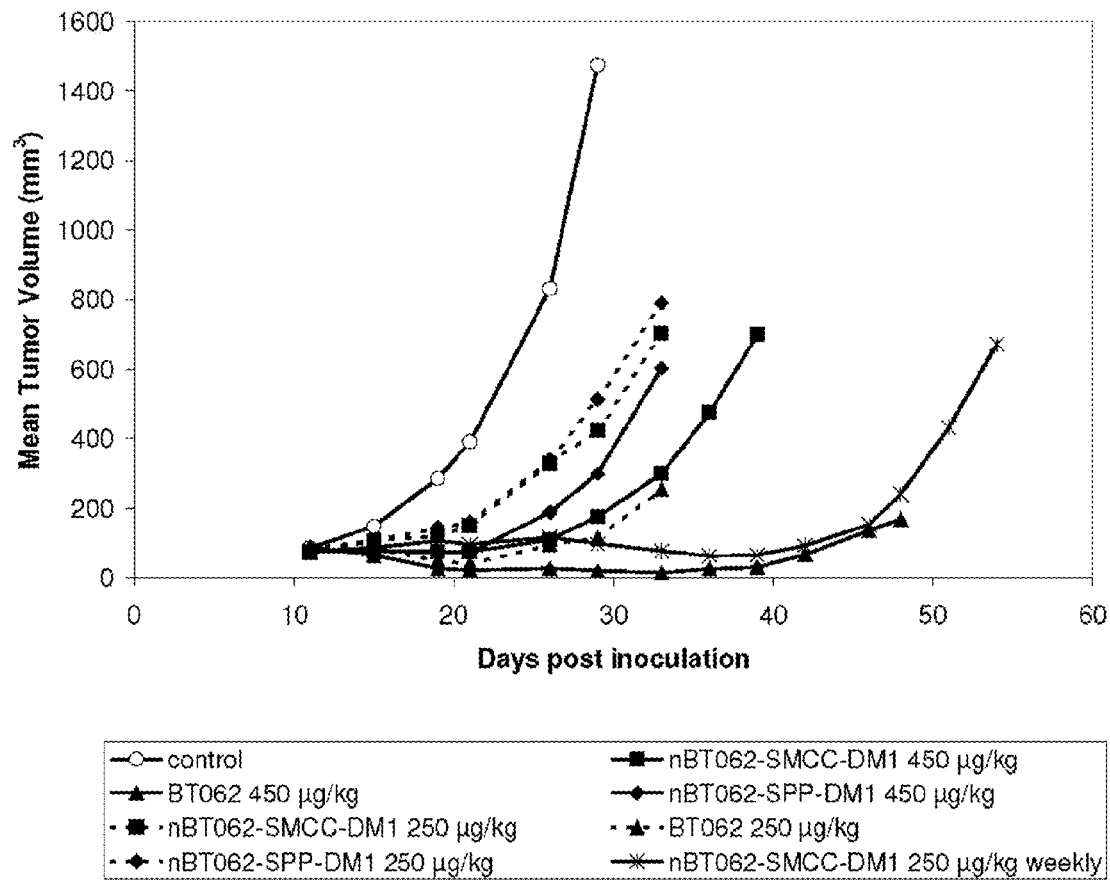
FIGS. 11A and B show the anti-tumor activity of nBT062-DMx against CD138$^+$MOLP-8 tumor cells in a bulky MOLP-8 tumor model in SCID mice. Tumor volume is given as mean (+/−SD) for each group.
Figure 11B:
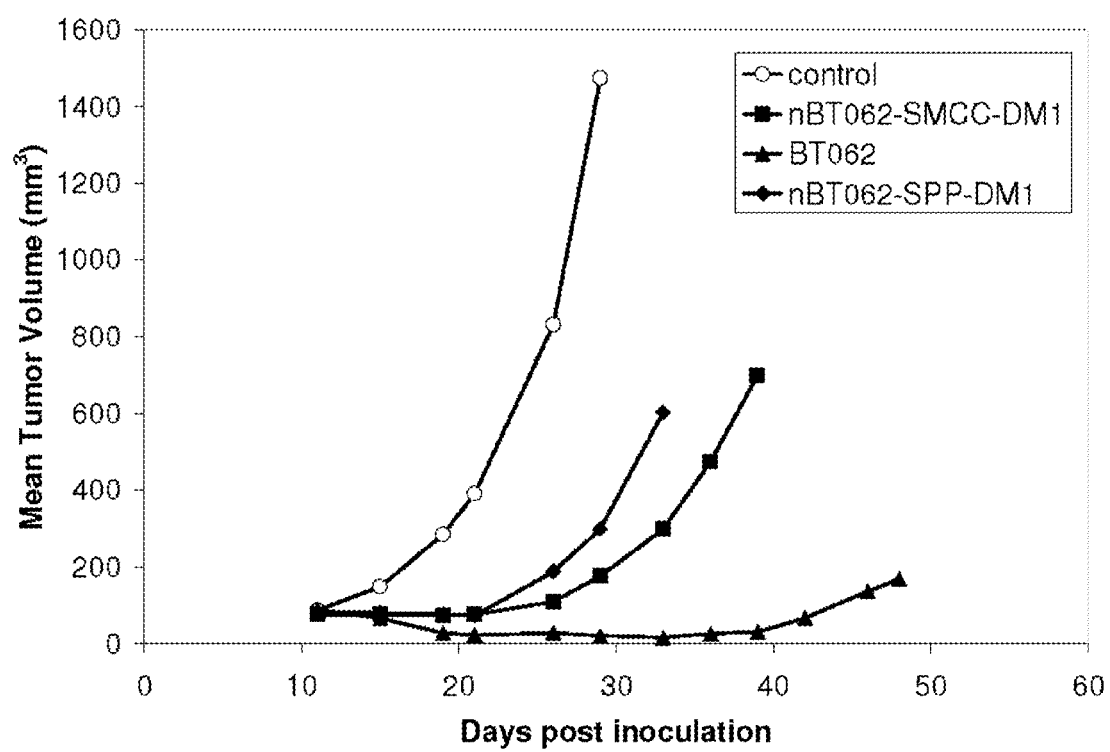

Table 3 provides suitable examples from the results depicted in FIG. 11B:

TABLE 3

Tumor growth delay (TGD) and % Activity of nBT062-DMx against MOLP-8 tumor xenografts in SCID mice based on treatment groups receiving a 450 µg/kg dose.

| | TGD* (days) | % Activity** |
|---|---|---|
| PBS | 0 | 0 |
| nBT062-SMCC-DM1 | 18 | 56 |

TABLE 3-continued

Tumor growth delay (TGD) and % Activity of nBT062-DMx against MOLP-8 tumor xenografts in SCID mice based on treatment groups receiving a 450 µg/kg dose.

| | TGD* (days) | % Activity** |
|---|---|---|
| BT062 | 32 | 100 |
| nBT062-SPP-DM1 | 13 | 40 |

*Tumor growth delay in days (TGD) as mean time in days for treatment group to reach a predetermined size (160 mm$^3$) minus the mean time for the control group to reach this predetermined size.
**Tumor Growth Inhibiting Activity = 100 × (TGD$_{Sample}$/TGD$_{BT062}$). The activity of BT062 is defined to be 100%.

In the example provided in Table 2, BT062 provides a growth of a tumor inhibiting activity that exceeds that of its unhindered counterpart (nBT062-SPP-DM1) by 60%, and a growth of a tumor inhibiting activity that exceeds that of its unhindered counterpart immunoconjugate comprising a non-cleavable linker (nBT062-SMCC-DM1) by 44%.

It was previously reported that a cleavable linker in e.g., huC242-maytansinoid immunoconjugates may provides for a so called bystander effect. Goldmahker et al. (U.S. Patent Publication 2006/0233814) also disclose that the bystander effect is particularly pronounced when the effector molecule is subject to further modification, in particular alkylation, upon cleavage from the targeting agent. Goldmahker et al. also showed that UICL displayed better TGD than the respective UINCL (see, e.g., FIG. 6 of U.S. Patent Publication 2006/0233814).

However, the overall effectiveness of HICL/UICL/UINCL immunoconjugates appear to differ from immunoconjugate to immunoconjugate and/or target to target. For example the HICL trastuzumab-SPP-DM4 was clearly outperformed in its ability to reduce tumor size by the UINCL trastuzumab-SMCC-DM1, while performance of the UICL immunoconjugate trastuzumab-SPP-DM1 substantially resembled that of the corresponding HICL (see U.S. Patent Publication 2008/0171040 to Eberts et al.), thus rendering the results obtained a function of the immunoconjugate and the target.

FIG. 11A shows that the HICL outperformed the UICL and UNNCL, it was also surprisingly found that an UICL in a high single dosage regime (250 µg/kg) actually did not show any better results than the UINCL. In fact, the TGD in days that was observed in an UICL in such a regime was actually lower than that of the UINCL. This observation became more pronounced with an increase in dosage (450 µg/kg). In sum, as shown in FIG. 11A, HICL outperformed UICL in single dose experiments to an unexpected degree. Consistent with these results, in repeat dosage experiments, the HICL outperformed the UICL considerably, the latter of which provided results which only marginally exceeded that of the control. In addition, the UICL was outperformed by UINCL at higher dosages.

Adhesion of multiple myeloma cells to stromal cells, in particular bone marrow stromal cells, has been made accountable for adhesion mediated drug resistance (CAM-DR) that has been observed in multiple myeloma patients. In certain embodiments, the immunoconjugates of the present invention may alleviate CAM-DR. In particular, in certain embodiments of the present invention this adhesion is diminished by administering the immunoconjugate to said multiple myeloma cells, e.g., by at least about 10%, about 20%, about 30%, about 40%, about 50%, about 60%, about 70%, about 80% or more. As shown in FIG. 17E, in particular UICL and HICL were able to inhibit multiple myeloma cell adhesion to BMSCs (bone marrow stromal cells) in samples in which just the stroma cells were treated (as well as in samples in which the stroma cells where not treated), while the UINCL counterpart did not have this effect. These results suggest that the adhesion diminishing effect is dependent on the nature of the linker of the immunoconjugate, with cleavable linker that allow the effector molecule to dissociate more readily, being preferred. The fact that multiple myeloma cells are at least in part prevented from adhering to BMSCs also makes them more readily accessible to other cytotoxic agents, including those that are usually inhibited from acting, at least with full efficiency, on the multiple myeloma cells as a result of CAM-DR. Thus, administration of the immunoconjugate is preferably combined with a concomitant or subsequent administration of cytotoxic agent. Time intervals between the administration of the immunoconjugate and the cytotoxic agent may comprise 12 hours to 6 days, including 12 hours, 24 hours, 2, 3, 4 or 5 days.

The immunoconjugates disclosed herein can be administered by any route, including intravenously, parenterally, orally, intramuscularly, intrathecally or as an aerosol. The mode of delivery will depend on the desired effect. A skilled artisan will readily know the best route of administration for a particular treatment in accordance with the present invention. The appropriate dosage will depend on the route of administration and the treatment indicated, and can readily be determined by a skilled artisan in view of current treatment protocols.

Pharmaceutical compositions containing the immunoconjugate of the present invention and/or any further cytotoxic agent as active ingredients can be prepared according to conventional pharmaceutical compounding techniques. See, for example, Remington's Pharmaceutical Sciences, 17th Ed. (1985, Mack Publishing Co., Easton, Pa.). Typically, effective amounts of active ingredients will be admixed with a pharmaceutically acceptable carrier. The carrier may take a wide variety of forms depending on the form of preparation desired for administration, for example, intravenous, oral, parenteral, intrathecal, transdermal, or by aerosol.

For oral administration, the immunoconjugate and/or cytotoxic agent can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the immunoconjugate and/or cytotoxic agent may be dissolved in a pharmaceutical carrier and administered as either a solution or a suspension. Illustrative of suitable carriers are water, saline, phosphate buffer solution (PBS), dextrose solutions, fructose solutions, ethanol, or oils of animal, vegetative or synthetic origin. The carrier may also contain other ingredients, for example, preservatives, suspending agents, solubilizing agents, buffers and the like. When the unconjugated targeting agent and/or immunoconjugate and/or cytotoxic agent are being administered intracerebroventricularly or intrathecally, they may also be dissolved in cerebrospinal fluid.

Dosages administered to a subject may be specified as amount, per surface area of the subject (which include humans as well as non-human animals). The dose may be administered to such a subject in amounts, preferably, but not exclusively from about 5 mg/m$^2$ to about 300 mg/m$^2$, including about 20 mg/m$^2$, about 50 mg/m$^2$, about 100 mg/m$^2$, about 150 mg/m$^2$, about 200 mg/m$^2$ and about 250 mg/m$^2$. In certain embodiments, in which the immunoconjugate is administered in combination with a cytotoxic agent, the dose of the immunoconjugate may be lower. The immunoconjugates are suitably administered at one time or over a series of treatments. In a multiple dose regime these amounts may be administered once a day, once a week, once every two weeks, once every three weeks, once every four weeks, one every five weeks or once every six weeks. Loading doses with a single high dose or, alternatively, lower doses that are administered shortly after one another followed by dosages timed at longer intervals constitute a preferred embodiment of the present invention. In a preferred embodiment, the timing of the dosages are adjusted for a subject so that enough time has passed prior to a second and/or any subsequent treatment so that the previous dose has been metabolized substantially, but the amount of immunoconjugate present in the subject's system still inhibits, delays and/or prevents the growth of a tumor. An exemplary "repeated single dose" regime comprises administering an initial dose of immunoconjugate of about 200 mg/m$^2$ once every three weeks. Alternatively, a high initial dose may be followed by a biweekly maintenance dose of about 150 μg/m$^2$. However, other dosage regimens may be useful. The progress of this therapy is easily monitored by known techniques and assays. Dosage may vary depending on whether they are administered for preventive or therapeutic purposes, the course of any previous therapy, the patient's clinical history and response to the targeting agent/immunoconjugate, and the discretion of the attending physician.

In one embodiment, the immunoconjugate is administered with one or more additional cytotoxic agents, which is efficient in treating the same disease but which is, when administered without the immunoconjugate, often of limited effectiveness in view of CAM-DR; for example a CD138 specific immunoconjugate can be administered in combination with dexamethasone. In particular, dexamethasone is administered to a patient in need thereof in effective amount two hours after the immunoconjugate has been administered.

Thus, the immunoconjugate of the present invention may also particularly be administered in treatment regimens with high-dose chemotherapy (preferably, melphalan, melphalan/prednisone (MP), vincristine/doxorubicin/dexamethasone (VAD), liposomal doxorubicin/vincristine, dexamethasone (DVd), cyclophosphamide, etoposide/dexamethasone/cytarabine, cisplatin (EDAP)), stem cell transplants (e.g., autologous stem cell transplantation or allogeneic stem cell transplantation, and/or mini-allogeneic (non-myeloablative) stem cell transplantation), steroids (e.g., corticosteroids, dexamethasone, thalidomide/dexamethasone, prednisone, melphalan/prednisone), supportive therapy (e.g., bisphosphonates, growth factors, antibiotics, intravenous immunoglobulin, low-dose radiotherapy, and/or orthopedic interventions), THALOMID (thalidomide, Celgene), VELCADE (bortezomib, Millennium), and/or REVLIMID (lenalidomide) (Chelgene Corporation) and/or other multiple myeloma treatments including radiation therapy.

If an immunoconjugate of the present invention is administered in combination with a cytotoxic agents, the above doses and regimes are often maintained. However, if the immunoconjugate and the cytotoxic agent are co-administered, low dosages of each of these therapeutic components are, in certain embodiments, preferred. In such a situation, the immunoconjugate may be administered at doses from about 5 mg/m$^2$ to about 100 mg/m$^2$, including about 20 mg/m$^2$, about 50 mg/m$^2$, while the cytotoxic agent is administered at doses as the recommended when administered alone.

The experimental data obtained in the cell culture based (FIG. 7) and mouse experiments (FIGS. 8 to 11), was further confirmed with experiments that further supported these finding.

The pathogenesis of multiple myeloma involves binding of myeloma cells, via cell-surface adhesion molecules, not only to bone marrow stroma cells (BMSCs) but also extracellular matrix (ECM). This binding triggers, and thus can be made ultimately responsible, for multiple myeloma cell growth, drug resistance, and migration of MM cells in the bone marrow milieu (Munshi et al. 2008). In particular, the adhesion of multiple myeloma cells to ECM via syndecan-1 (CD138) to type I collagen, induces the expression of matrix metalloproteinase 1, thus promoting bone resorption and tumour invasion (Hideshima et al. 2007). Interactions between multiple myeloma cells and the bone marrow microenvironment results in activation of a pleiotropic proliferative and anti-apoptotic cascade.

Following the homing of multiple myeloma cells to the bone marrow stromal compartment, adhesion between multiple myeloma cells and BMSCs upregulates many cytokines like interleukin-6 (IL-6) and insulin like growth factor 1 (IGF-1) which have angiogenic and tumor growth promoting activities (Hideshima et al. 2007). The signalling cascades initiated by these cytokines eventually result in MM cell resistance to conventional therapeutics (Anderson et al. 2000; Hideshima et al. 2006).

Figure 12:
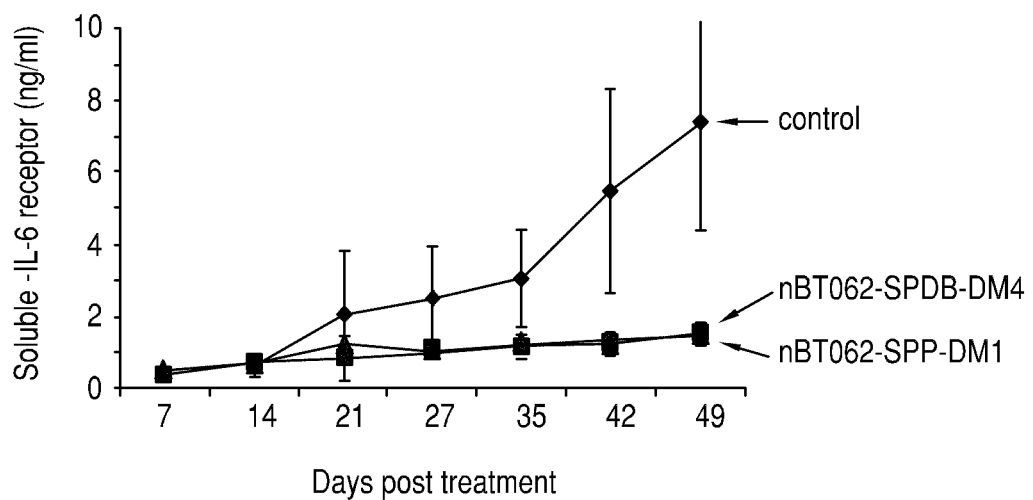
FIG. 12 is a graph reflecting the anti-tumour efficacy of nBT062 containing DMx conjugates in the SCIDhu/INA-6 model towards multiple myeloma cells in the environment of human bone marrow. Soluble human IL-6 Receptor produced by multiple myeloma cells (shuIL-6R) was used as an indicator for tumor burden. Triangle: nBT062-SPP-DM1, Square: nBT062-SPDB-DM4; Diamond: vehicle control.

The in vivo efficacy of nBT062-SPDB-DM4 and nBT062-SPP-DM1 against CD138-positive tumor cells in the presence of human bone marrow was analyzed in a mouse model and the results of this analysis are shown in FIG. 12. The Figure shows that both HICL and UICL perform well in this environment. The increase in the level of shuIL-6R which can, in this model, be used as a parameter of MM cell growth, were both suppressed by the these immunoconjugates.

In accordance with the present invention, MM is treated as follows, with the use of BT062 as an example. This example is not intended to limit the present invention in any manner, and a skilled artisan could readily determine other immunoconjugate or nBT062 based systems that are within the scope of the present invention and other treatment regimes which could be utilized for the treatment of diseases such as MM.

Due to the selective expression of CD138 on patient MM cells on via the blood stream accessible cells, the specificity of nBT062 and the stability of BT062 in the bloodstream, BT062 removes the systemic toxicity of DM4 and provides an opportunity to target the delivery of the DM4-effector molecule(s). The immunoconjugates of this invention provide a means for the effective administration of the effector molecules to cell sites where the effector molecules can be released from the immunoconjugates.

One or more cytotoxic agents are administered in the dosages and dosage forms and according to establish treatment protocols for these cytotoxic agents to an individual that is also treated with an immunoconjugate of the present invention.

In particular, a patient is subjected to a treatment regime using an appropriate dosage of BT062, e.g., 100 mg/m² according to the present invention at certain intervals, e.g. initially daily and then weekly. Twelve hours after each weekly immunoconjugate treatment, the patient is also treated with melphalan, e.g., by administering an oral dosage according to the manufacturer's instruction is administered to the patient (e.g. a pill traded under the trademark ALKERAN).

In accordance with the present invention, in particular solid tumors may also be treated as follows using BT062 as an example. This example is not intended to limit the present invention in any manner, and a skilled artisan could readily determine other immunoconjugates of the present invention and other treatment regimes which could be utilized for the treatment of solid tumors. The tumor is first treated to reduce the size of the tumor, for example radioactively. Subsequent administration of BT062, followed by a dose of a cytotoxic agent, e.g. in form of an ALKERAN pill, provides a highly effective means for eliminating residual cancer cells. The administration of the immunoconjugate allows specific targeting of these residual cells and release of the effector molecules at the target site. The immunoconjugate not only overcomes or diminishes CAM-DR with respect to its own activity, but due to the fact that inhibits multiple myeloma cell adhesion to stroma cells, the immunoconjugate also overcomes or diminishes CAM-DR for other cytotoxic agents. The high efficacy of the immunoconjugate allows, in preferred embodiments, for a single dose regime.

The present invention is further described by reference to the following Examples, which are offered by way of illustration and are not intended to limit the invention in any manner. Standard techniques well known in the art or the techniques specifically described below are utilized.

Materials and Methods
Chimeric Antibody Construction (cB-B4: nBT062)
B-B4

Murine antibody B-B4 as previously characterized (Wijdenes et al., Br J Haematol., 94 (1996), 318) was used in these experiments.

Cloning and Expression of B-B4 and cB-B4/nBT062

Standard recombinant DNA techniques were performed as described in detail in text books, for example in J. Sambrook; Molecular Cloning, A Laboratory Manual; 2nd Ed. (1989), Cold Spring Harbor Laboratory Press, USA, or as recommended by the manufacturer's instruction in the cases when kits were used. PCR-cloning and modification of the mouse variable regions have been conducted using standard PCR methodology. Primers indicated in the respective results section have been used.

Expression of cB-B4/nBT062

Exponentially growing COS cells, cultured in DMEM supplemented with 10% FCS, 580 µg/ml L-glutamine, 50 Units/ml penicillin and 50 µg/ml streptomycin were harvested by trypsinization and centrifugation and washed in PBS. Cells were resuspended in PBS to a final concentration of $1 \times 10^7$ cells/ml. 700 µl of COS cell suspension was transferred to a Gene Pulser cuvette and mixed with heavy and kappa light chain expression vector DNA (10 µg each or 13 µg of Supervector). Cells were electroporated at 1900 V, 25 µF using a Bio-Rad Gene Pulser. Transformed cells were cultured in DMEM supplemented with 10% gamma-globulin free FBS, 580 µg/ml L-glutamine, 50 Units/ml penicillin and 50 µg/ml streptomycin for 72 h before antibody-containing cell culture supernatants were harvested.

Capture ELISA to Measure Expression Levels of cB-B4/nBT062

96 well plates were coated with 100 µl aliquots of 0.4 µg/ml goat anti-human IgG antibody diluted in PBS (4° C., overnight). Plates were washed three times with 200 µl/well washing buffer (PBS+0.1% Tween-20). Wells were blocked with 0.2% BSA, 0.02% Tween-20 in PBS, before addition of 200 µl cell culture supernatants containing the secreted antibody (incubation at 37° C. for one hour). The wells were washed six times with washing buffer, before detection of bound antibody with goat anti-human kappa light chain peroxidase conjugate.

Purification of cB-B4/nBT062 From Cell Culture Supernatants

The cB-B4 antibody was purified from supernatants of transformed COS 7 cells using the Protein A ImmunoPure Plus kit (Pierce, Rockford, Ill.), according to the manufacturer's recommendation.

cB-B4 Binding and Competition Assay

Analysis of binding activity of B-B4 and cB-B4 to CD138 was performed using the Diaclone (Besançon, France) sCD138 kit according to the manufacturer's recommendation, considering the changes described in the results section.

RNA Preparation and cDNA Synthesis

Hybridoma B-B4 cells were grown and processed using the Qiagen Midi kit (Hilden, Germany) to isolate RNA following the manufacturer's protocol. About 5 µg of B-B4 RNA was subjected to reverse transcription to produce B-B4 cDNA using the Amersham Biosciences (Piscataway, N.J.) 1st strand synthesis kit following the manufacturer's protocol.

Cloning of B-B4 Immunoglobulin cDNA

Immunoglobulin heavy chain (IgH) cDNA was amplified by PCR using the IgH primer MHV7 (5'-ATGGGCATCAAGATGGAGTCACAGACCCAGG-3') [SEQ ID NO:3] and the IgG1 constant region primer MHCG1 (5'-CAGTGGATAGACAGATGGGGG-3') [SEQ ID NO:4]. Similarly, immunoglobulin light chain (IgL) was amplified using the three different IgK primers MKV2 (5'-ATGGAGACAGACACACTCCTGCTATGGGTG-3') [SEQ ID NO:5], MKV4 (5'-ATGAGGGCCCCTGCTCAGTTTTTTGGCTTCTTG-3') [SEQ ID NO:6] and MKV9 (5'-ATGGTATCCACACCTCAGTTCCTTG-3') [SEQ ID NO:7], each in combination with primer MKC (5'-ACTGGATGGTGGGAAGATGG-3') [SEQ ID NO:8]. All amplification products were directly ligated with the pCR2.1-TOPO vector using the TOPO-TA cloning kit (Invitrogen, Carlsbad, Calif.) according to the manufacturer's instruction.

*E. coli* TOP10 bacteria (Invitrogen) transformed with the ligated pCR2.1 vector constructs were selected on LB-ampicillin-Xgal agar plates. Small scale cultures were inoculated with single white colonies, grown overnight and plasmids were isolated using the QIAprep Spin Miniprep kit according to the manufacturer's instruction.

cDNA Sequence Determination

Plasmids were sequenced using the BigDye Termination v3.0 Cycle Sequencing Ready Reaction Kit (ABI, Foster City, Calif.). Each selected plasmid was sequenced in both directions using the 1210 and 1233 primers cycled on a GeneAmp9600 PCR machine. The electrophoretic sequence analysis was done on an ABI capillary sequencer.

The complete cycle of RT-PCR, cloning and DNA sequence analysis was repeated to obtain three completely independent sets of sequence information for each immunoglobulin chain.

B-B4 VK DNA Sequence

1st strand synthesis was performed in three independent reactions. The PCR products generated by using primers MKC and MKV2 (sequences given above) were ligated into pCR2.1-TOPO vectors according to the manufacturer's instruction. Clones from each independent set of RT-PCR reactions were sequenced in both directions. MKV2-primed product sequence was highly similar to sterile kappa transcripts originating from the myeloma fusion partner such as MOPC-21, SP2 and Ag8 (Carroll et al., Mol Immunol., 25 (1988), 991; Cabilly et al., Gene, 40 (1985); 157) and was therefore disregarded.

The PCR products using MKC with MKV4 and MKV9 primers were similar to each other and differed only at the wobble positions within the leader sequence primer.

B-B4 VH DNA Sequence

1st strand synthesis was performed in three independent reactions and PCR products were cloned and sequenced from each 1st strand product. Five clones were sequenced from each 1st strand.

Construction of Chimeric cB-B4 Expression Vectors

The construction of the chimeric expression vectors entails adding a suitable leader sequence to VH and VK, preceded by a BamHI restriction site and a Kozak sequence. The Kozak consensus sequence is crucial for the efficient translation of a variable region sequence. It defines the correct AUG codon from which a ribosome can commence translation, and the single most critical base is the adenine (or less preferably, a guanine) at position -3, upstream of the AUG start. The leader sequence is selected as the most similar sequence in the Kabat database (Kabat et al., NIH National Technical Information Service, 1991). These additions are encoded within the forward (For) primers (both having the sequence 5'-AGAGAAGCTTGCCGCCACCAT-GATT-GCCTCTGCTCAGTTCCTTGGTCTCC-3' [SEQ ID NO:9]; restriction site is underlined; Kozak sequence is in bold type). Furthermore, the construction of the chimeric expression vectors entails introducing a 5' fragment of the human gamma1 constant region, up to a natural ApaI restriction site, contiguous with the 3' end of the J region of B-B4 and, for the light chain, adding a splice donor site and HindIII site. The splice donor sequence is important for the correct in-frame attachment of the variable region to its appropriate constant region, thus splicing out the V:C intron. The kappa intron+CK are encoded in the expression construct downstream of the B-B4 VK sequence. Similarly, the gamma-4 CH is encoded in the expression construct downstream of the B-B4 VH sequence.

The B-B4 VH and VK genes were first carefully analyzed to identify any unwanted splice donor sites, splice acceptor sites, Kozak sequences and for the presence of any extra sub-cloning restriction sites which would later interfere with the subcloning and/or expression of functional whole antibody. An unwanted HindIII site was found in the VK sequence which necessarily was removed by site-directed mutagenesis via PCR without changing the amino acid sequence. For this reactions, oligonucleotide primers BT03 (5'-CAACAGTATAGTAAGCTCCCTCGGACGTTCG-GTGG-3') [SEQ ID NO:10] and BT04 (5'-CCAC-CGAACGTCCGAGGGAGCTTACTATACTGTTG-3') [SEQ ID NO:11] were used and mutagenesis was performed according to the Stratagene (La Jolla, Calif.) Quickchange Mutagenesis Kit protocol.

Kappa Chain Chimerization Primers

The non-ambiguous B-B4 VK leader sequence, independent of the PCR primer sequence, was aligned with murine leader sequences in the Kabat database. The nearest match for the B-B4 VH leader was VK-10 ARS-A (Sanz et al., PNAS, 84 (1987), 1085). This leader sequence is predicted to be cut correctly by the SignalP algorithm (Nielsen et al., Protein Eng, 10 (1997); 1). Primers CBB4Kfor (see above) and g2258 (5'-CGCGGGATCCACTCACGTTTGATTTC-CAGCTTGGTGCCTCC-3' [SEQ ID NO:12]; Restriction site is underlined) were designed to generate a PCR product containing this complete leader, the B-B4 VK region, and HindIII and BamHI terminal restriction sites, for cloning into the pKN100 expression vector. The forward primer, CBB4K introduces a HindIII restriction site, a Kozak translation initiation site and the VK-10 ARS-A leader sequence. The reverse primer g2258 introduces a splice donor site and a BamHI restriction site. The resulting fragment was cloned into the HindIII/BamHI restriction sites of pKN100.

Heavy Chain Chimerization Primers

The non-ambiguous B-B4 VH leader sequence, independent of the PCR primer sequence, was aligned with murine leader sequences in the Kabat database. The nearest match for the B-B4 VK leader was VH17-1A (Sun et al., PNAS, 84 (1987), 214). This leader sequence is predicted to be cut correctly by the SignalP algorithm. Primers cBB4Hfor (see above) and g22949 (5'-CGATGGGCCCTTGGTGGAG-GCTGAGGA-GACGGTGACTGAGGTTCC-3' [SEQ ID NO:13]; Restriction site is underlined) were designed to generate a PCR product containing VH17-1A leader, the B-B4 VH region, and terminal HindIII and ApaI restriction sites, for cloning into the pG4D200 expression vector. The forward primer cBBHFor introduces a HindIII restriction site, a Kozak translation initiation site and the VH17-1A leader sequence. The reverse primer g22949 introduces the 5' end of the gamma4 C region and a natural ApaI restriction site. The resulting fragment was cloned into the HindIII/ApaI restriction sites of pG4D200, resulting in vector pG4D200cBB4.

Production of cBB4 Antibody

One vial of COS 7 cells was thawed and grown in DMEM supplemented with 10% Fetal clone I serum with antibiotics. One week later, cells (0.7 ml at $10^7$ cells/ml) were electroporated with pG4D200cBB4 plus pKN100cBB4 (10 µg DNA each) or no DNA. The cells were plated in 8 ml growth medium for 4 days. Electroporation was repeated seven times.

Detection of Chimeric Antibody

A sandwich ELISA was used to measure antibody concentrations in COS 7 supernatants. Transiently transformed COS 7 cells secreted about 6956 ng/ml antibody (data not shown).

Binding Activity of cB-B4

To assay the binding activity of cB-B4 in COS 7 culture supernatants, the Diaclone sCD138 kit has been used, a solid phase sandwich ELISA. A monoclonal antibody specific for sCD138 has been coated onto the wells of the microtiter strips provided. During the first incubation, sCD138 and biotinylated B-B4 (bio-B-B4) antibody are simultaneously incubated together with a dilution series of unlabeled test antibody (B-B4 or cB-B4).

The concentrations of bio-B-B4 in this assay have been reduced in order to obtain competition with low concentrations of unlabeled antibody (concentration of cB-B4 in COS 7 cell culture supernatants were otherwise too low to obtain sufficient competition). Results from this assay reveal that both antibodies have the same specificity for CD138 (data not shown).

Purification of cB-B4

Chimeric B-B4 was purified from COS 7 cell supernatants using the Protein A ImmunoPure Plus kit (Pierce), according to the manufacturer's recommendation (data not shown).

$K_D$-Determination: Comparison nBT062/BB4

Purification of Soluble CD138

Soluble CD138 antigen from U-266 cell culture supernatant was purified by FPLC using a 1 mL "HiTrap NHS-activated HP" column coupled with B-B4. Cell culture supernatant was loaded in PBS-Buffer pH 7.4 onto the column and later on CD138 antigen was eluted with 50 mM tri-ethylamine pH 11 in 2 mL fractions. Eluted CD138 was immediately neutralised with 375 µL 1 M Tris-HCl, pH 3 to prevent structural and/or functional damages.

Biotinylation of CD138

Sulfo-NHS-LC (Pierce) was used to label CD138. NHS-activated biotins react efficiently with primary amino groups like lysine residues in pH 7-9 buffers to form stable amide bonds.

For biotinylation of CD138, 50 µl of CD138 were desalted using protein desalting spin columns (Pierce). The biotinylation reagent (EZ-Link Sulfo NHS-LC-Biotin, Pierce) was dissolved in ice-cooled deionised $H_2O$ to a final concentration of 0.5 mg/mL. Biotinylation reagent and capture reagent solution were mixed having a 12 times molar excess of biotinylation reagent compared to capture reagent (50 pmol CD138 to 600 pmol biotinylation reagent) and incubated 1 h at room temperature while shaking the vial gently. The unbound biotinylation reagent was removed using protein desalting columns.

Immobilization of bCD138

The sensorchip (SENSOR CHIP SA, BIACORE AB) used in the BIACORE assay is designed to bind biotinylated molecules for interaction analysis in BIACORE systems. The surface consists of a carboxymethylated dextran matrix pre-immobilized with streptavidin and ready for high-affinity capture of biotinylated ligands. Immobilization of bCD138 was performed on SENSOR CHIP SA using a flow rate of 10 µL/min by manual injection. The chip surface was conditioned with three consecutive 1-minute injections of 1 M NaCl in 50 mM NaOH. Then biotinylated CD138 was injected for 1 minute.

$K_D$-Determination of Different Antibodies Using BIACORE

The software of BIACORE C uses pre-defined masks, so called "Wizards" for different experiments where only certain settings can be changed. As the BIACORE C was originally developed to measure concentrations, there is no wizard designed to carry out affinity measurements. However, with the adequate settings, the wizard for "non-specific binding" could be used to measure affinity rate constants and was therefore used for $K_D$-determination. With this wizard, two flow cells were measured and the dissociation phase was set to 90 s by performing the "Regeneration 1" with BIACORE running buffer. "Regeneration 2" which is equivalent to the real regeneration was performed with 10 mM Glycine-HCl pH 2.5. After this step, the ligand CD138 was in its binding competent state again. During the whole procedure HBS-EP was used as running and dilution buffer. To determine binding of the different antibodies (~150 kDa) to CD138, association and dissociation was analysed at different concentrations (100, 50, 25, 12.5, 6.25 and 3.13 nM). The dissociation equilibrium constants were determined by calculating the rate constants ka and kd. Afterwards, the $K_D$-values of the analytes were calculated by the quotient of kd and ka with the BIAevaluation software. The results are shown in Table 4.

TABLE 4

Comparative analysis of $K_D$ values of nBT062 and B-B4. Standard deviations are given for mean $K_D$ values.

| Antibody | Affinity | |
|---|---|---|
| | $K_D$ (nM) | mean $K_D$ (nM) |
| nBT062 | 1.4 | 1.4 +/− 0.06 |
| | 1.4 | |
| | 1.5 | |
| B-B4 | 1.7 | 1.6 +/− 0.06 |
| | 1.7 | |
| | 1.6 | |
| nBT062-SPDB-DM4 | 1.9 | 1.9 +/− 0.00 |
| | 1.9 | |
| | 1.9 | |
| B-B4-SPP-DM1 | 2.6 | 2.6 +/− 0.06 |
| | 2.7 | |
| | 2.6 | |

Discussion

Mean $K_D$ values for each antibody were calculated from three independent experiments. The results show that in all measurements nBT062 exhibits slightly decreased $K_D$ values compared to B-B4 (mean $K_D$ values were 1.4 and 1.6 nM, respectively).

Preparation of Immunoconjugates nBT062-DM1 and huC242-DM1

The thiol-containing maytansinoid DM1 was synthesized from the microbial fermentation product ansamitocin P-3, as previously described by Chari (Chari et al., Cancer Res. 1 (1992), 127). Preparation of humanized C242 (huC242) (Roguska et al., PNAS, 91 (1994), 969) has been previously described. Antibody-drug conjugates were prepared as previously described (Liu et al., PNAS, 93 (1996), 8618). An average of 3.5 DM1 molecules was linked per antibody molecule.

nBT062-DM4

BT062 is an antibody-drug conjugate composed of the cytotoxic maytansinoid drug, DM4, linked via disulfide bonds through a linker to the nBT062 chimerized monoclonal antibody. Maytansinoids are anti-mitotics that inhibit tubulin polymerization and microtubule assembly (Remillard et al., Science 189 (1977), 1002). Chemical and schematic representations of BT062 (nBT062-DM4) are shown in FIGS. 1 and 2.

Synthesis of DM4

DM4 is prepared from the well known derivative maytansinol (Kupchan et al., J. Med. Chem., 21 (1978), 31). Maytansinol is prepared by reductive cleavage of the ester moiety of the microbial fermentation product, ansamitocin P3, with lithium trimethoxyaluminum hydride (see FIG. 3).

DM4 is synthesized by acylation of maytansinol with N-methyl-N-(4-methydithiopentanoyl)-L-alanine (DM4 side chain) in the presence of dicyclohexylcarbodiimide (DCC) and zinc chloride to give the disulfide-containing maytansinoid DM4-SMe. The DM4-SMe is reduced with dithiothreitol (DTT) to give the desired thiol-containing maytansinoid DM4 (see FIG. 4 for the DM4 process flow diagram).

Immunoconjugate BT062

Figure 5:
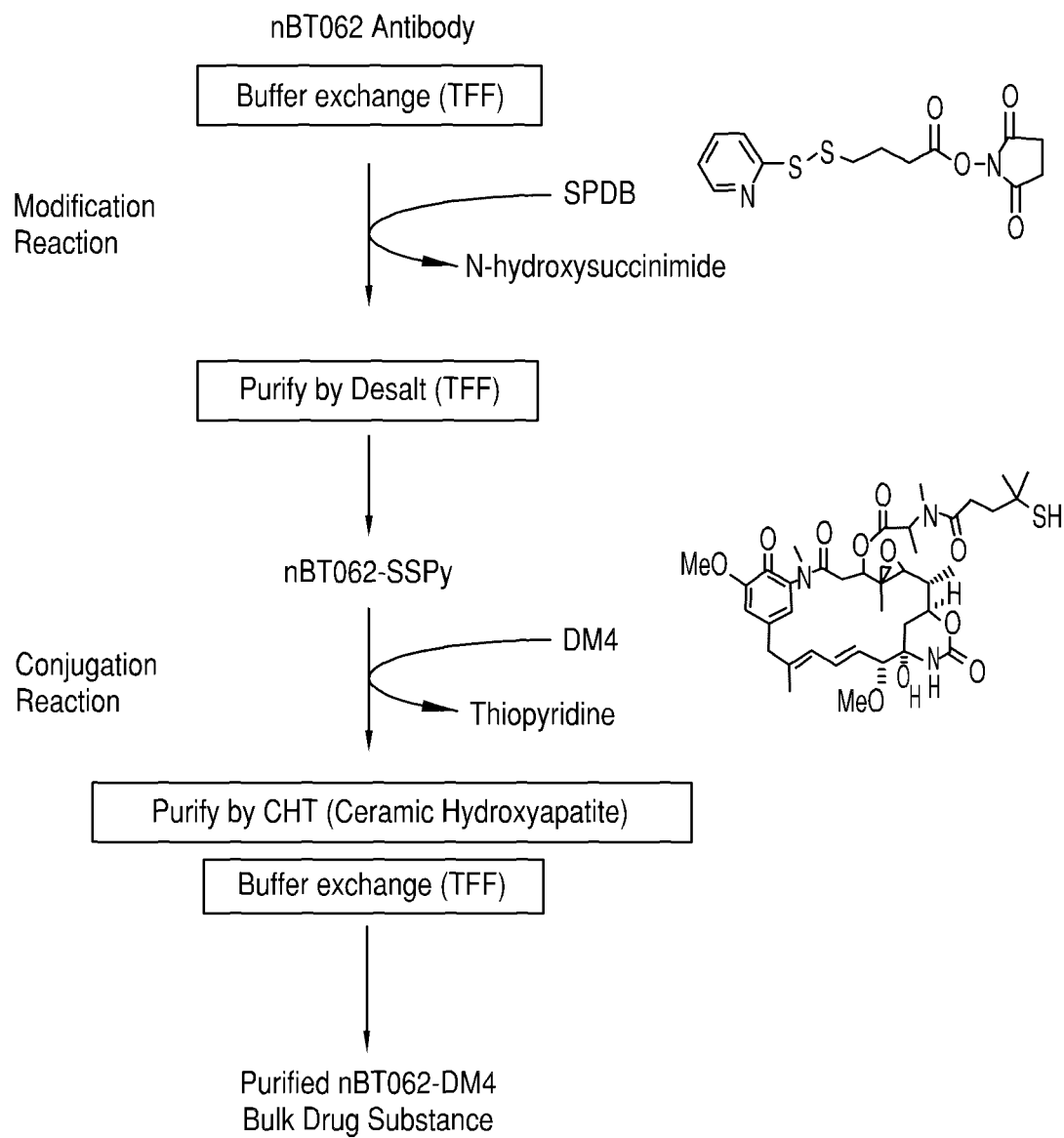
FIG. 5 is a schematic representation of an antibody conjugation (nBT062 to DM4).

The procedure for the preparation of nBT062-DM4 is outlined in FIG. 5. The nBT062 antibody is modified with N-succinimidyl-4-(2-pyridyldithio) butyrate (SPDB linker)

to introduce dithiopyridyl groups. DM4 is mixed with the modified antibody at a concentration in excess of the equivalents of dithiopyridyl groups. The BT062 conjugate forms by a disulfide exchange reaction between the thiol group of DM4 and the dithiopyridyl groups introduced into the antibody via the linker. Purification by chromatography and diafiltration removes the low molecular weight reactants (DM4) and reaction products (thiopyridine), as well as aggregates of conjugated antibody, to produce the bulk drug substance.

FACS Analysis and WST Cytotoxicity Assays

FACS Analysis

OPM-2 cells are plasma cell leukemia cell lines showing highly expressing CD138. OPM-2 cells were incubated with nBT062, nBT062-SPDB-DM4, nBT062-SPP-DM1 or nBT062-SMCC-DM1 at different concentrations (indicated in FIG. 6). The cells were washed and CD138-bound antibody or conjugates were detected using a fluorescence-labeled secondary antibody in FACS analysis. The mean fluorescence measured in these experiments was plotted against the antibody concentration.

Cell Viability Assay

CD138$^+$ MOLP-8 cells were seeded in flat bottom plates at 3000 cells/well. CD138$^-$ BJAB control cells were seeded at 1000 cells/well. The cells were treated with nBT062-SPDB-DM4, nBT062-SPP-DM1 or nBT062-SMCC-DM1 at different concentrations (indicated in FIG. 7) for five days. WST reagent (water-soluble tetrazolium salt, ROCHE) was added in order to measure cell viability according to the manufacturer's instruction (ROCHE). The reagent was incubated for 7.5 h on MOLP-8 cells and for 2 h on BJAB cells. The fraction of surviving cells was calculated based on the optical densities measured in a microplate reader using standard procedures.

Discussion

Figure 6:
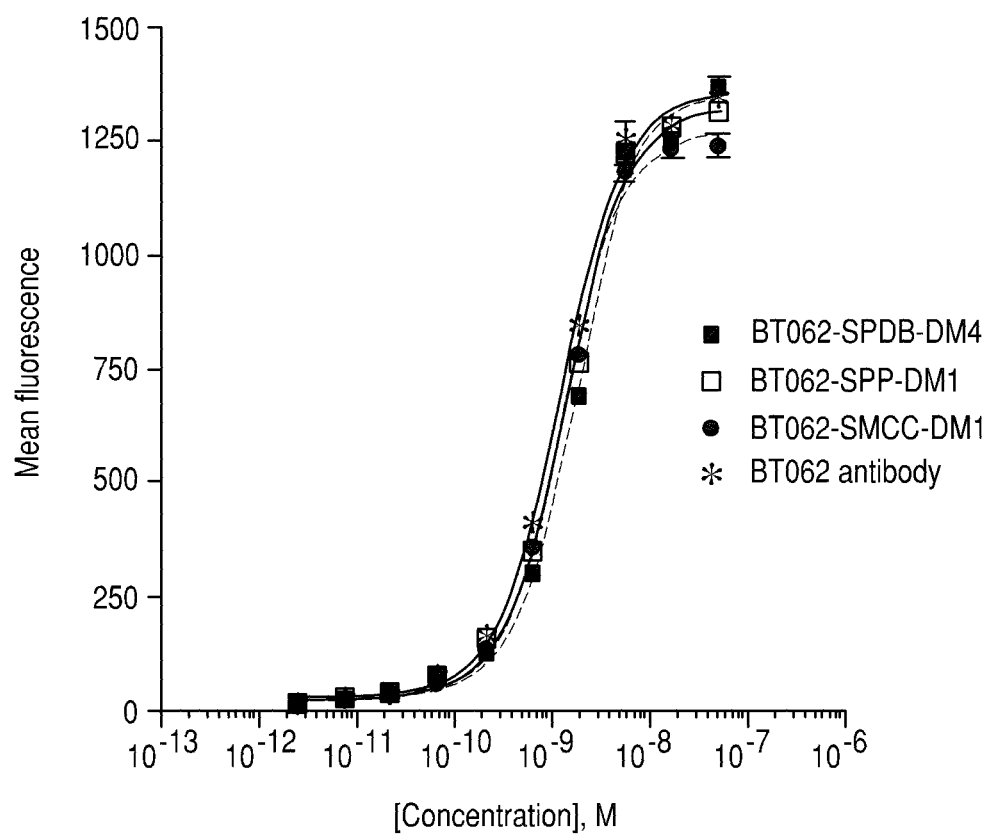
FIG. 6 shows an analysis of the binding of nBT062-SPDB-DM4, nBT062-SPP-DM1, nBT062-SMCC-DM1 and nBT062 antibody to OPM-2 cells. Different concentrations of nBT062 and conjugates were given to the cells and mean fluorescence was measured by FACS analysis.
Figure 7A:
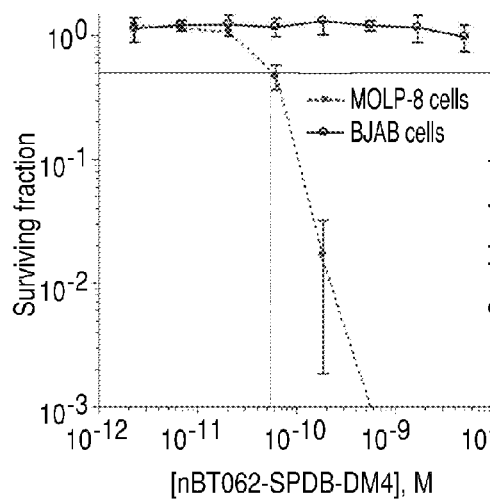
FIG. 7(A)-(D) depict in vitro cytotoxicity of nBT062-DMx conjugates towards MOLP-8 (CD138$^+$) and BJAB (CD138$^-$) cells. The cells were cultured in flat bottom plates and incubated with the indicated concentrations of immunoconjugates for 5 days. WST reagent was added for further 3 hours to assess cell viability. In (D) cytotoxic activity of nBT062-SPDB-DM4 was analyzed in the presence or absence of blocking antibody (1 μM nBT062).
Figure 7B:
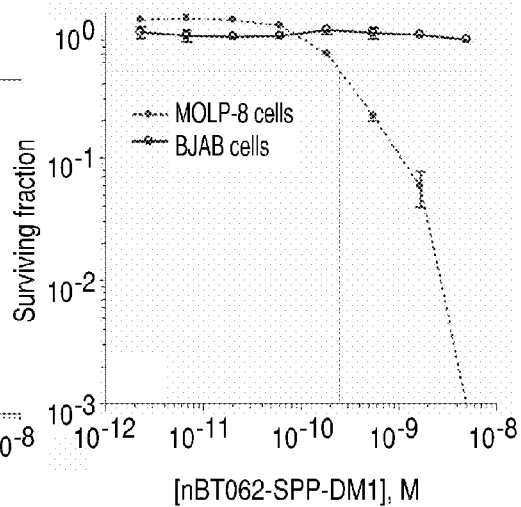
Figure 7C:
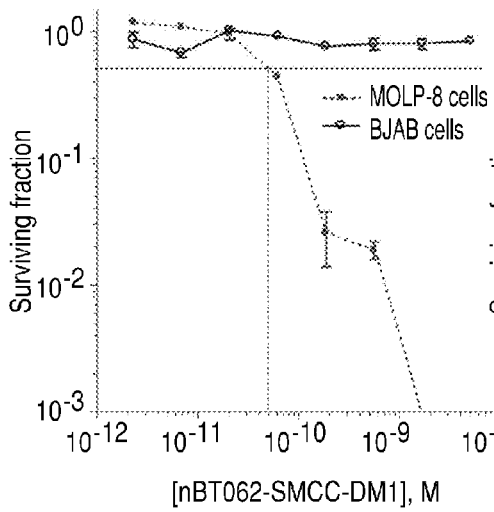
Figure 7D:
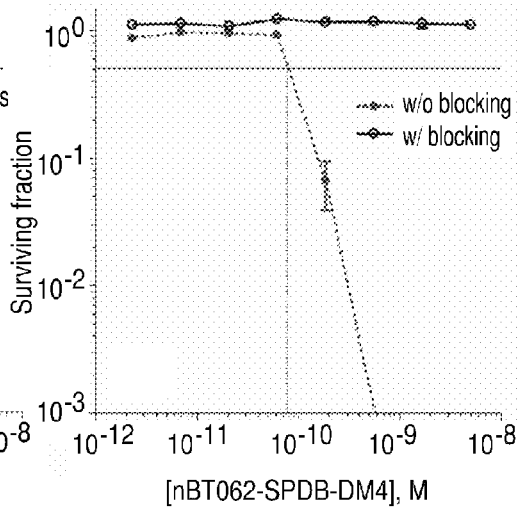
Figure 8A:
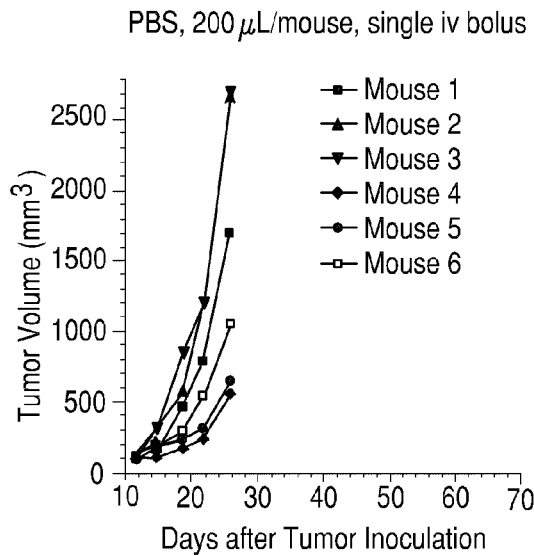
FIG. 8 shows tumor volumes for individual mice treated with (A) PBS, (B) nBT062 antibody, (C) free DM4 or (D) non-targeting conjugate huC242-DM4 over time (days) post-inoculation with MOLP-8 tumor cells.
Figure 8B:
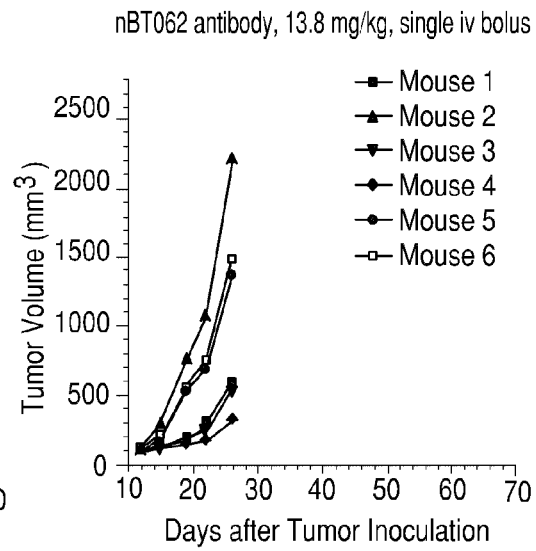
Figure 8C:
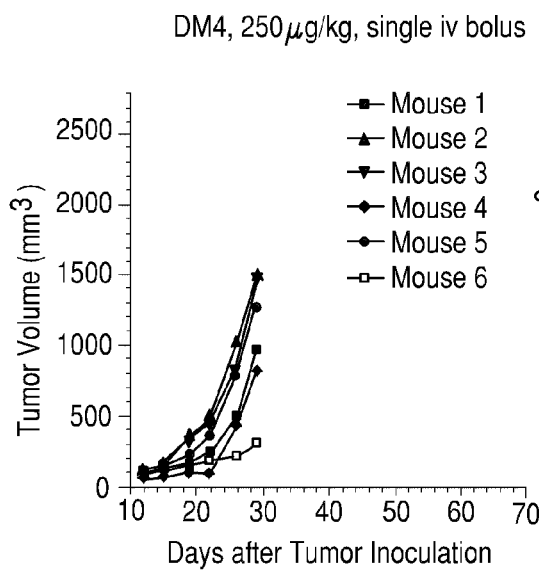
Figure 8D:
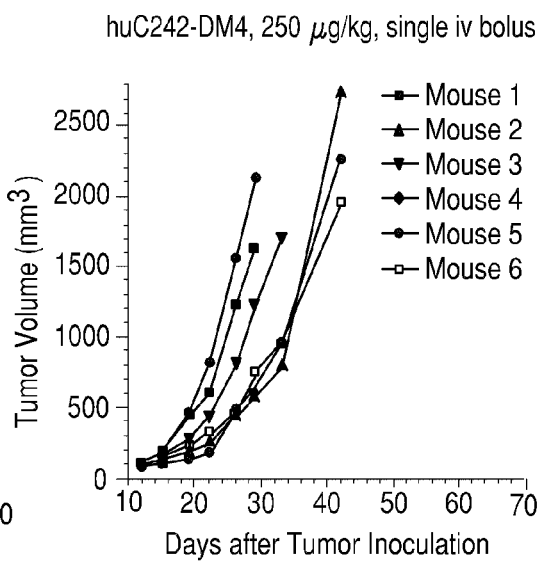

Binding of nBT062-SPDB-DM4, nBT062-SPP-DM1, nBT062-SMCC-DM1 or nBT062 was analyzed by FACS. CD138$^+$ OPM-2 as target cells were incubated with nBT062 or immunoconjugates and cell-bound molecules were detected using a fluorescence-labeled secondary antibody. In FIG. 6, the mean fluorescences as measure for the amount of cell bound antibody is plotted against different antibody or conjugate concentrations. The results show, that nBT062-SPDB-DM4, nBT062-SPP-DM1 and nBT062-SMCC-DM1 show very similar binding characteristics. In addition, the results strongly suggest that the binding characteristics of the unconjugated antibody is not affected by the conjugated toxins.

In cell viability assays, the cytotoxic activity of the antibody against CD138$^+$ MOLP-8 target cells and against CD138$^-$ BJAB B-lymphoblastoma control cells were analyzed. Both cell lines were seeded in flat-bottom plates and incubated with increasing concentrations of the immunoconjugates. Unconjugated antibody was used as a control. The cytotoxic activity was analyzed five days after addition of the immunoconjugates by using WST reagent in order to measure cell viability. In FIG. 7 (A)-(C), the fraction of surviving cells relative to control cells treated with vehicle control is plotted against increasing immunoconjugate concentrations. The results show that cytotoxic activity of nBT062-SPDB-DM4, nBT062-SPP-DM1 and nBT062-SMCC-DM1 against MOLP-8 cells is very similar. As expected, CD138$^-$ BJAB control cells were not killed by the immunoconjugates, indicating that all immunoconjugates act via cell specific binding to CD138. In competition experiments, in which MOLP-8 cells were preincubated with a molar excess of unconjugated nBT062. Preincubation substantially blocked the cytotoxicity of nBT062-SPDB-DM4, providing further evidence that the immunoconjugates kill the cells via specific binding to CD138 onto the cell surface (FIG. 7 (D)).

Xenograft Mouse Experiments

To evaluate the importance of CD138 targeting on the anti-tumor activity of antibody-maytansinoid conjugates of a human chimeric version of the B-B4 antibody, nBT062, xenograft mouse experiments were performed. Two versions of nBT062-maytansinoid conjugates were prepared that may differ in the chemical stability of their disulfide linkages (nBT062-SPP-DM1 and nBT062-SPDB-DM4). The anti-tumor activity of these antibody-drug conjugates was compared to the activity of the B-B4-SPP-DM1 conjugate (comprising the murine parental antibody), as well as unconjugated free maytansinoid (DM4), native unmodified nBT062 antibody, and a non-targeting (irrelevant) IgG1-maytansinoid conjugate. The conjugates were evaluated in a CD138-positive xenograft model (MOLP-8) of human multiple myeloma in severe combined immunodeficient (SCID) mice.

In these mice, subcutaneous tumors were established (female CB.17 SCID mice) by inoculation with MOLP-8 cell suspensions. Treatment with a single bolus intravenous injection was conducted when tumor volumes reached an average 113 mm$^3$. Changes in tumor volume and body weight were monitored twice per week. Experiments were carried out over 68 days after tumor cell inoculation.

Xenograft Mouse Experiments A

Mice

Female CB.17 SCID mice, five weeks old, were obtained from Charles River Laboratories.

Human Tumor Cell Lines

MOLP-8, a human multiple myeloma cell line, was supplied from ATCC. MOLP-8 cells, which express the CD138 antigen on their cell surface and develop xenograft tumors in SCID mice, were maintained in RPMI-1640 medium supplemented with 4 mM L-glutamine (Biowhittaker, Walkersville, Md.), 10% fetal bovine serum (Hyclone, Logan, Utah) and 1% streptomycin/penicillin, at 37° C. in a humidified atmosphere that contained 5% $CO_2$.

Part I

Tumor Growth in Mice

Each mouse was inoculated with $1 \times 10^7$ MOLP-8 cells subcutaneously into the area under the right shoulder. The total volume was 0.2 ml per mouse, in which the ratio of serum-free medium to matrigel (BD Bioscience, Bedford, Mass.) was 1/1 (v/v). Prior to treatment, the xenograft tumors were monitored daily and were allowed to become established. The tumor volume reached approximately 113 mm$^3$ about 11 days after tumor cell inoculation. Tumor take rate of CB.17 SCID mice was 100%.

Eleven days after tumor cell inoculation, 42 mice were selected based on tumor volumes and body weights. The tumor volume was in a range of 68.2 to 135.9 mm$^3$. The forty-two mice were randomly divided into seven groups (A-G) of six animals each based on tumor volume.

Each of six mice in Group A received 200 µl of PBS as vehicle control. Each mouse in group B received 13.8 mg/kg of nBT062 naked antibody. This dose is equivalent to the amount of nBT062 antibody component in 250 µg/kg of linked maytansinoid. The ratio of molecular weights of maytansinoids to nBT062 antibody in a conjugate molecule is approximate 1/55. Each mouse in Group C received 250 µg/kg of DM4. Each mouse in Group D received 250 µg/kg of huC242-DM4. Mice in groups E, F and G received 250

μg/kg of nBT062-SPDB-DM4, B-B4-SPP-DM1 and nBT062-SPP-DM1 each, respectively.

All agents were intravenously administered as a single bolus injection through a lateral tail vein with a 1 ml syringe fitted with a 27 gauge, ½ inch needle. Prior to administration, the stock solutions of nBT062 antibody, nBT062-SPDB-DM4 and nBT062-SPP-DM1 were diluted with sterile PBS to concentrations of 2 mg/ml, 28.1 μg/ml and 28.1 μg/ml, respectively, so that the injected volume for each mouse was between 120-220 μl.

Part II

In a second set of experiments, MOLP-8 cells ($1.5 \times 10^7$ cells per mouse), suspended in a 50:50 mixture of serum free media and matrigel were injected subcutaneously in the area under the right shoulder in 100 μl. Tumor volumes reached about 80 mm³ at day 11 and the mean of the controls was about 750 mm³ at day 25, post cell inoculation. The tumor doubling time was estimated to be 4.58 days. Each mouse in the control group (n=6) received 0.2 ml of sterile PBS administered into the lateral tail vein (i.v.) in a bolus injection. All treatment doses were based on conjugated maytansinoid. Nine groups (n=6) were treated with a single intravenous injection of nBT062-SMCC-DM1, nBT062-SPDB-DM4, or nBT062-SPP-DM1, each at doses of 450, 250 and 100 μg/kg. An additional group (n=6) received 250 μg/kg nBT062-SMCC-DM1 in a repeated dosing (weekly for five weeks). Mice were randomized into eleven groups (n=6) by tumor volume using the LabCat Program. The tumor volumes ranged from 40.0 to 152.5 mm³. The mice were dosed based on the individual body weight.

Tumor size was measured twice per week in three dimensions using the LabCat System (Tumor Measurement and Tracking, Innovative Programming Associated, Inc., Princeton, N.J.). The tumor volume in mm³ was calculated using the methodology described in Tomayko et al., Cancer Chemother. Pharmacol, 24 (1989), 148:

$$\text{Volume} = \text{Length} \times \text{Width} \times \text{Height} \times \frac{1}{2}$$

$\text{Log}_{10}$ cell kill was calculated with the formula described in Bissery et al., Cancer Res., 51 (1991), 4845:

$$\text{Log}_{10} \text{ cell kill} = (T-C)/T_d \times 3.32$$

where (T−C) or tumor growth delay, is the median time in days required for the treatment group (T) and the control group (C) tumors, to reach a predetermined size (600 mm³). $T_d$ is the tumor doubling time, based on the median tumor volume in the control mice, and 3.32 is the number of cell doublings per log of cell growth.

Results

Figure 10:
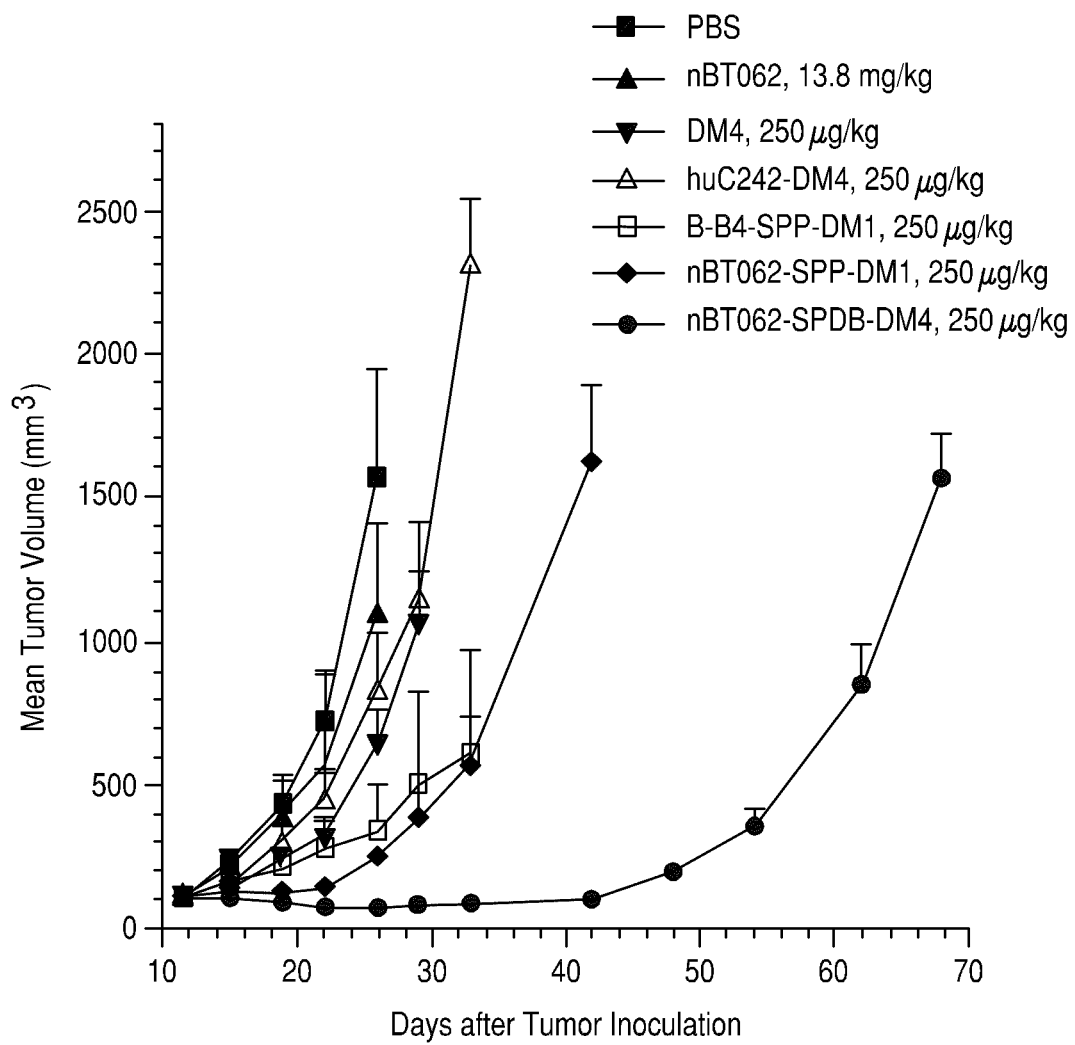
FIG. 10 depicts mean tumor volume (+/−SD) of MOLP-8 human multiple myeloma xenografts in CB.17 SCID mice over time (days) post-inoculation.

The tumor growth in individual mice is shown in FIGS. 8 and 9. The mean (+/−SD) tumor growth for each group is shown in FIG. 10.

As compared with tumor growth in the PBS-treated animals, treatment with nBT062 antibody, unconjugated free DM4 or the irrelevant non-targeting conjugate huC242-DM4 did not cause any significant inhibition of tumor growth.

All three CD138-targeting conjugates, nBT062-SPDB-DM4, B-B4-SPP-DM1 and nBT062-SPP-DM1, at a dose of 250 μg/kg caused marked delay in tumor growth. Based on the mean tumor volumes measured in the treatment groups, the DM4 conjugate nBT062-SPDB-DM4 was the most active one, while the nBT062-SPP-DM1 conjugate showed slightly increased activity as compared to its murine counterpart B-B4-SPP-DM1 (FIG. 10). The results obtained in individual mice show in addition that the anti-tumor activity obtained with B-B4-SPP-DM1 is more heterogeneously and therefore less predicable than that measure in mice treated with nBT062-SPP-DM1. In terms of homogeneity of anti tumor activity, the other conjugate that uses nBT062 as targeting antibody nBT062-SPDB-DM4 behaved similar to nBT062-SPP-DM1.

No body weight reduction was observed in any treatment group suggesting that the treatments were well tolerated.

Discussion

The results of the analysis of three CD138-targeting conjugates in experimental animals demonstrate the importance of targeted delivery for the anti-tumor activity. While the maytansinoid conjugates of the human chimeric nBT062 and the murine B-B4 antibodies show significant activity as measured by log cell kill, there was no significant impact on tumor growth from treatment with unconjugated DM4, unmodified native huBT062 antibody, or a non-targeting control conjugate (huC242-DM4).

The immunoconjugate prepared from the human chimeric antibody, nBT062-SPP-DM1, gave slightly higher anti-tumor activity then the conjugate prepared from its murine counterpart, B-B4-SPP-DM1. In addition, treatment with nBT062-SPP-DM1 and nBT062-SPDB-DM4 resulted in more homogenous responses in individual mice as compared to treatment with B-B4-SPP-DM1. The high binding variation of B-B4-SPP-DM1 explained that the measurement of the median tumor volume (+/−SD) of MOLP-8 human multiple myeloma xenografts in CB.17 SCID mice over time (days) post-inoculation actually provided for relatively better results for B-B4-SPP-DM1 than for nBT062-SPP-DM1 (data not shown). This feature of immunoconjugates using nBT062 as a targeting antibody seems to be beneficial especially for therapeutic use of the conjugates.

Lastly, the most potent of the maytansinoid conjugates, following single iv administration in the MOLP-8 xenograft models in SCID mice, was nBT062-SPDB-DM4.

Bystander Killing (Cell Viability Assay)

CD138⁺ OPM2 cells and CD138⁻ Namalwa cells were seeded in round bottom plates either in separate wells or in coculture. The cells were treated with nBT062-SPDB-DM4 at concentrations ranging from $1 \times 10^{-8}$ to $1 \times 10^{-9}$ M. The fraction of viable cells was detected using WST reagent (water-soluble tetrazolium salt, ROCHE) according to the manufacturer's instruction (ROCHE). The fraction of surviving cells was calculated based on the optical densities measured in a microplate reader using standard procedures.

Discussion

Figure 13:
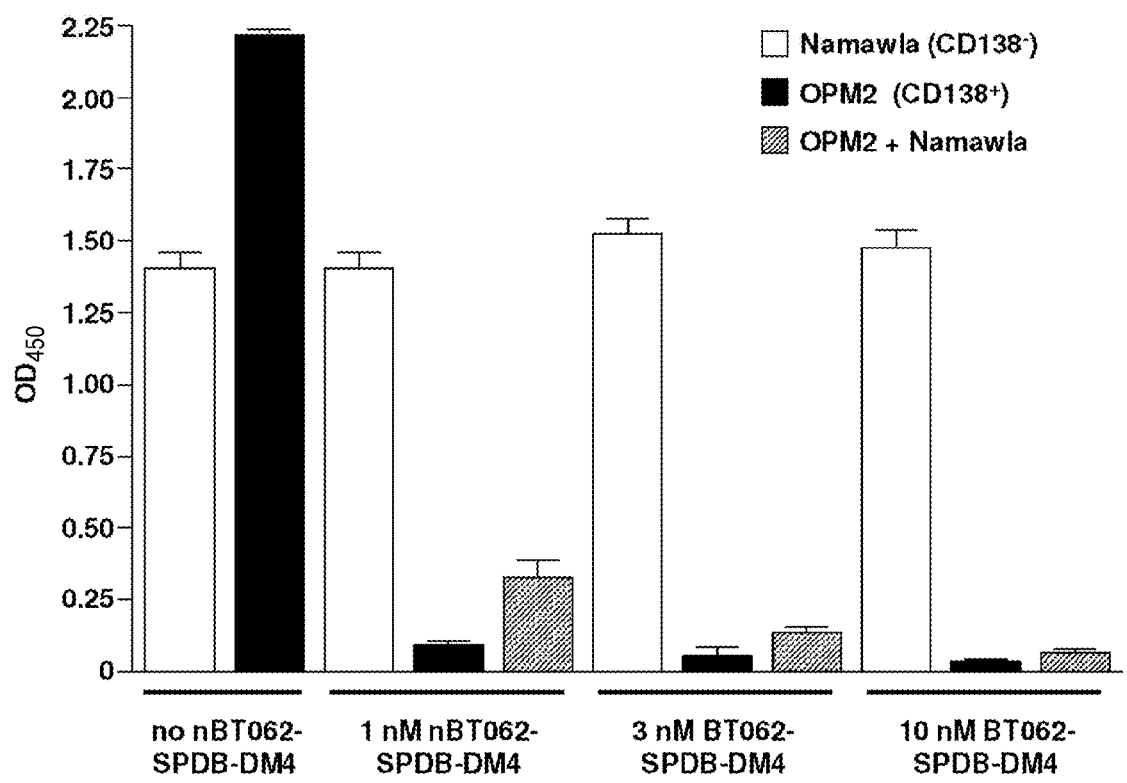
FIG. 13 shows nBT062-SPDB-DM4 mediated bystander killing in vitro. CD138 positive OPM2 cells and CD138 negative Namawla cells were cultured with nBT062-SPDB-DM4 at different concentrations and cell viablility was measured. $OD_{450}$ values represent a measure for cell viability.

Bystander killing of non-target cells in close proximity (as present in round bottom wells) to multiple myeloma cells upon nBT062-SPDB-DM4 treatment was analysed in an in vitro study in which CD138-positive OPM2 cells were cultured in coculture with CD138-negative Namawla cells (FIG. 13). Generally, while CD138-positive cells are efficiently killed by nBT062-SPDB-DM4, CD138-negative cells were not affected by the conjugate. In the coculture in round bottom wells, however, nBT062-SPDB-DM4 also killed the antigen-negative cells in close proximity to the antigen-positive cells (an effect that is often referred to as bystander killing). Kovtun et al. (2006) discussed that bystander killing mediated by maytansinoid conjugates occurs only in close proximity to antigen-positive cells. Kovtun et al. (2006), which is incorporated herein by reference in its entirety, also discusses the importance of the linker of the immunoconjugate. In vivo, bystander killing may contribute to 1) the eradication of tumour cells that heterogeneously express CD138, 2) the destruction of the tumour microenvironment by the killing of tumour stroma cells, and 3) the prevention of the selection of CD138-negative nBT062-SPDB-DM4-resistant cells.

The bystander effect is of particular importance if the activity of an immunoconjugate is impaired by a target antigen that is expressed in tumors in a heterogeneous fashion. If this is the case, a particular cell of a tumor expresses, if at all, the antigen not in amount that would allow effective direct targeting and killing of said cell by the respective immunoconjugate. The anti-tumor efficacy of nBT062-SPDB-DM4 on CD138-negative cells in coculture with CD138-positive cells clarified that the presence of target cells influences, under the appropriate circumstances, the cytotoxic activity of nBT062-SPDB-DM4 towards non-target cells.

Xenograft Mouse Experiments B

In this set of experiments, eighty-five mice were inoculated with MOLP-8 cells ($1.5 \times 10^7$ cells/mouse) subcutaneously in the right shoulder. Tumor take rate was 100%. Sixty-six SCID mice bearing bulky MOLP-8 tumors with a mean tumor volume of about 80 mm$^3$ were randomized into eleven treatment groups (n=6). Mice were treated with a single dose of one of three conjugates (nBT062-SMCC-DM1, nBT062-SPDB-DM4 or nBT062-SPP-DM1). An additional group received five weekly doses of nBT062-SMCC-DM1 and a control group received a single dose of PBS. Mean tumor volumes are shown in FIG. 11A. A dose response was established for each conjugate. A median tumor volume of 750 mm$^3$ in the PBS-treated animals was reached on day 25. Tumor doubling time determined by the best-fit linear regression curve fit on a log-linear plot of control tumor growth was 4.58 days. Animals treated with nBT062-SPDB-DM4 at 450 µg/kg had the highest log cell kill (LCK=2.89), followed by animals treated with nBT062-SMCC-DM1 at 250 µg/kg weekly dosing (LCK=2.1; see Table 5). Comparison of the mean tumor growth curves for the treatment groups by repeated measures ANOVA performing Dunnett's Multiple Comparison Test showed a significant difference between the PBS control group and 450 µg/kg nBT062-SPDB-DM4 ($p<0.01$), 250 µg/kg nBT062-SPDB-DM4 ($p<0.05$) and five weekly doses of 250 µg/kg nBT062-SMCC-DM1 ($p<0.05$). No partial or complete tumor regression in any of the treatment groups occurred with the exception of one animal receiving 450 µg/kg nBT062-SPDB-DM4, which had partial regression of the tumor until day 85 post-inoculation.

TABLE 5

Log cell kill (LCK) values as measure for anti-tumor activity of different nBT062-DMx conjugates in different dosing schemes. Refer to the Materials and methods section for information on calculation of LCK values.

| Test Material | Dose (µg/kg) | LCK | Dosing |
|---|---|---|---|
| PBS | | | single dose |
| nBT062-SMCC-DM1 | 450 | 0.85 | single dose |
| nBT062-SMCC-DM1 | 250 | 0.53 | single dose |
| nBT062-SMCC-DM1 | 100 | 0 | single dose |
| nBT062-SPDB-DM4 | 450 | 2.89 | single dose |
| nBT062-SPDB-DM4 | 250 | 1.05 | single dose |
| nBT062-SPDB-DM4 | 100 | 0.39 | single dose |
| nBT062-SPP-DM1 | 450 | 0.8 | single dose |
| nBT062-SPP-DM1 | 250 | 0.39 | single dose |
| nBT062-SPP-DM1 | 100 | 0.2 | single dose |
| nBT062-SMCC-DM1 | 250 | 2.1 | weekly for 5 weeks |

In Vivo Efficacy of nBT062-SPDB-DM4 and nBT062-SPP-DM1 in the Bone Marrow Environment
Preparation of SCID Mice Having Human Fetal Bone Implants Human fetal long bones (human fetal bone chips) were implanted into the upper body of CB17 SCID-mice (SCID-hu) as previously described (Urashima et al., 1997) and thus provided for a model in mouse for the homing of human MM cells to human BM cells.

Treatment Regime (SCID-hu/INA-6 mice)

4 weeks following bone implantation, $2.5 \times 10^6$ INA-6 cells in a final volume of 100 µL RPMI-1640 cell culture medium were injected directly into the human bone marrow cavity in the SCID-hu mice described above. An increase in the levels of soluble human IL-6 receptor (shuIL-6R), which is released by INA-6 cells, was used as a parameter of MM cell growth and disease burden.

Mice developed measurable serum shuIL-6R approximately 4 weeks following INA-6 cell injection and then received 0.176 mg conjugate or vehicle control via tail vein injection weekly for 7 weeks. After each treatment, blood samples were collected and measured for shuIL-6R levels by an enzyme-linked immunosorbent assay (ELISA, R&D Systems, Minneapolis, Minn.). The results are depicted in FIG. 12.

Discussion

Interleukin 6 (IL-6) is a growth and survival factor for multiple myeloma cells. INA-6 is an IL-6-dependent human myeloma cell line, which also requires bone marrow stromal cells (BMSC) to proliferate. INA-6 cell lines produce soluble IL-6 receptor (shuIL-6R). An increase in the levels of shuIL-6R can be used as a parameter of MM cell growth and disease burden.

Thus, the sCID-hu/INA-6 mice provide a model for multiple myeloma cells growing in their normal bone marrow environment. The tumor cells of this model, which directly interact with the human bone marrow, closely resemble the situation in patients, in which tumor cell growth is also promoted by the presence of stromal cells. As INA-6 cells release soluble human interleukin-6 receptor (shuIL-6R), serum concentrations of this protein can be used as a measure for tumor cell load in these mice. The in vivo potency of nBT062-SPDB-DM4 and nBT062-SPP-DM1 were tested in this environment.

Treatment of SCIDhu/INA-6 mice with weekly i.v. administrations of nBT062-SPDB-DM4 or nBT062-SPP-DM1 for seven weeks induced efficient tumour regression, as detected by a decrease in serum shuIL-6R levels relative to the control, indicating good efficacy of the conjugates even in the environment of human bone marrow, which reflect the relevant situation in patients (FIG. 12).

Analysis of the Efficacy of nBT062-SMCC-DM1, nBT062-SPDB-DM4 and nBT062-SPP-DM1 in Vitro and in Experimental Animals in Vivo.

Materials and Methods
Cell Culture

Dex-sensitive (MM.1 S) and resistant (MM.1 R) human MM cell lines were kindly provided by Dr. Steven Rosen (Northwestern University, Chicago, Ill.). RPM18226 and U266 human MM cell lines were obtained from American Type Culture Collection (Manassas, Va.). Doxorubicin (Dox)-resistant (RPMI-Dox40) and Melphalan-resistant (LR5) cells were kindly provided by Dr. William Dalton (Lee Moffitt Cancer Center, Tampa, Fla.). OPM1 and OPM2 plasma cell leukemia cells were kindly provided by Dr. Edward Thompson (University of Texas Medical Branch, Galveston).

All MM and bone marrow (BM) stroma cell lines were cultured in Dulbecco's modification of Eagle's medium DMEM (Sigma) containing 10% fetal bovine serum, 2 mM L-glutamine (Life Technologies), 100 U/mL penicillin and 100 Ag/mL streptomycin (Life Technologies). Blood samples collected from healthy volunteers were processed by Ficoll Paque gradients to obtain peripheral blood mononuclear cells (PBMCs). Patient-derived MM and BM cells were obtained from BM samples after informed consent was obtained per the Declaration of Helsinki and approval by the Institutional Review Board of the Dana-Farber Cancer Institute (Boston, Mass.). BM mononuclear cells were separated using Ficoll Paque density sedimentation, and plasma cells were purified (>95% $CD138^+$) by positive selection with anti-CD138 magnetic activated cell separation micro beads (Miltenyi Biotec Auburn, Calif.). Tumor cells were purified from the BM of patients with MM using the RosetteSep negative selection system (StemCell Technologies, Vancouver, BC, Canada), as described previously (Hideshima, 2001). RosetteSep antibody cocktail was given to Bone marrow samples. CD138 negative cells were crosslinked to red blood cells (rosetted) with RosetteSep reagents, and incubated for 20 minutes at room temperature, prior to separation by Ficoll density centrifugation.

Growth Inhibition and Proliferation Assay

The growth inhibitory effect of nBT062-SMCC-DM1, nBT062-SPDB-DM4, nBT062-SPP-DM1 and Dexamethasone on growth of MM cell lines, PBMCs, and BMSCs was assessed in MTT-assays by measuring 3-(4,5-dimethylthiazol-2-yl)2,5-diphenyl tetra-sodium bromide (MTT; Chemicon International, Temecula, Calif.) dye metabolization, as described previously (Hideshima, 2003).

Effect of nBT062-SMCC-DM1, nBT062-SPDB-DM4 and nBT062-SPP-DM1 on MM Cell Growth in the BM To evaluate the growth stimulatory effect of BM cells on the sensitivity of MM cells towards immunoconjugates, MM cells ($2 \times 10^4$ cells/well) were co-cultured for 48 h with bone marrow stromal cells (BMSCs, $1 \times 10^4$ cells/well) in 96-well plates (Costar, Cambridge, Mass.), in the presence or absence of drug. DNA synthesis was measured by [3H]-thymidine (Perkin-Elmer, Boston, Mass.) uptake. [3H]-thymidine (0.5 µCi/well) was added during the last 8 hours of the experiment. All experiments were performed in quadruplicates.

Cell Cycle Analysis

MM cells ($1 \times 10^6$ cells) were incubated for 48 hours in presence or absence of immunoconjugates, washed with phosphate-buffered saline (PBS), permeabilized by a 30-minute exposure to 70% ethanol at −20° C., incubated with propidium iodide (PI) (50 µg/mL) in 0.5 mL PBS containing 20 U/mL RNAse A (Roche Diagnostics) for 30 minutes at room temperature. DNA-content was analyzed using a flow cytometer.

Immunofluorescence

Cells grown on glass cover slips were fixed in cold absolute acetone for 10 min, washed in PBS and blocked for 60 min with 5% FBS in PBS. Slides were then incubated with anti-CD138 antibody (sc12765, Santa Cruz Biotechnology, Santa Cruz, Calif.) for 24 h at 4° C. Cells were again washed with PBS and incubated with fluorescence labeled goat anti-mouse IgG for 1 h at 4° C. and analyzed using a Nikon E800 fluorescence microscope as described previously (Ikeda, 2005; Kiziltepe, 2007).

Auto Fluorescent Green Fluorescent Protein-Positive (GFP) Human Mm Xenograft Model and Human MM Xenograft Murine Model.

OPM1 cells were transfected with green fluorescent protein ($OPM1^{GFP}$) using a lentiviral vector, as previously described (Zufferey, 1998). CB17 SCID mice (48-54 days old) were purchased from Charles River Laboratories (Wilmington, Mass.). All animal studies were conducted according to protocols approved by the Animal Ethics Committee of the Dana-Farber Cancer Institute. The mice were inoculated subcutaneously in the right flank with $5 \times 10^6$ $OPM1^{GFP}$ MM cells in 100 µl RPMI-1640. When tumors were palpable, mice were assigned into the treatment group receiving 176 µg/mouse based on the molecular weight of the conjugate, once weekly for 4 weeks by lateral tail vein injection, and 5 mice were assigned into the control group receiving vehicle alone. Caliper measurements of the longest perpendicular tumor diameters were performed every other day to estimate the tumor volume using the following formula representing the 3D volume of an ellipse: $4/3 \times (width/2)^2 \times (length/2)$. Animals were killed when tumor reached 2 cm or if the mice appeared moribund. Survival was evaluated from the first day of treatment until death. Tumor growth was evaluated using caliper measurements from the first day of treatment until day of killing which was day 10 for control and day 21 for the BT062-SPDB-DM4 treatment group. Mice were monitored by whole-body fluorescence imaging using a Illumatool Bright Light System LT-9900 (Lightools Research, Encinitas, Calif.), following a cutaneous shave of the tumor area. Images were captured with a canon IXY digital 700 camera. Ex vivo analysis of tumor images were captured with a LEICA DM IL microscope connected to a LEICA DFC300 FX camera at 40 u/0.60 (Leica, Heidelberg, Germany).

Detection of Apoptotic Cells

MM cells ($1 \times 10^6$) were washed with PBS and incubated in the presence or absence of immunoconjugates. Apoptotic cells were stained with PE-conjugated Apo 2.7 antibody (7A6, Beckman Coulter, Inc.). The cells were analyzed by flow-cytometry on an Epics flow cytometer (Beckman Coulter, Inc.) using the on RXP Cytomics software.

Western Blotting

MM cells were cultured in the presence or absence of nBT062-SMCC-DM1, nBT062-SPDB-DM1 or BT062-SPP-DM1, harvested, washed and lysed using radioimmuno precipitation assay (RIPA) buffer containing 2 mM $Na_3VO_4$, 5 mM NaF, 1 mM phenylmethylsulfonyl fluoride, 5 mg/ml Complete protease inhibitor, as described previously (Yasui, 2005; Hayashi, 2002). Whole-cell lysates (20 µg per lane) were subjected to sodium dodecyl sulfate-polyacrylamide gel electrophoresis (SDS-PAGE) separation, transferred to Pure Nitrocellulose membranes (Bio-Rad Laboratories, Hercules, Calif.) and immunoblotted with antibodies against poly-ADP (adenosine diphosphate)-ribose polymerase (PARP), caspase-8, caspase-3, caspase-9, AKT, and phospho (Ser 473) Akt (Cell Signaling), as well as anti-tubulin and anti-CD138 antibodies (Santa Cruz Biotechnology).

Cell Adhesion Assay

In a 96-well plate, $1 \times 10^4$ BMSCs were pipetted into each well and incubated for 12 h in the presence or absence of immunoconjugates at 37° C. Upon that incubation, MM cells in the presence or absence of drugs were given to the BMSCs. Therefore, MM cells were washed 3 times with PBS and resuspended in serum-free RPMI medium at cell densities of $2 \times 10^5$ cells in 100 µL in the presence or absence of drugs. Each sample group was run in either triplicate or quadruplicate. After 2 hours in coculture at 37° C., nonadherent, weakly adhered cells and medium were removed by inverting the plate. Subsequently, the wells were washed three times with PBS. The remaining adherent cells were cultured in 10% FBS in RPMI medium in the presence of [3H]-thymidine (0.5 µCi/well, Perkin Elmer, Boston, Mass., USA) for further 8 hours, to measure DNA synthesis.

Statistical Analysis

Statistical significance of differences observed in immunoconjugate (IC)-treated versus control cultures was determined using the Dunn's multiple comparison tests. The minimal level of significance was a P value less than 0.5. For in vivo experiments, tumor volumes were compared using 1-way analysis of Dunn's multiple comparison tests. Survival was assessed using Kaplan-Meier curves and log-rank analysis.

Results

Expression of CD138 on MM Cell Lines

Figure 14A:
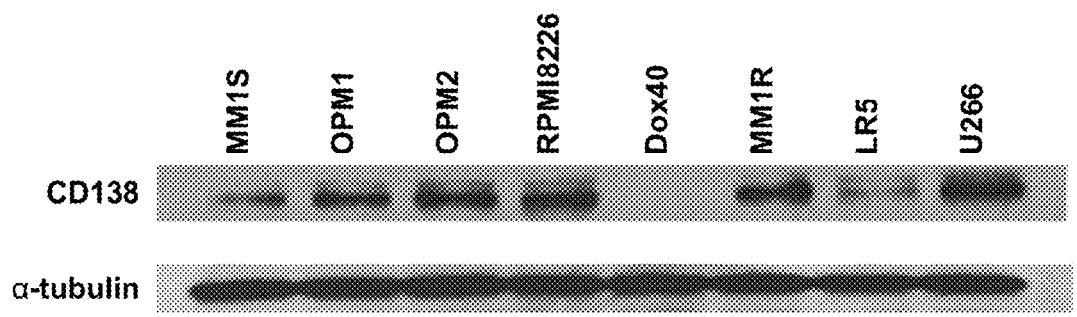
FIG. 14 shows in (A) CD138 expression by different MM cells and in (B) a microscopic analysis of DOX40 cells (upper panel) and OPM1 cells (lower panel). CD138 expression is shown at the right hand side, nucleic acids is shown on the left hand side.

The expression levels of CD138 in multiple myeloma cell lines by Western blotting using whole cell lysates of MM1S, OPM1, OPM2, RPM18226, DOX40, MM1R, LR5, and U266 cells were analyzed (FIG. 14A)

As can be seen in FIG. 14A, MM1S and LR5 showed week expression of CD138 and Dox40 cells are CD138 negative. The other cell lines showed high expression levels of CD138. It was shown that CD138 is expressed in 7 out of 8 (87.5%) multiple myeloma cell lines.

Figure 14B:
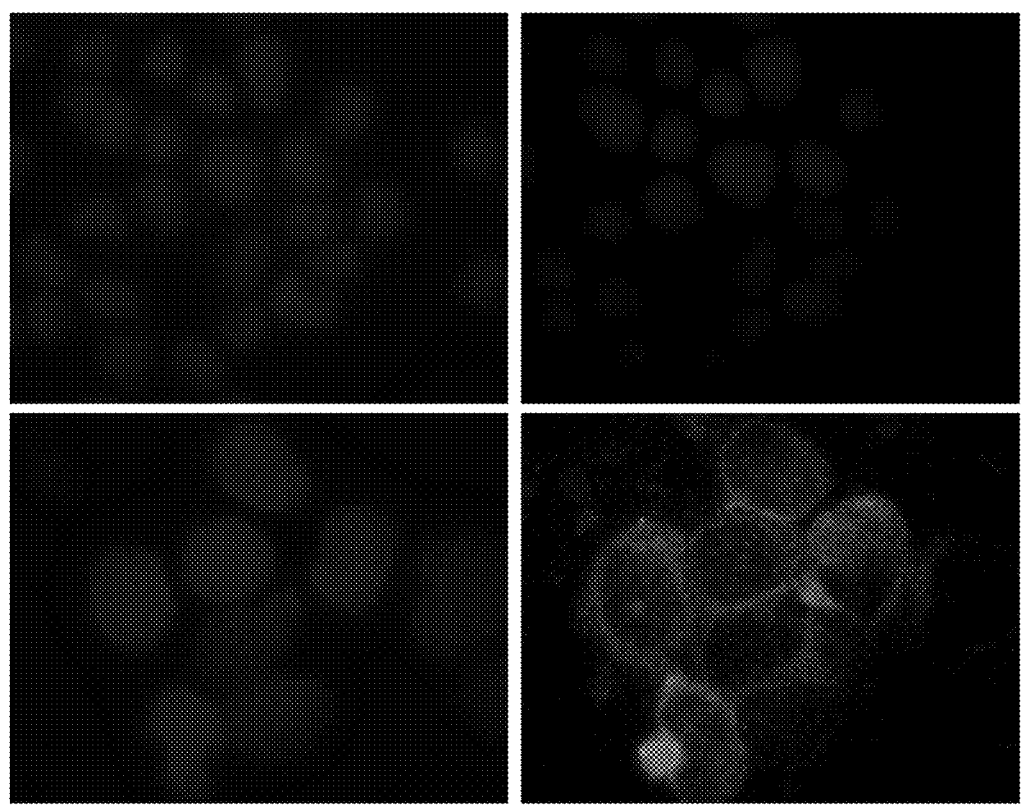
Figure 15A:
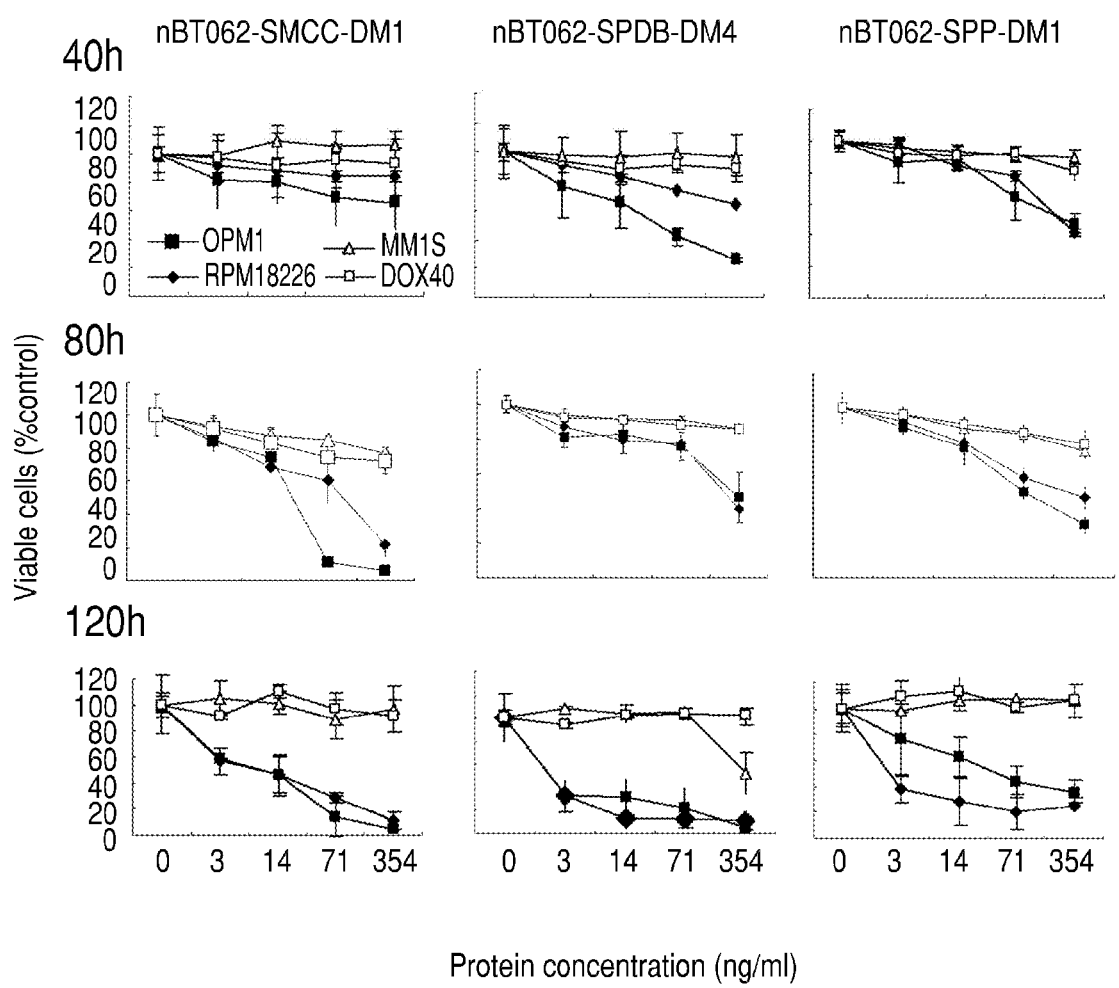
FIG. 15 (A) depicts the cytotoxicity of nBT062-SMCC-DM1, nBT062-SPDB-DM4 and nBT062-SPP-DM1 towards MM cells after 40, 80 and 120 hours.
Figure 15B:
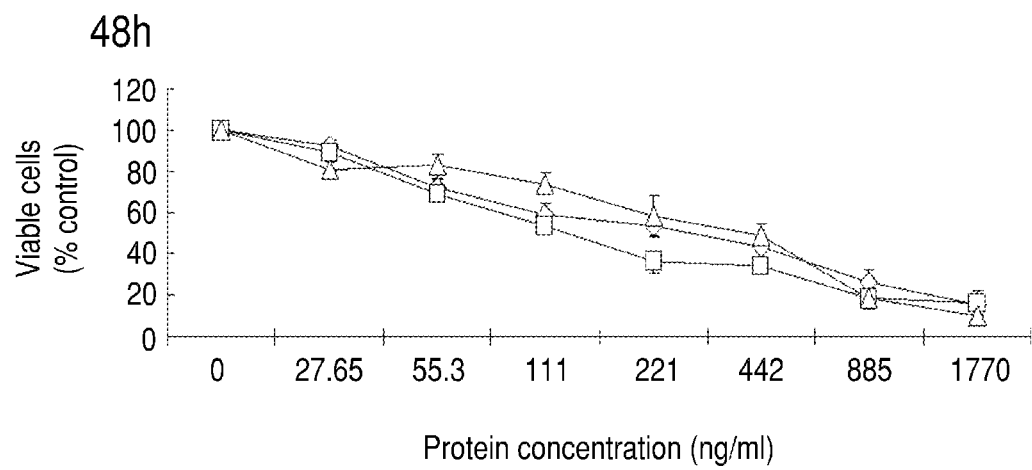
Figure 15C:
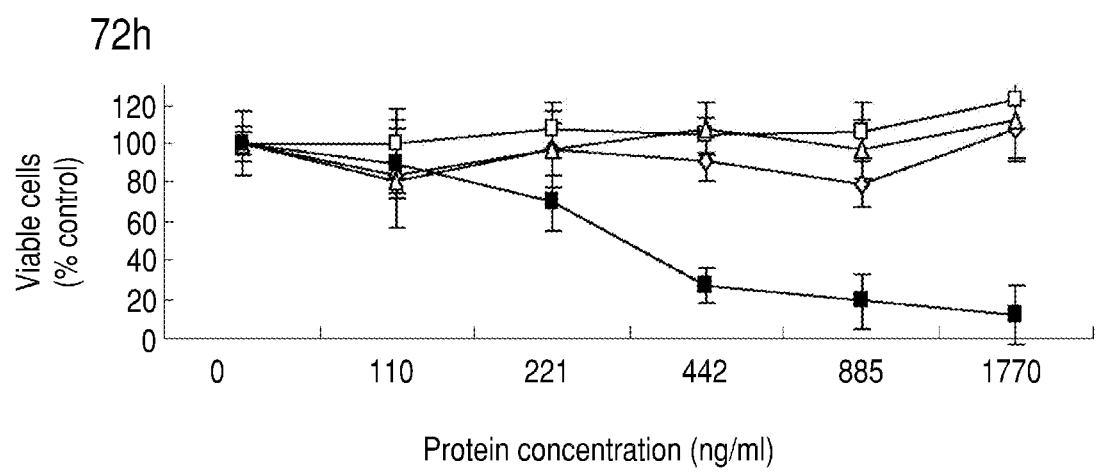

FIG. 14B shows an analysis using immunofluorescence staining using CD138 specific antibodies. Microscopic analysis of DOX40 cells (upper panel) and OPM1 cells (lower panel) was performed. CD138 expression is shown on the left and nucleic acids on the right. FIG. 14B shows that DOX40 cells display almost no detectable expression of CD138. In contrast, OPM1 cells showed high CD138 immunoreactivity.

nBT062-SMCC-DM1, nBT062-SPDB-DM4 and nBT062-SPP-DM1 Show Selective Cytotoxicity to CD138 Positive Cell Lines The efficacy of CD138 antibody maytansinoid conjugates were also tested in cell viability assays. The immunoconjugates nBT062-SMCC-DM1, nBT062-SPDB-DM4 and nBT062-SPP-DM1 were assayed for their cytotoxic potency against CD138-positive cells (OPM1, RPM18226), CD138 weakly expressing cells (MM1S) and CD138-negative cells (DOX40), using a 3-(4,5-dimethylthiazol-2-yl)-2,5diphenyltetrazolium bromide (MTT)-based assay. FIG. 15A depicts OPM1 (■), RPM18226 (♦), DOX40 (□) and MM1S cells (Δ) as exposed to nBT062-SMCC-DM1, nBT062-SPDB-DM4 or nBT062-SPP-DM1, respectively. Cell survival was measured in MTT assays. Cell viabilities after indicated incubation times (40, 80, 120 h) are given in % of viability of untreated controls. Treatment of the cells with nBT062-SMCC-DM1, nBT062-SPDB-DM4 and nBT062-SPP-DM1 at concentrations ranging from 3 to 354 ng/ml induced growth inhibition in CD138 positive cells. This effect occurred in a time and dose dependent manner and was most prominent after 120 h in the two cell lines expressing high levels of CD138. Under the same conditions, almost no cytotoxicity could be measured against CD138 negative DOX40 cells (FIG. 15A). Importantly, the three immunoconjugates were also cytotoxic against patient-derived negative selected MM cells as analyzed in a concentration range of 111-442 ng/ml, measured after an incubation time of 48 h (FIG. 15B). FIG. 15C shows PBMCs derived from 3 healthy subjects that were cultured with nBT062-SPDB-DM4 for 72 h before cell viability was determined. Cell viability of OPM1 mM treated under the same conditions is shown as a control (closed squares). As can be seen from FIG. 13 15C, the immunoconjugates did not induce cytotoxic effects in PBMCs (Peripheral Blood Mononuclear Cells) isolated from 3 healthy volunteers (FIG. 15C). These results demonstrate that nBT062-SMCC-DM1, nBT062-SPDB-DM4 and nBT062-SPP-DM1 selectively kill CD138-positive MM cells (All data shown in this figure represent averages of triplicates. Standard deviations are indicated by error bars).

nBT062-SMCC-DM1, nBT062-SPDB-DM4 and nBT062-SPP-DM1 Induce G2/M Cell Cycle Arrest in OPM1 Cells As maytansinoid acts by suppressing microtubule polymerization, it has previously been shown that DM1 and DM4 induces G2/M cell cycle arrest in tumor cells (Erickson, 2006). Thus, the cell cycle profile of OPM1 cells were examined after treatment with nBT062-SMCC-DM1, nBT062-SPDB-DM4 and nBT062-SPP-DM1. Cells were incubated with the immunoconjugates for 0 to 72 hours, labeled with PI, and analyzed by flow-cytometry. FIG. 16A shows OPM1 cells treated with immunoconjugates for 0, 12 or 24 h and the analysis of cell cycle profiles by PI staining. As can be seen from FIG. 16A, these compounds had significant effects on the proportion of cells in G2/M-phase as compared to untreated cells. Exposure of OPM1 cells to nBT062-SPDB-DM4 induced a quicker and stronger response compared to cells treated with the other two drugs.

nBT062-SPDB-DM4 Induces Apoptosis in OPM1 Cells

Next, it was determined whether nBT062-SPDB-DM4 induces apoptosis in target cells. FIG. 16B shows OPM1 cells cultured in the presence or absence of immunoconjugates for 24, 48 or 72 h. The percentage of apoptotic cells was assessed by Apo 2.7 antibody staining and flow-cytometric analysis. As shown in FIG. 16B, the staining of the cells with the Apo2.7 antibody demonstrated apoptosis induction of cells treated with the immunoconjugates.

Figure 16C:
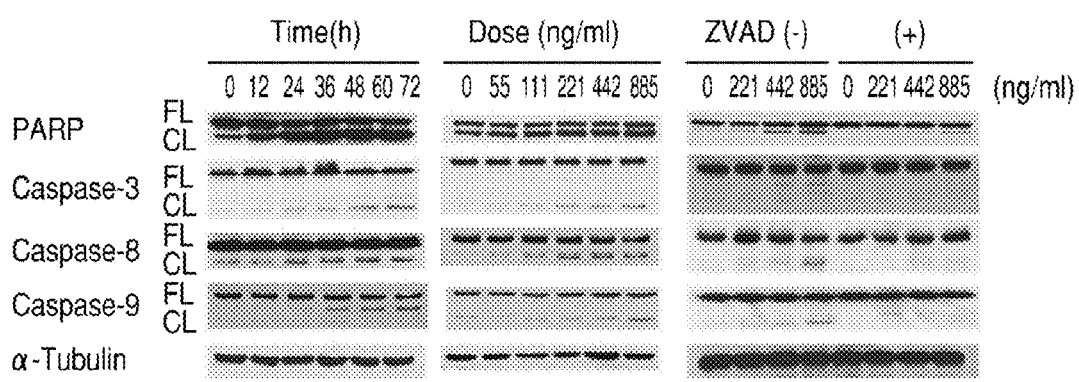
FIG. 16 (A) shows a cell cycle analysis in which OPM1 cells were treated with immunoconjugates for 0, 12 or 24 h and cell cycle profiles were analyzed by PI staining.

FIG. 16C shows OPM1 cells cultured in the presence of 885 µg/ml nBT062-SPDB-DM4 for the indicated times (left panel) or with different concentrations of immunoconjugate (middle panel). In this Figure, FL indicates bands corresponding to full-length forms of caspases and PARP; CL indicates bands corresponding to the cleavage products. OPM1 cells were pre-incubated with zVAD-fmk (50 µmol/L) for 60 minutes prior to treatment with nBT062-SPDB-DM4 for 24 h at indicated doses. Total cell lysates were subjected to immunoblotting using caspase-3, -8, -9, PARP, and tubulin specific antibodies. As can be seen from FIG. 16C, treatment of OPM1 cells with nBT062-SPDB-DM4 induced cleavage of caspase-8, -9, and -3 and PARP in a dose and time-dependent fashion (left and middle panel). The pan-caspase inhibitor zVAD-fmk blocked nBT062-SPDB-DM4 induced caspase-3, -8, -9 and PARP cleavage in OPM1 cells (FIG. 16C, right panel). These results indicate that nBT062-SPDB-DM4 activates caspases and induces apoptosis in target cells.

nBT062-SMCC-DM1, nBT062-SPDB-DM4 and nBT062-SPP-DM1 Inhibit the Protective Effect Of BMSCs In multiple myeloma patients, the bone marrow microenvironment induces growth, survival, and drug resistance in MM cells via at least two different mechanisms: adhesion of MM cells to fibronectin confers cell adhesion-mediated drug resistance (CAM-DR); and cytokines as interleukin-6 (IL-6) and insulin like growth factor 1 (IGF-1) in the bone marrow milieu induce important signalling cascades that finally mediate MM cell resistance to conventional therapeutics. Cytotoxicity of the immunoconjugates towards MM cells in co-culture with BMSCs was analyzed in the presence of IL-6 or IL-6 or in the presence of bone marrow stromal cells (BMSCs).

In FIGS. 17A to 17C, OPM1 cells were cultured for 48 h with control media (black bars) or with increasing concentrations of nBT062-SPDB-DM4: 55 ng/ml (dark gray bars; *), 111 ng/ml (gray bars; ), 221 ng/ml (light gray bars; *), 442 ng/ml (very light gray bars; **) 885 ng/ml (white bars; ***). Cells in FIG. 17D were treated for 72 h with control media (black bars) or with increasing concentrations of Dexamethasone: 250 nM (grey bars: +), 500 nM (light grey bars; ++), 1000 nM (white bars; +++). IL-6 was present in some cultures at concentrations of 1 or 10 ng/ml (FIG. 17A). IGF-1 was used at concentrations of 10 or 50 ng/ml (FIG. 17B). None of these cytokines induced resistance of the cells towards the immunoconjugates.

To analyze the influence of the BM microenvironment on growth and resistance of OPM1 towards the immunoconjugates, cells were cultured in the presence or absence of BMSCs as described above.

Figure 17:
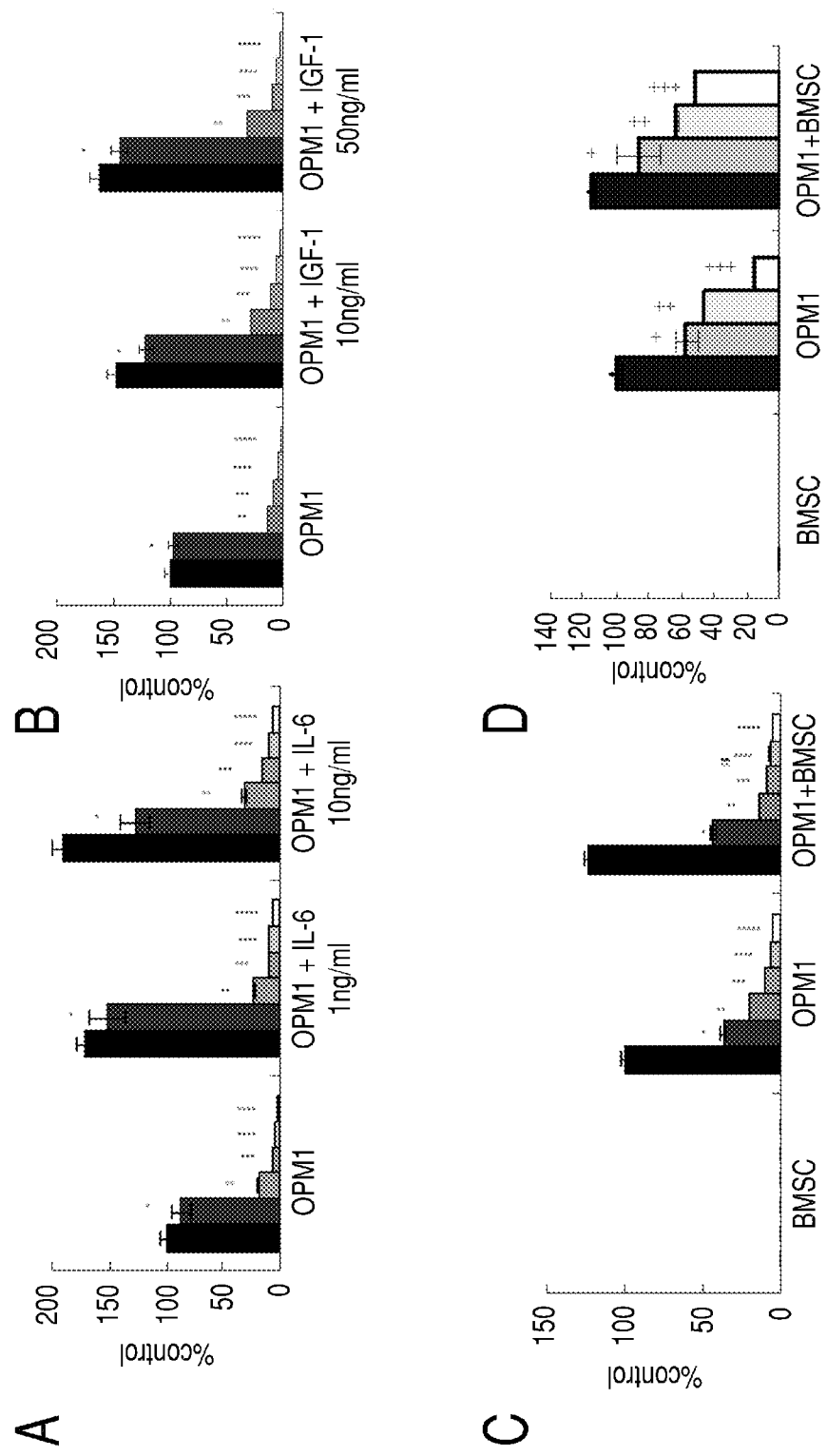
FIG. 17 shows in (A) to (C) the effect of IL-6, IGF-1 and BMSCs on growth and sensitivity of MM cells towards the immunoconjugates.
Figure 17E:
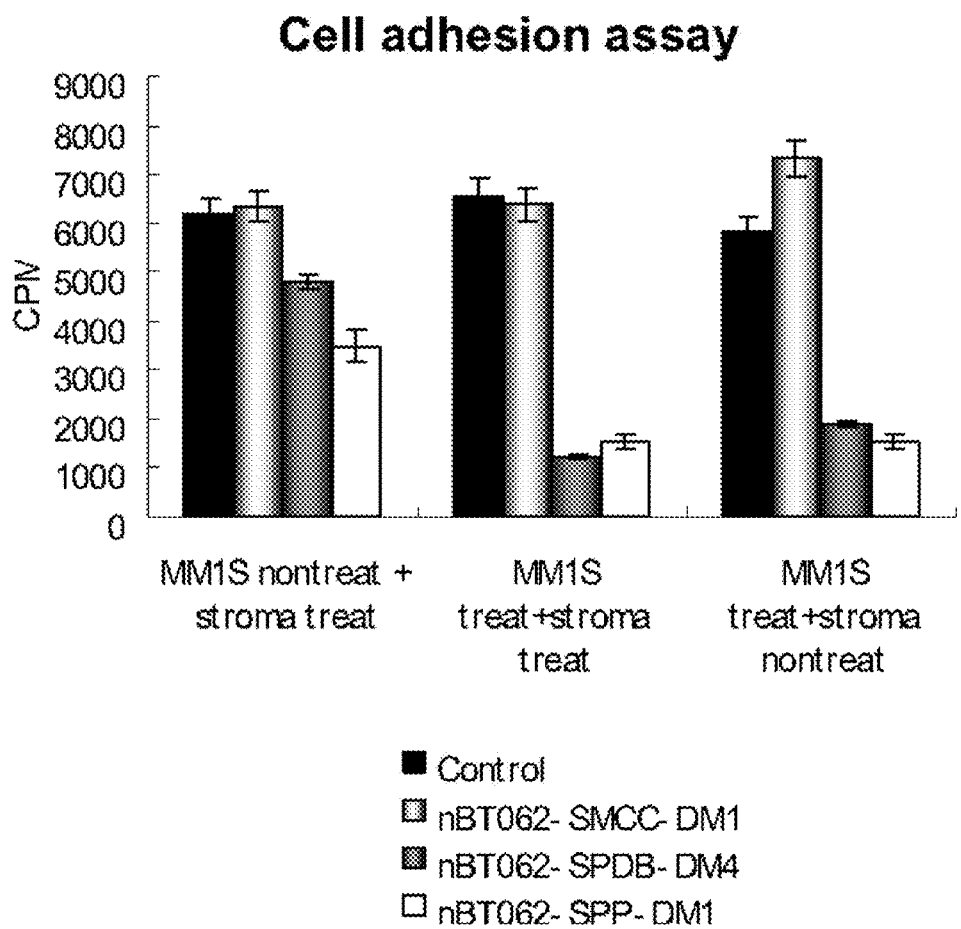

Coculturing of OPM1 cells in the presence or absence of BMSCs is shown in panel (C) and (D) of FIG. 17. In all experiments, DNA synthesis was determined by measuring [3H]-thymidine incorporation during the last 8 h of culture. Adherence of OPM1 cells to BMSCs triggered increased [3H]-thymidine uptake. Importantly, cytotoxicity of the immunoconjugates was not affected by the presence of BMSCs (FIG. 17C). In contrast, Dexamethasone, which was included as a control, was not able to overcome the BMSC triggered protective effect (FIG. 17D).

nBT062-SPDB-DM4 and nBT062-SPP-DM1 Inhibit MM1s Cell Adherence to BMSCs

It was analyzed whether the immunoconjugates inhibit multiple myeloma cell adhesion to BMSCs. MM1S cells, which express only moderate levels of CD138 and showed only weakly sensitivity towards BT062 (FIG. 14A and FIG. 15A) were cultured with or without nBT062-SMCC-DM1, nBT062-SPDB-DM4 or nBT062-SPP-DM1 for 2 h (885 ng/ml). After that treatment, MM1S cells were cocultured with BMSCs for further 2 hours. In some samples, the BMSCs were also treated with the immunoconjugates for 12 h (885 ng/ml) prior to coculturing (stroma treat). After 3 washing steps with PBS, adhering cells were measured by [3H]-thymidine uptake.

FIG. 17E shows BMSCs cultured 24 hours in 96 well flat-bottom plates in the presence or absence of immunoconjugates. BMSCs were washed three times with PBS. MM1 S cells which were incubated for 2 hours with the immunoconjugates were given to the BMSCs. DNA synthesis was measured by [3H]-thymidine uptake.

As depicted in FIG. 17E, nBT062-SPDB-DM4 and nBT062-SPP-DM1 inhibited multiple myeloma cell adhesion to BMSCs compared to samples in which just the stroma cells were treated (3.6 fold and 2.5 fold, respectively). nBT062-SMCC-DM1 showed almost no effect on cell adhesion. The result suggest that nBT062-SPDB-DM4 and nBT062-SPP-DM1 are able to disturb MM cell adhesion to BMSCs and that these immunoconjugates are also able to overcome cell adhesion-mediated drug resistance (CAM-DR).

nBT062-SPDB-DM4 Inhibits Tumor Growth in a Human Mm Xenograft Model in SCID Mice The in vivo activities of nBT062-SPDB-DM4 and nBT062-SPP-DM1 were determined in a GFP-positive human MM xenograft model in SCID mice.

Figure 18A:
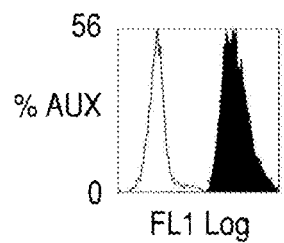
FIG. 18 (A) depicts an analysis of GFP expression by $OPM1^{GFP}$ cells.
Figure 18B:
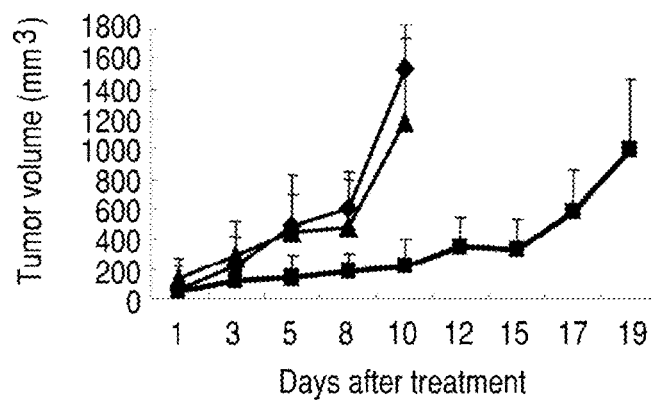
Figure 18C:
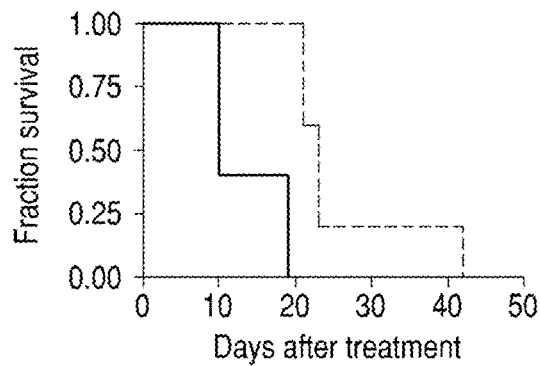
Figure 18D:
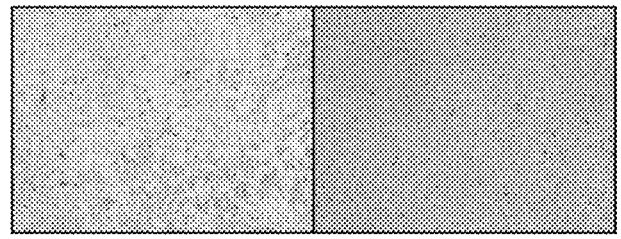

FIG. 18A shows an analysis of GFP expression by OPM1$^{GFP}$ cells. As depicted in the Figure, a highly fluorescent clone of OPM1 mM cells (OPM1$^{GFP}$) could be established and the anti tumor activity of the immunoconjugates with these cells in experimental animals in vivo were examined. In FIG. 18B, 5 mice per group were injected with $5 \times 10^6$ OPM1$^{GFP}$ cells. The mice were inoculated subcutaneously with $5 \times 10^6$ OPM1$^{GFP}$ cells in 100 µl RPMI-1640 media. Treatment with nBT062-SPDB-DM4 (squares), nBT062-SPP-DM1 (triangles) or buffer control was begun when tumors were established. Tumor sizes were determined by serial caliper of perpendicular diameters. Error bars indicate standard deviations. All mice developed measurable tumors 14 days after injection of tumor cells and were then randomized to receive treatment once weekly with nBT062-SPDB-DM4, nBT062-SPP-DM1 or control vehicle (PBS). Serial caliper measurements of perpendicular diameters were performed every other day to calculate tumor volume. Treatment of tumor-bearing mice with nBT062-SPDB-DM4 (176 µg/mouse based on the molecular weight of the conjugate, once weekly for 4 weeks) significantly inhibited MM tumor growth, as compared with control animals treated with PBS vehicle (Dunn's multiple comparison test; control vehicle vs. nBT062-SPDB-DM4: P<0.01 FIG. 16B). The nBT062-SPP-DM1 conjugate was less effective than nBT062-SPDB-DM4 (Dunn's multiple comparison test; nBT062-SPP-DM1 vs. BT062-SPDB-DM4: P<0.05 FIG. 5B). All control mice had to be killed at day 19 after begin of treatment, because of large tumor sizes. Using Kaplan-Meier curves and log-rank analysis, the mean OS was 13.6 days (95% confidence interval [CI], 10-19 days) in the control cohort versus 26 days (95% CI, 23-42 days) in groups treated with nBT062-SPDB-DM4, respectively (FIG. 5C). As can be seen from FIG. 18C, nBT062-SPDB-DM4 significantly increased survival (P<0.0023, dashed line, n=5) compared with the control group treated with vehicle only (solid line; normal saline, n=5). Mice were killed and tumors from a nBT062-SPDB-DM4 treated mouse and a buffer treated control mouse were excised for TUNEL analysis. Ex vivo analysis of tumors excised from OPM1$^{GFP}$-bearing mice showed significantly increased apoptosis in BT062-treated animals as compared to control mice (FIG. 18D). Thus, nBT062-SPDB-DM4 induces apoptosis in vivo. Neither of the compounds administered showed any influence on body weight in this study.

Discussion

Above, a selective anti tumor activity of nBT062-SMCC-DM1, nBT062-SPDB-DM4 and nBT062-SPP-DM1 against CD138 expressing MM cells in vitro and in experimental animals in vivo was demonstrated. Using immunoblotting and immunofluorescence analysis, we found that the majority of MM cell lines analyzed express CD138. DOX40, however, did not express CD138 protein and MM1S and LR5 cells showed weak expression of the protein. The remaining five showed high levels of CD138 expression. The immunoconjugates nBT062-SMCC-DM1, nBT062-SPDB-DM4 and nBT062-SPP-DM1 showed significant cytotoxicity against MM cell lines with nBT062-SPDB-DM4 being the most potent compound of these three agents. OPM1 and RPM18226 cells which express high levels of CD138 were more sensitive towards the immunoconjugates than CD138 low expressing MM1s cells or CD138 negative Dox40 cells. Importantly, these agents were also cytotoxic against tumor cells isolated from patients suffering from MM. Importantly, no cytotoxicity was observed against peripheral or bone marrow mononuclear cells from healthy volunteers. These results suggest that the immunoconjugates have antigen-selective activity against MM tumor cells. It could be demonstrated that nBT062-SMCC-DM1, nBT062-SPDB-DM4 and nBT062-SPP-DM1 inhibit the cell proliferation of MM cells by inducing G2/M cell cycle arrest leading to apoptotic cell death. Cleavage of caspase-3, -8, -9 and the caspase-3 downstream target PARP can be detected in OPM1 cells treated with the immunoconjugates. In addition, APO2.7 antigen -positive cells were increased after twenty-four hours incubation with these drugs.

It was previously reported that IL-6 triggers proliferation of multiple myeloma cells via activation of PI3-K/Akt, MEK/ERK and JAK2/STAT3 signaling cascades. IGF-1 has been described to also promote multiple myeloma cell proliferation and survival using the same pathways. IL-6 protects against dexamethasone-induced apoptosis via induction of PI3-K/Akt signaling. It was examined whether exogenous IL-6 and IGF-1 inhibit immunoconjugate-induced cytotoxicity in multiple myeloma cells. Although increased proliferation was noted in cells treated with IL-6 or IGF-1, these cytokines could not inhibit nBT062-SPDB-DM4-induced apoptosis in OPM1 cells, suggesting that these agents can overcome the protective effects of these cytokines. Importantly, the immunoconjugates inhibited growth and adherence of MM1S cells adhered to BMSCs, further confirming that they can overcome cell adhesion-mediated drug resistance (CAM-DR). In experimental animals, the nBT062-SPDB-DM4 induced significant growth delay of established MM xenografts without influencing mice body weights.

All conjugates tested showed high cytotoxic activity against MM cell lines and against patient-derived primary MM cells, whereas peripheral blood mononuclear cells from healthy volunteers showed no sensitivity towards the conjugates.

The CD138 specific immunoconjugates triggered G2/M cell cycle arrest and induced apoptosis in target cells, associated with cleavage of caspase-8/-9/and -3 and cleavage of the caspase-3 downstream target PARP. Importantly, interleukin-6, insulin-like growth factor-I or presence of bone marrow stromal cells did not protect MM cells against immunoconjugate mediated cytotoxicity.

The nBT062-SPDB-DM4 conjugate significantly inhibited MM tumor growth (p<0.01) and prolonged survival of the mice.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Akkina R K, Rosenblatt J D, Campbell A G, Chen I S, Zack J A. Modeling human lymphoid precursor cell gene therapy in the SCID-hu mouse. Blood. 1994; 84:1393-1398.

Armour K L, Clark M R, Hadley A G, et al. Recombinant human IgG molecules lacking Fcgamma receptor I binding and monocyte triggering activities. Eur J Immunol. 1999; 29(8):2613-24.

Anderson K C, Kyle R A, Dalton W S, Landowski T, Shain K, Jove R, Hazlehurst L, Berenson J. Multiple Myeloma New Insights and Therapeutic Approaches. Hematology 2000; 147-165.

Anttonen A, Heikkila P, Kajanti M, Jalkanen M, Joensuu H. High syndecan-1 expression is associated with favourable outcome in squamous cell lung carcinoma treated with radical surgery. Lung Cancer. 2001 June; 32(3):297-305.

Barbareschi M, Maisonneuve P, Aldovini D, Cangi M G, Pecciarini L, Angelo Mauri F, Veronese S, Caffo O, Lucenti A, Palma P D, Galligioni E, Doglioni C. High syndecan-1 expression in breast carcinoma is related to an aggressive phenotype and to poorer prognosis. Cancer. 2003 Aug. 1 ; 98(3):474-83.

Bataille R, Jégo G, Robillard N, Barillé-Nion S, Harousseau J L, Moreau P, Amiot M, Pellat-Deceunynck C. The phenotype of normal, reactive and malignant plasma cells. Identification of "many and multiple myelomas" and of new targets for myeloma therapy. Haematologica. 2006 September; 91(9):1234-40. Review.

Bernfield M, Kokenyesi R, Kato M, Hinkes M T, Spring J, Gallo R L, Lose E J. Biology of the syndecans: a family of transmembrane heparan sulfate proteoglycans. Annu Rev Cell Biol. 1992; 8:365-393.

Beste G, Schmidt F S, Stibora T, Skerra A. Small antibody-like proteins with prescribed ligand specificities derived from the lipocalin fold. Proc. Natl. Acad. Sci. USA. 1999: 96, 1898-1903.

Bhattacharyya B, Wolff J. Maytansine binding to the vinblastine sites of tubulin. FEBS Lett. 1977; 75:159-162.

Bisping G, Kropff M, Wenning D, Dreyer B, Bessonov S, Hilberg F, Roth G J, Munzert G, Stefanic M, Stelljes M, Scheffold C, Müller-Tidow C, Liebisch P, Lang N, Tchinda J, Serve H L, Mesters R M, Berdel W E, Kienast J. Targeting receptor kinases by a novel indolinone derivative in multiple myeloma: abrogation of stroma-derived interleukin-6 secretion and induction of apoptosis in cytogenetically defined subgroups. Blood. 2006 Mar. 1 ; 107(5):2079-89. Epub 2005 Nov. 8.

Blättler W A and Chari R V J. Drugs to Enhance the Therapeutic Potency of Anticancer Antibodies: Antibody-Drug Conjugates as Tumor-Activated Prodrugs. In: Ojima, I., Vite, G. D. and Altmann, K.-H., Editors, 2001. Anticancer Agents-Frontiers in Cancer Chemotherapy, American Chemical Society, Washington, D.C., pp. 317-338.

Bross P F, Beitz J, Chen G, Chen X H, Duffy E, Kieffer L, Roy S, Sridhara R, Rahman A, Williams G, Pazdur R. Approval summary: gemtuzumab ozogamicin in relapsed acute myeloid leukemia. Clin Cancer Res. 2001; 7:1490-1496.

Carbone A, Gaidano G, Gloghini A, Ferlito A, Rinaldo A, Stein H. AIDS-related plasma-blastic lymphomas of the oral cavity and jaws: a diagnostic dilemma. Ann. 0 to 1. Rhinol. Laryngol. 1999; 108: 95-99.

Carlsson J, Drevin H, Axen R. Protein thiolation and reversible protein-protein conjugation. N-succinimidyl-3-(2-pyridyldithio)propionate, a new heterobifunctional reagent. Biochem J 1978; 173: 723-737.

Carter P. Improving the efficacy of antibody-based cancer therapies. Nat Rev Cancer. 2001 ; 1:118-129.

Chari R V, Martell B A, Gross J L, Cook S B, Shah S A, Blattler W A, McKenzie S J, Goldmacher V S. Immunoconjugates containing novel maytansinoids: promising anticancer drugs. Cancer Res. 1992; 52:127-131.

Chari R V, Jackel K A, Bourret L A, Derr S M, Tadayoni B M, Mattocks K M, Shah S A, Liu C, Blättler W A and Goldmacher V S. Enhancement of the selectivity and antitumor efficacy of a CC-1065 analogue through immunoconjugate formation. Cancer Res. 1995; 55: 4079-4084.

Charnaux N, Brule S, Chaigneau T, Saffar L, Sutton A, Hamon M, Prost C, Lievre N, Vita C, Gattegno L. RANTES (CCL5) induces a CCR5-dependent accelerated shedding of syndecan-1 (CD138) and syndecan-4 from HeLa cells and forms complexes with the shed ectodomains of these proteoglycans as well as with those of CD44. Glycobiology. 2004 Sep. 8 [Epub ahead of print]

Chen B P, Galy A, Kyoizumi S, Namikawa R, Scarborough J, Webb S, Ford B, Cen D Z, Chen S C. Engraftment of human hematopoietic precursor cells with secondary transfer potential in SCID-hu mice. Blood. 1994; 84:2497-2505.

Chilosi M, Adami F, Lestani M, Montagna L, Cimarosto L, Semenzato G, Pizzolo G, Menestrina F. CD138/syndecan-1: a useful immunohistochemical marker of normal and neoplastic plasma cells on routine trephine bone marrow biopsies. Mod Pathol. 1999; 12:1101-1106.

Clement C, Vooijs, W. C., Klein, B., and Wijdenes, J. In: al. SFSe, ed. J. Leukocyte Typing V. Oxford: Oxford University Press; 1995:714-715.

Couturier 0 Faivre-Chauvet A ; Filippovich I V; Thedréz P, Saï-Maurel C; Bardiés M; Mishra A K; Gauvrit M; Blain G; Apostolidis C; Molinet R; Abbe J C; Bateille R; Wijdenes J; Chatal J F; Cherel M; Validation of 213Bi-alpha radioimmunotherapy for multiple myeloma. Clinical Cancer Research 5(10 Suppl.) (October 1999) 3165s-3170s.

Davies E J et al., Blackhall F H, Shanks J H, David G, McGown A T, Swindell R, Slade R J, Martin-Hirsch P, Gallagher J T, Jayson G C. Distribution and Clinical Significance of Heparan Sulfate Proteoglycans in Ovarian Cancer Clin Cancer Res. 2004; 10(15):5178-86.

Dhodapkar M V, Abe E, Theus A, Lacy M, Langford J K, Barlogie B, Sanderson R D. Syndecan-1 is a multifunctional regulator of myeloma pathobiology: control of tumor cell survival, growth, and bone cell differentiation. Blood. 1998; 91:2679-2688.

Dore J M, Morard F, Vita N, Wijdenes J. Identification and location on syndecan-1 core protein of the epitopes of B-B2 and B-B4 monoclonal antibodies. FEBS Lett. 1998; 426:67-70.

Dowell J A, Korth-Bradley J, Liu H, King S P, Berger M S. Pharmacokinetics of gemtuzumab ozogamicin, an antibody-targeted chemotherapy agent for the treatment of patients with acute myeloid leukemia in first relapse. J Clin Pharmacol. 2001 ; 41:1206-1214.

Edinger M, Sweeney T J, Tucker A A, Olomu A B, Negrin R S, Contag C H. Noninvasive assessment of tumor cell proliferation in animal models. Neoplasia. 1999; 1:303-310.

Gattei V, Godeas C, Degan M, Rossi F M, Aldinucci D, Pinto A. Characterization of Anti-CD138 monoclonal antibodies as tools for investigating the molecular polymorphism of syndecan-1 in human lymphoma cells. Br J Haematol. 1999; 104:152-162.

Hamann P R, Hinman L M, Beyer C F, Lindh D, Upeslacis J, Flowers D A, Bernstein I. An anti-CD33 antibody-calicheamicin conjugate for treatment of acute myeloid leukemia. Choice of linker. Bioconjug Chem. 2002; 13:40-46.

Han I, Park H, Oh E S. New insights into syndecan-2 expression and tumorigenic activity in colon carcinoma cells. J Mol Histol. 2004: 35(3):319-26.

Hideshima T, Catley L, Yasui H, Ishitsuka K, Raje N, Mitsiades C, Podar K, Munshi N C, Chauhan D, Richardson P G, Anderson K C. Perifosine, an oral bioactive novel alkylphospholipid, inhibits Akt and induces in vitro and in vivo cytotoxicity in human multiple myeloma cells. Blood 2006; 107(10):4053-62.

Hideshima T, Mitsiades C, Tonon G, Richardson P G, Anderson K C. Understanding multiple myeloma pathogenesis in the bone marrow to identify new therapeutic targets. Nat Rev Cancer 2007; 7(8):585-98.

Horvathova M, Gaillard, J.-P., Liutard, J., Duperray, C., Lavabre-Bertrand, T., Bourquard, P et al. In: al. SFSe, ed. Leucocyte Typing V. Oxford: Oxford University Press; 1995:713-714.

Kovtun Y V, Audette C A, Ye Y, Xie H, Ruberti M F, Phinney S J, et al. Antibody-drug conjugates designed to eradicate tumors with homogeneous and heterogeneous expression of the target antigen. Cancer Res 2006; 66 (6):3214-21.

Krebs B, Rauchenberger R, Reiffert S, Rothe C, Tesar M, Thomassen E, Cao M, Dreier T, Fischer D, Hoss A et al. High-throughput generation and engineering of recombinant human antibodies. 2001. J. Immunol. Methods 254, pp. 67-84.

Kupchan S M, Sneden A T, Branfman A R, Howie G A, Rebhun L I, Mclvor W E, Wang R W, Schnaitman T C. Structural requirements for antileukemic activity among the naturally occurring and semisynthetic maytansinoids. J Med Chem. 1978; 21:31-37.

Kyoizumi S, Baum C M, Kaneshima H, McCune J M, Yee E J, Namikawa R. Implantation and maintenance of functional human bone marrow in SCID-hu mice. Blood. 1992; 79:1704-1711.

Kyoizumi S, Murray L J, Namikawa R. Preclinical analysis of cytokine therapy in the SCID-hu mouse. Blood. 1993; 81:1479-1488.

Langford J K, Stanley M J, Cao D, Sanderson R D. Multiple heparan sulfate chains are required for optimal syndecan-1 function. J Biol Chem. 1998 Nov. 6; 273(45): 29965-71.

Liu C, Tadayoni B M, Bourret L A, Mattocks K M, Derr S M, Widdison W C, Kedersha N L, Ariniello P D, Goldmacher V S, Lambert J M, Blattler W A, Chari R V. Eradication of large colon tumor xenografts by targeted delivery of maytansinoids. Proc Natl Acad Sci USA. 1996; 93:8618-8623.

McCune J M, Namikawa R, Kaneshima H, Shultz L D, Lieberman M, Weissman I L. The SCID-hu mouse: murine model for the analysis of human hematolymphoid differentiation and function. Science. 1988; 241:1632-1639.

Mennerich D, Vogel A, Klaman I, Dahl E, Lichtner R B, Rosenthal A, Pohlenz H D, Thierauch K H, Sommer A. Shift of syndecan-1 expression from epithelial to stromal cells during progression of solid tumours. Eur J Cancer. 2004 June; 40(9):1373-82.

Mosmann T. Rapid colorimetric assay for cellular growth and survival: application to proliferation and cytotoxicity assays. J Immunol Methods. 1983; 65:55-63.

Munshi N C, Longo D L, Anderson K C. Plasma cell disorders. In: Braunwald E, Fauci A S, Kasper D L, Hauser S L, Longo D L, Jameson J L, editors. Harrison's Principles of Internal Medicine. 16th ed. New York: McGraw-Hill Medical Publishing Division; 2008. p. 700-7.

Namikawa R, Ueda R, Kyoizumi S. Growth of human myeloid leukemias in the human marrow environment of SCID-hu mice. Blood. 1993; 82:2526-2536.

O'Connell F P, Pinkus J L, Pinkus G S. CD138 (Syndecan-1), a Plasma Cell Marker Immunohistochemical Profile in Hematopoietic and Nonhematopoietic Neoplasms. Am J Clin Pathol 2004; 121:254-263.

Ojima I, Geng X, Wu X, Qu C, Borella C P, Xie H, Wilhelm S D, Leece B A, Bartle L M, Goldmacher V S and Chari R V. Tumor-specific novel taxoid-monoclonal antibody conjugates. 2002. J. Med. Chem. 45, pp. 5620-5623.

Olafsen, T, Cheung, C C, Yazaki, P J, Li L, Sundaresan G, Gambhir S S, Sherman, M A, Williams, L E, Shively, J E, Raubitschek, A A, and Wu, A M. Covalent disulfide-linked anti-CEA diabody allows site-specific conjugation and radiolabeling for tumor targeting applications. 2004; Prot. Eng. Design & Selection 17:1: 21-27.

Orosz Z, Kopper L. Syndecan-1 expression in different soft tissue tumours. Anticancer Res. 2001; 21(1B):733-7.

Padlan, E A. A possible procedure for reducing the immunogenicity of antibody variable domains while preserving their ligand-binding properties. Mol. Immunol. 1991; 28: 489-498.

Payne G. Progress in immunoconjugate cancer therapeutics. Cancer Cell. 2003; 3:207-212.

Pegram M D, Lipton A, Hayes D F, Weber B L, Baselga J M, Tripathy D, Baly D, Baughman S A, Twaddell T, Glaspy J A and Slamon D J. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. 1998. J. Clin. Oncol. 16, pp. 2659-2671.

Rawstron A C, Owen R G, Davies F E, Johnson R J, Jones R A, Richards S J, Evans P A, Child J A, Smith G M, Jack A S, Morgan G J. Circulating plasma cells in multiple myeloma: characterization and correlation with disease stage. Br J Haematol. 1997; 97:46-55.

Remillard S, Rebhun L I, Howie G A, Kupchan S M. Antimitotic activity of the potent tumor inhibitor maytansine. Science. 1975; 189:1002-1005.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994; 91:969-973.

Ross S, Spencer S D, Holcomb I, Tan C, Hongo J, Devaux B, Rangell L, Keller G A, Schow P, Steeves R M, Lutz R J, Frantz G, Hillan K, Peale F, Tobin P, Eberhard D, Rubin M A, Lasky L A, Koeppen H. Prostate stem cell antigen as therapy target: tissue expression and in vivo efficacy of an immunoconjugate. Cancer Res. 2002 May 1 ; 62(9): 2546-53.

Ross J S, Gray K, Gray G, Worland P J, Rolfe M. Anticancer Antibodies, Am J Clin Path. (Apr. 17, 2003).

Sanderson R D, Lalor P, Bernfield M. B lymphocytes express and lose syndecan at specific stages of differentiation. Cell Regul. 1989; 1:27-35.

Sandhu J S, Clark B R, Boynton E L, Atkins H, Messner H, Keating A, Hozumi N. Human hematopoiesis in SCID mice implanted with human adult cancellous bone. Blood. 1996; 88:1973-1982.

Sasaki A, Boyce B F, Story B, Wright K R, Chapman M, Boyce R, Mundy G R, Yoneda T. Bisphosphonate risedronate reduces metastatic human breast cancer burden in bone in nude mice. Cancer Res. 1995; 55:3551-3557.

Schneider U, van Lessen A, Huhn D, Serke S. Two subsets of peripheral blood plasma cells defined by differential expression of CD45 antigen. Br J Haematol. 1997; 97:56-64.

Schuurman J, Van Ree R, G. J. Perdok G J, Van Doorn H R, Tan K Y, Aalberse R C, Normal human immunoglobulin G4 is bispecific: it has two different antigen-combining sites, Immunology 1999; 97:693-698.

Sebestyen A, Berczi L, Mihalik R, Paku S, Matolcsy A, Kopper L. Syndecan-1 (CD138) expression in human non-Hodgkin lymphomas. Br J Haematol. 1999; 104(2): 412-9.

Seftalioglu A, Karakus S. Syndecan-1/CD138 expression in normal myeloid, acute lymphoblastic and myeloblastic leukemia cells. Acta Histochem. 2003; 105:213-221.

Seftalioglu A, Karakus S, Dundar S, Can B, Erdemli E, Irmak M K, Oztas E, Korkmaz C, Yazar F, Cavusoglu I. Syndecan-1 (CD138) expression in acute myeloblastic leukemia cells—an immuno electron microscopic study. Acta Oncol. 2003; 42:71-74.

Senter P D, Doronina S, Cerveny C, Chace D, Francisco J, Klussman K, Mendelsohn B, Meyer D, Siegall C B, Thompson J et al. (2002). Cures and regressions of established tumors with monoclonal antibody auristatin conjugates. Abstract #2062, American Association for Cancer Res. (San Francisco, Calif.: American Association for Cancer Res.), 414.

Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001; 276(9):6591-604.

Sievers E L, Larson R. A., Stadtmauer, E. A., Estey, E., Lowenberg, B., Dombret, H., Karanes, C., Theobald, M., Bennett, J. M., Sherman, M. L. et al. Efficacy and safety of gemtuzumab ozogamicin in patients with CD33-positive acute myeloid leukemia in first relapse. 2001. J. Clin. Oncol. 19, pp. 3244-3254.

Sievers E L and Linenberger M. Mylotarg: antibody-targeted chemotherapy comes of age. 2001. Curr. Opin. Oncol. 13, pp. 522-527.

Smith R., Single chain antibody variable region fragments; Stanford University website (last updated on May, 2001).

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994: 7(6): 805-814.

Tai Y T, Li X F, Catley L, Coffey R, Breitkreutz I, Bae J, Song W, Podar K, Hideshima T, Chauhan D, Schlossman R, Richardson P, Treon S P, Grewal I S, Munshi N C, Anderson K C. Immunomodulatory drug lenalidomide (CC-5013, IMiD3) augments anti-CD40 SGN-40-induced cytotoxicity in human multiple myeloma: clinical implications. Cancer Res. 2005 Dec. 15; 65(24):11712-20.

Tassone P, Goldmacher V S, Neri P, Gozzini A, Shammas M A, Whiteman K A, Hylander-Gans L L, Carrasco D R, Hideshima T, Shringarpure R, Shi J, Allam C K, Wijdenes J, Venuta S, Munshi N C, Anderson K C, Cytotoxic activity of the maytansinoid immunoconjugate B-B4-DM1 against CD138+ multiple myeloma cells, Blood, 2004, 104 (12), pp. 3688-3696.

Tolcher A W, Ochoa L, Hammond L A, Patnaik A, Edwards T, Takimoto C, Smith L, de Bono J, Schwartz G, Mays T, Jonak Z L, Johnson R, DeWitte M, Martino H, Audette C, Maes K, Chari R V, Lambert J M, Rowinsky E K. Cantuzumab mertansine, a maytansinoid immunoconjugate directed to the CanAg antigen: a phase 1, pharmacokinetic, and biologic correlative study. J Clin Oncol. 2003; 21:211-222.

Urashima M, Chen B P, Chen S, Pinkus G S, Bronson R T, Dedera D A, Hoshi Y, Teoh G, Ogata A, Treon S P, Chauhan D, Anderson K C. The development of a model for the homing of multiple myeloma cells to human bone marrow. Blood. 1997; 90:754-765.

Vogel C W. Preparation of immunoconjugates using antibody oligosaccharide moieties. Methods in Molecular Biology: Bioconjugation protocols strategies and methods. 2004; 283:087-108.

Vooijs W C, Post J, Wijdenes J, Schuurman H J, Bolognesi A, Polito L, Stirpe F, Bast E J, de Gast G C. Efficacy and toxicity of plasma-cell-reactive monoclonal antibodies B-B2 and B-B4 and their immunotoxins. Cancer Immunol Immunother. 1996; 42:319-328.

Ward, E. S., D. Gussow, A. D. Griffiths, P. T. Jones, and G. Winter. Binding activities of a repertoire of single immunoglobin variable domains secreted from *Escherichia coli*. Nature. 1989. 341:544-546.

Wargalla U C, Reisfeld R A. Rate of internalization of an immunotoxin correlates with cytotoxic activity against human tumor cells. Proc. Natl. Acad. Sci. USA. 1989; 86:5146-5150.

Wijdenes J, Vooijs W C, Clement C, Post J, Morard F, Vita N, Laurent P, Sun R X, Klein B, Dore J M. A plasmocyte selective monoclonal antibody (B-B4) recognizes syndecan-1. Br J Haematol. 1996; 94:318-323.

Wijdenes J, Dore J M, Clement C, Vermot-Desroches C. CD138, J Biol Regul Homeost Agents. 2002 Apr.-Jun.; 16(2):152-5.

Witzig T E, Kimlinger T K, Ahmann G J, Katzmann J A, Greipp P R. Detection of myeloma cells in the peripheral blood by flow cytometry. Cytometry. 1996; 26:113-120.

Xie H, Audette C, Hoffee M, Lambert J M, Blättler W. Pharmacokinetics and biodistribution of the antitumor immunoconjugate, cantuzumab mertansine (huC242-DM1), and its two components in mice. J Pharmacol Exp Ther. 2004 March; 308(3):1073-82.

Yang M, Jiang P, An Z, Baranov E, Li L, Hasegawa S, Al-Tuwaijri M, Chishima T, Shimada H, Moossa A R, Hoffman R M. Genetically fluorescent melanoma bone and organ metastasis models. Clin Cancer Res. 1999; 5:3549-3559.

Yang M, Baranov E, Jiang P, Sun F X, Li X M, Li L, Hasegawa S, Bouvet M, Al-Tuwaijri M, Chishima T, Shimada H, Moossa A R, Penman S, Hoffman R M. Whole-body optical imaging of green fluorescent protein-expressing tumors and metastases. Proc Natl Acad Sci USA. 2000; 97:1206-1211.

Yang Y, MacLeod V, Dai Y, Khotskaya-Sample Y, Shriver Z, Venkataraman G, Sasisekharan R, Naggi A, Torri G, Casu B, Vlodavsky I, Suva L J, Epstein J, Yaccoby S, Shaughnessy J D Jr, Barlogie B, Sanderson R D. The syndecan-1 heparan sulfate proteoglycan is a viable target for myeloma therapy. Blood. 2007 Sep. 15; 110(6):2041-8. Epub 2007 May 29.

Yoshitake S, Yamada Y, Ishikawa E, Masseyeff R. Conjugation of glucose oxidase from *Aspergillus niger* and rabbit antibodies using N-hydroxysuccinimide ester of N-(4-carboxycyclohexylmethyl)-maleimide. Eur J Biochem 1979; 101:395-399.

---

What is claimed is:

1. A method for destroying multiple myeloma cells and diminishing adhesion of stroma cells to CD138 expressing multiple myeloma cells in multiple myeloma cells of a subject in need thereof comprising:
  (i) administering to said multiple myeloma cells, in a first administration, an immunoconjugate targeting said CD138 expressing multiple myeloma cells said immunoconjugate comprising a chimeric CD138 antibody comprising an antigen binding region which comprises
    (a) a light chain variable region comprising amino acid residues 24-34 (CDR1), residues 50-56 (CDR2) and residues 89-97 (CDR3) of SEQ ID NO: 2, and
    (b) a heavy chain variable region comprising amino acid residues 31-35 (CDR1), residues 51-68 (CDR2) and residues 99-111 (CDR3) of SEQ ID No: 1
  and at least one maytansinoid effector molecule, wherein said effector molecule and said chimeric CD138 antibody are attached to each other via a cleavable linker,
  (ii) waiting for 12 hours to 6 days during which the immunoconjugate:
    (a) destroys multiple myeloma cells, and
    (b) prevents, at least in part, multiple myeloma cells from adhering to bone marrow stromal cells (BMSCs) thus overcoming cell adhesion-mediated drug resistance (CAM-DR), and
  (iii) administering to said multiple myeloma cells, in an administration subsequent to the first administration in (i) and subsequent to (ii), a further cytotoxic agent that is not said immunoconjugate wherein said diminished adhesion results in alleviation of adhesion mediated drug resistance against said further cytotoxic agent.

2. The method of claim 1, wherein the cleavable linker contains a disulfide bond.

3. The method of claim 2, wherein the linker is SPP or SPDB.

4. The method of claim 1, wherein the adhesion is diminished by at least about 10%, about 20%, about 30%, about 40%, about 50%, about 60%, about 70%, about 80% or more.

5. The method of claim 1, wherein said cytotoxic agent is mephalan, vincristine, doxorubicin, dexamethasone, cyclophosphamide, etoposide, cytarabine, cisplatin, thalidomide, prednisone, thalidomide, bortezomib, lenalidomide, sorafenib, romidepsin or combinations thereof.

6. The method of claim 1, wherein said maytansinoid effector molecule is sterically hindered.

7. The method of claim 1, wherein the maytansinoid effector molecule is DM1, DM3, or DM4.

8. The method of claim 7, wherein said effector molecule is DM4.

9. The method of claim 1, wherein said chimeric CD138 antibody comprises:
SEQ ID NO:1 and SEQ ID NO:2.

10. The method of claim 1, wherein the cleavable linker is cleaved releasing the effector molecule and wherein the adhesion of the stroma cells to CD138 expressing tumor cells is diminished by diffusion of said effector molecules to said stroma cells.

* * * * *

SEQUENCE LISTING

```
<160> NUMBER OF SEQ ID NOS: 13

<210> SEQ ID NO 1
<211> LENGTH: 448
<212> TYPE: PRT
<213> ORGANISM: Artificial Sequence
<220> FEATURE:
<223> OTHER INFORMATION: Amino Acid sequence (predicted) of heavy chain
      of chimeric human/mouse antibody
<220> FEATURE:
<221> NAME/KEY: CDR1
<222> LOCATION: (31)..(35)
<220> FEATURE:
<221> NAME/KEY: CDR2
<222> LOCATION: (51)..(68)
<220> FEATURE:
<221> NAME/KEY: CDR3
<222> LOCATION: (99)..(111)
<220> FEATURE:
<221> NAME/KEY: region IgG4
<222> LOCATION: (123)..(448)

<400> SEQUENCE: 1

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
                20                  25                  30

Trp Ile Glu Trp Val Lys Gln Arg Pro Gly His Gly Leu Glu Trp Ile
            35                  40                  45

Gly Glu Ile Leu Pro Gly Thr Gly Arg Thr Ile Tyr Asn Glu Lys Phe
        50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95
```

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Amino Acid sequence (predicted) of light chain
      of chimeric human/mouse antibody
<220> FEATURE:
<221> NAME/KEY: CDR1
<222> LOCATION: (24)..(34)
<220> FEATURE:
<221> NAME/KEY: CDR2

```
<222> LOCATION: (50)..(56)
<220> FEATURE:
<221> NAME/KEY: CDR3
<222> LOCATION: (89)..(97)
<220> FEATURE:
<221> NAME/KEY: region IgG4
<222> LOCATION: (108)..(214)

<400> SEQUENCE: 2

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 31
<212> TYPE: DNA
<213> ORGANISM: Artificial Sequence
<220> FEATURE:
<223> OTHER INFORMATION: IgH primer MHV7

<400> SEQUENCE: 3
atgggcatca agatggagtc acagacccag g                              31

<210> SEQ ID NO 4
<211> LENGTH: 21
<212> TYPE: DNA
<213> ORGANISM: Artificial Sequence
<220> FEATURE:
<223> OTHER INFORMATION: IgG1 constant region primer MHCG1

<400> SEQUENCE: 4
cagtggatag acagatgggg g                                         21

<210> SEQ ID NO 5
<211> LENGTH: 30
```

```
<212> TYPE: DNA
<213> ORGANISM: Artificial Sequence
<220> FEATURE:
<223> OTHER INFORMATION: Ig kappa primer MKV2

<400> SEQUENCE: 5
atggagacag acacactcct gctatgggtg                                    30

<210> SEQ ID NO 6
<211> LENGTH: 33
<212> TYPE: DNA
<213> ORGANISM: Artificial Sequence
<220> FEATURE:
<223> OTHER INFORMATION: Ig kappa primer MKV4

<400> SEQUENCE: 6
atgagggccc ctgctcagtt ttttggcttc ttg                                33

<210> SEQ ID NO 7
<211> LENGTH: 25
<212> TYPE: DNA
<213> ORGANISM: Artificial Sequence
<220> FEATURE:
<223> OTHER INFORMATION: Ig kappa primer MKV9

<400> SEQUENCE: 7
atggtatcca cacctcagtt ccttg                                         25

<210> SEQ ID NO 8
<211> LENGTH: 20
<212> TYPE: DNA
<213> ORGANISM: Artificial Sequence
<220> FEATURE:
<223> OTHER INFORMATION: primer MKC

<400> SEQUENCE: 8
actggatggt gggaagatgg                                               20

<210> SEQ ID NO 9
<211> LENGTH: 50
<212> TYPE: DNA
<213> ORGANISM: Artificial Sequence
<220> FEATURE:
<223> OTHER INFORMATION: forward (For) primer

<400> SEQUENCE: 9
agagaagctt gccgccacca tgattgcctc tgctcagttc cttggtctcc              50

<210> SEQ ID NO 10
<211> LENGTH: 35
<212> TYPE: DNA
<213> ORGANISM: Artificial Sequence
<220> FEATURE:
<223> OTHER INFORMATION: oligonucleotide primer BT03

<400> SEQUENCE: 10
caacagtata gtaagctccc tcggacgttc ggtgg                              35

<210> SEQ ID NO 11
<211> LENGTH: 35
<212> TYPE: DNA
<213> ORGANISM: Artificial Sequence
<220> FEATURE:
<223> OTHER INFORMATION: oligonucleotide primer BT04

<400> SEQUENCE: 11
```

-continued ccaccgaacg tccgagggag cttactatac tgttg 35

<210> SEQ ID NO 12
<211> LENGTH: 41
<212> TYPE: DNA
<213> ORGANISM: Artificial Sequence
<220> FEATURE:
<223> OTHER INFORMATION: primer g2258

<400> SEQUENCE: 12
cgcgggatcc actcacgttt gatttccagc ttggtgcctc c 41

<210> SEQ ID NO 13
<211> LENGTH: 45
<212> TYPE: DNA
<213> ORGANISM: Artificial Sequence
<220> FEATURE:
<223> OTHER INFORMATION: Primer g22949

<400> SEQUENCE: 13
cgatgggccc ttggtggagg ctgaggagac ggtgactgag gttcc 45